US011135367B2

(12) United States Patent
Tubb

(10) Patent No.: US 11,135,367 B2
(45) Date of Patent: Oct. 5, 2021

(54) MEDICAL DEVICE AND METHOD FOR PROVIDING INFORMATION FOR GLYCEMIC CONTROL

(71) Applicant: SANOFI-AVENTIS DEUTSCHLAND GMBH, Frankfurt am Main (DE)

(72) Inventor: Andrew Tubb, Guildford (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 931 days.

(21) Appl. No.: 15/426,240

(22) Filed: Feb. 7, 2017

(65) Prior Publication Data

US 2017/0143901 A1    May 25, 2017

Related U.S. Application Data

(63) Continuation of application No. 13/145,836, filed as application No. PCT/EP2010/051264 on Feb. 3, 2010, now abandoned.

(30) Foreign Application Priority Data

Feb. 4, 2009 (EP) .................................. 09001560

(51) Int. Cl.

| G01N 33/48 | (2006.01) |
|---|---|
| A61M 5/172 | (2006.01) |
| A61B 5/145 | (2006.01) |
| A61M 5/142 | (2006.01) |
| G16H 20/17 | (2018.01) |
| G16H 70/60 | (2018.01) |
| A61M 15/00 | (2006.01) |
| G01N 33/49 | (2006.01) |
| G06F 21/34 | (2013.01) |

(52) U.S. Cl.
CPC ....... *A61M 5/1723* (2013.01); *A61B 5/14532* (2013.01); *A61M 5/142* (2013.01); *A61M 15/0065* (2013.01); *G01N 33/49* (2013.01); *G06F 21/34* (2013.01); *G16H 20/17* (2018.01); *G16H 70/60* (2018.01); *A61M 2205/6009* (2013.01)

(58) Field of Classification Search
None
See application file for complete search history.

(56) References Cited

U.S. PATENT DOCUMENTS

| 6,958,691 | B1 | 10/2005 | Anderson et al. |
|---|---|---|---|
| 8,504,179 | B2 | 8/2013 | Blomquist |
| 2002/0107476 | A1 | 8/2002 | Mann et al. |
| 2003/0114836 | A1 | 6/2003 | Estes et al. |
| 2003/0163088 | A1 | 8/2003 | Blomquist |
| 2004/0122353 | A1 | 6/2004 | Shahmirian et al. |
| 2005/0043965 | A1 | 2/2005 | Heller et al. |
| 2005/0214892 | A1 | 9/2005 | Kovatchev et al. |
| 2005/0277911 | A1 | 12/2005 | Stewart et al. |
| 2006/0149588 | A1 | 7/2006 | Hauck et al. |
| 2008/0126969 | A1 | 5/2008 | Blomquist |
| 2008/0172027 | A1 | 7/2008 | Blomquist |
| 2008/0214919 | A1 | 9/2008 | Harmon et al. |
| 2008/0234992 | A1 | 9/2008 | Ray et al. |
| 2008/0269672 | A1 | 10/2008 | Say et al. |
| 2008/0319384 | A1 | 12/2008 | Yodfat |

FOREIGN PATENT DOCUMENTS

| CN | 1616966 A | 5/2005 |
|---|---|---|
| CN | 1688244 A | 10/2005 |
| CN | 101290320 A | 10/2008 |
| CN | 101342090 A | 1/2009 |
| JP | 2003-290345 A | 10/2003 |
| WO | 2000/29047 A1 | 5/2000 |
| WO | 03/046695 | 6/2003 |
| WO | 2003/071930 A2 | 9/2003 |
| WO | 2005/037092 A1 | 4/2005 |
| WO | 2006/131345 A1 | 12/2006 |
| WO | 2007/000427 A1 | 1/2007 |
| WO | 2009/001349 A1 | 12/2008 |
| WO | 2009/048462 A1 | 4/2009 |

OTHER PUBLICATIONS

International Search Report for PCT App. No. PCT/EP2010/051264, dated Apr. 26, 2010.
Anthony Barnet, "Dosing of Insulin Glargine in the Treatment of Type 2 Diabetes", Clinical Therapeutics, vol. 29, No. 6, 2007, pp. 987-999.
H. Yki-Järvinen et al., "Insulin glargine or NPH combined with metformin in type 2 diabetes: he LANMET Study", Diabetologica, vol. 49, p. 442-451, 2005.
H.C. Gerstein et al., "A randomized trial of adding insulin glargine vs. avoidance of insulin in people with Type 2 diabetes on either no oral glucose—lowering agents or submaximal doses of metformin and/or sulphonylureas, The Canadian INSIGHT (Implementing New Strategies with Insulin Glargine for Hyperglycaemia Treatment) Study", Diabetic Medicine, vol. 23, 2006, pp. 736-742.
Melanie Davies et al., "Improvement of Glycemic Control in Subjects With Poorly Controlled Type 2 Diabetes", Diabetes Care, vol. 28, No. 6, Jun. 2005, pp. 1282-1288.

(Continued)

*Primary Examiner* — Anna Skibinsky

(74) *Attorney, Agent, or Firm* — McCarter & English, LLP

(57) ABSTRACT

A medical device for providing information for glycemic control is provided, wherein the device comprises storage means arranged to store data, receiving means arranged to receive blood glucose value data and security data, data processing means arranged to execute a first processing function for modifying data retrieved from the storage means and to execute a second processing function for providing information for glycemic control based on the blood glucose value data and data retrieved from the storage means, validating means arranged to validate the received security data and to provide validation data corresponding to the validation of the received security data, and safety means arranged to control an execution of at least a predetermined function out of the first and second processing functions based on the validation data.

20 Claims, 38 Drawing Sheets

(56) References Cited

OTHER PUBLICATIONS

Nathan et al., "Management of hyperglycemia in type 2 diabetes: A consensus algorithm for the initiation and adjustment of therapy: a consensus statement from the American Diabetes Association and the European Association for the Study of Diabetes," Diabetes Care, vol. 29, No. 8, 2006, pp. 1963-1972.
Poul Strange, "Treat-to-Target Insulin Titration Algorithms When Initiating Long or Intermediate Acting Insulin in Type 2 Diabetes", Journal of Diabetes Science and Technology, vol. 1, issue 4, Jul. 2007, pp. 540-548.
Robert J. Heine et al., "Exenatide versus Insulin Glargine in Patients with Suboptimally Controlled Type 2 Diabetes, A Randomized Trial", Annals of Internal Medicine, vol. 143, No. 8, Oct. 2005, pp. 559-569.
Bluetooth, "Specification of the Bluetooth System, Specification vol. 1, Wireless connection made easy," v 1.0B, Dec. 1, 1999, 1082 pp.
European Search Report for EP Application No. 17182868, dated Oct. 24, 2017.
Davies et al., Insulin glargine-based therapy improves glycemic control in patients with type 2 diabetes sub-optimally controlled on premixed insulin therapies. Diabetes Res Clin Pract. Feb. 2008;79(2):368-75.
Meneghini et al., The usage of a simplified self-titration dosing guideline (303 Algorithm) for insulin detemir in patients with type 2 diabetes—results of the randomized, controlled Predictive 303 study. Diabetes Obes Metab. Nov. 2007;9(6):902-13.
Schaefer, Is Diabetes Mellitus Ready for the "Do It Yourself" Approach? Physicians' Corner. Oct. 2007;2(4):154-156.

MEDICAL DEVICE AND METHOD FOR PROVIDING INFORMATION FOR GLYCEMIC CONTROL

CROSS REFERENCE TO RELATED APPLICATIONS

The present application is a continuation of U.S. patent application Ser. No. 13/145,836, filed Nov. 16, 2011, which is a U.S. National Phase Application pursuant to 35 U.S.C. § 371 of International Application No. PCT/EP2010/051264 filed Feb. 3, 2010, which claims priority to EP Patent Application No. 09001560.3 filed on Feb. 4, 2009. The entire disclosure contents of these applications are herewith incorporated by reference into the present application.

FIELD OF THE INVENTION

The present invention relates to a medical device and system for providing information for glycemic control and to a device and method for configuring such a medical device. In particular, the invention relates to an automated medical device which provides safety means to control an execution of at least a predetermined function provided by the medical device. Moreover, it refers to a method and device for configuring a process or function of the medical device.

BACKGROUND OF THE INVENTION

People with diabetes are either deficient in insulin or are unable to make sufficient insulin to overcome underlying insulin resistance or to normalize the glucose metabolism. In order to achieve a better glycemic control or even to regain almost full glycemic control often basal insulin or insulin glargine treatment is used which is based upon a set of rules set for periodic blood glucose measurements in order to obtain information on the progress of the treatment. With regard to this it has to be considered that the blood glucose levels fluctuate throughout the day. A "perfect glucose level" would mean that glucose levels are always in a range of 70 to 130 mg/dl or 3.9 to 7.2 nmol/L and undistinguishable from a person without diabetes.

In order to achieve this or to get as close as possible to such a "perfect glycemic control" blood glucose values are monitored once or several times during the day as relying on their own perception of symptoms of hyperglycemia or hypoglycemia is usually unsatisfactory as mild to moderate hypoglycemia causes no obvious symptoms in nearly all patients. If the blood glucose value is too high, e.g. over 130 mg/dl, insulin or insulin analogues can be administered.

For the insulin therapy long-acting basal insulin or insulin glargine, which are long-acting basal insulin analogues, are used. These insulin or insulin analogues are usually given once daily to help control the blood sugar level of patients with diabetes. The advantage of long-acting basal insulin or insulin glargine is that they have a duration of action of more than 24 hours or even more with a less peaked profile than NPH. Thus, it more closely resembles the basal insulin secretion of the normal pancreatic β-cells.

For good or perfect glycemic control the dose of basal insulin or insulin glargine has to be adjusted for each individual in accordance with a blood glucose level to be achieved. Usually, the dose of insulin or insulin glargine is increased from an initial dose to a final dose over a certain time period until the specific blood glucose value, typically the fasting blood glucose (FBG) value has reached the target range. In practice, such titration can be done by the health care professionals (HCPs). However, the patient may be empowered and trained by the health care professionals to do their own titration. Such a self-titration can be supported by an intervention from a third party support or services or some intermediate combination.

In the every day use basal insulin or insulin glargine are typically under-dosed. Thus, there remains a gap between the initial dosing and an optimal dosing for achieving perfect or almost perfect glycemic control. This has a number of negative effects which better titration could help to eliminate. For example, if patients are not titrated, their blood sugar does not come down and as a result they do not feel better in the short term. Moreover, in the long term their HA1c remains high and their long-term health suffers. Thus, the patients may feel that their treatment is not working and they may lose interest in the therapy or discontinue treatment.

Due to the almost peakless profile basal insulin and insulin glargine are simple to titrate. Meanwhile, there is an array of approaches that physicians use for titration. Some of these approaches are e.g. described in Anthony Barnet, "Dosing of Insulin Glargine in the Treatment of Type 2 Diabetes", Clinical Therapeutics, vol. 29, no. 6, 2007, pages 987-999; Melanie Davies et al., "Improvement of Glycemic Control in Subjects With Poorly Controlled Type 2 Diabetes", Diabetes Care, vol. 28, no. 6, June 2005, pages 1282-1288; H. C. Gerstein et al., "A randomized trial of adding insulin glargine vs. avoidance of insulin in people with Type 2 diabetes on either no oral glucose-lowering agents or submaximal doses of metformin and/or sulphonylureas, The Canadian INSIGHT (Implementing New Strategies with Insulin Glargine for Hyperglycaemia Treatment) Study", Diabetic Medicine, vol. 23, 2006, pages 736-742; H. Yki-Järvinen et al., "Insulin glargine or NPH combined with metformin in type 2 diabetes: he LANMET Study", Diabetologica; Robert J. Heine et al., "Exenatide versus Insulin Glargine in Patients with Suboptimally Controlled Type 2 Diabetes, A Randomized Trial", Annals of Internal Medicine, vol. 143, no. 8, October 2005, pages 559-569 and Poul Strange, "Treat-to-Target Insulin Titration Algorithms When Initiating Long or Intermediate Acting Insulin in Type 2 Diabetes", Journal of Diabetes Science and Technology, vol. 1, issue 4, July 2007, pages 540-548.

Generally, these approaches suggest a specific dose adjustment within a specific time period until the target FBG is achieved. Each of these algorithms comes with specific rules, e.g. that the dose should not be increased if the blood glucose value (BG value) was below 70 mg/dl (low blood sugar) in the last week. Furthermore, health care professionals may set a different FBG target to suit the patient.

Independently of the above referenced publications EP 1 281 351 A2 describes a diabetes management system which enables glycemic control for a subject. The described system includes an insulin delivery unit, a glucose sensor and a control unit. The control unit includes a processor unit that receives glucose value readings from the glucose sensor, executes an algorithm that predicts a glucose value at a predetermined time in the future, compares the predicted glucose value with the predetermined glucose value range, and determines a corrective amount of insulin to be administered when the predicted glucose value lies outside of the predetermined glucose value range. The glucose unit also includes a communication unit that transmits the corrective amount to the delivery unit.

SUMMARY OF THE INVENTION

It is an object of the invention to provide a medical device for providing information for glycemic control and the respective method thereof, which provides the flexibility so that it can be customized for each patient/user.

Furthermore, it is an aspect of the invention to allow a convenient configuration of the medical device for the target values needed for the user.

Moreover, it is an aspect of the invention to provide a method for determining a dose of insulin to be set for glycemic control and a respective device which offers an improved glycemic control.

Additionally, it is a further aspect to provide a medical device for providing information for glycemic control and the respective method thereof, which is able to provide an improved carbohydrate calculation for the dose to be administered.

This object and the further aspects are solved by the subject matter of the independent claims. Preferred embodiments are the subject matter of the dependent claims.

One aspect of the present invention is to provide a medical device for providing information for glycemic control. The device comprises storage means arranged to store data, receiving means arranged to receive blood glucose value data and security data, data processing means arranged to execute a first processing function for modifying data retrieved from the storage means and to execute a second processing function for providing information for glycemic control based on the blood glucose value data and data retrieved from the storage means, validating means arranged to validate the received security data and to provide validation data corresponding to the validation of the received security data, and safety means arranged to control an execution of at least a predetermined function out of the first and second processing functions based on the validation data.

In a preferred embodiment the medical device further comprises blood glucose measurement means arranged for measuring a blood glucose value and to provide blood glucose value data corresponding to the measured blood glucose value, wherein the receiving means are further arranged to receive the blood glucose value data from the blood glucose measurement means. The medical device further comprises dose setting means arranged to set a dose of insulin based on the information for glycemic control.

Preferably, the information for glycemic control is a value for a dose of insulin to be set, the second processing function is a processing function for determining the value for the dose of insulin to be set, and the control of the execution of at least the predetermined function out of the first and second processing functions based on the validation data is arranged by unlocking the predetermined function for execution. Moreover, preferably the security data is a password or an activation key and wherein the validating means are further arranged to validate the password or the activation key based on predefined data stored in the storage means or in the validating means.

The medical device preferably further comprises a user interface, a USB interface, an IEEE 1394 interface or a wireless interface adapted to receive the security data, wherein the storage means is further arranged to store profile parameters for different dose adjustment profiles, wherein the first processing function is a processing function for adjusting the profile parameters for a selected dose adjustment profile and wherein the second processing function is a processing function for stepwise adapting a dose of insulin based at least on the selected dose adjustment profile and thereby determining the value for the dose of insulin to be set.

Preferably, the first processing function is a processing function for selecting a specific initial dose value from a predefined set of initial dose values, a specific first dose increase step from a predefined set of first dose increase steps, a specific first time interval for increasing the dose from a predefined set of first time intervals, a specific first target blood glucose value from a predefined set of first target blood glucose values, a specific second dose increase step from a predefined set of second dose increase steps, a specific second time interval for increasing the dose from a predefined set of second time intervals, a specific second target blood glucose value from a predefined set of second target blood glucose values, a specific low blood glucose threshold value from a predefined set of low blood glucose threshold values, a specific low blood glucose dose decrease step from a predefined set of low blood glucose dose decrease steps, a specific hypoglycemic blood glucose threshold value from a predefined set of hypoglycemic blood glucose threshold values, a specific hypoglycemic blood glucose dose decrease step from a predefined set of hypoglycemic blood glucose dose decrease steps, and for storing the selected data in the storage means.

Furthermore, preferably the data processing means are further arranged to execute further first processing functions for modifying data retrieved from the storage means and to execute further second processing functions for providing information for glycemic control based on the blood glucose value data and data retrieved from the storage means.

Another aspect of the present invention is to provide a medical system for providing glycemic control. The system comprises first storage means arranged to store data, first data processing means arranged to execute a first processing function for modifying data retrieved from the first storage means, second storage means arranged to store data, blood glucose measurement means arranged for measuring a blood glucose value and to provide blood glucose value data corresponding to the measured blood glucose value, second data processing means arranged to execute a second processing function for providing information for glycemic control based on the blood glucose value data and data retrieved from the second storage means, transmitting means arranged to transmit data stored in the first storage means and security data, receiving means arranged to receive the transmitted data, validating means arranged to validate the received security data and to provide validation data corresponding to the validation of the received security data, and safety means arranged to control an execution of the second processing function.

In a preferred embodiment the medical device further comprises dose setting means arranged to set a dose of insulin based on the information for glycemic control, wherein the first storage means, the first data processing means and the transmitting means form a first functional unit and the second storage means, the blood glucose measurement means, the second data processing means, the receiving means the validating means and the safety means form a second functional unit.

A further aspect of the present invention is to provide a method for providing information for glycemic control. The method comprises the steps of receiving security data, validating the received security data, providing validation data corresponding to the validation of the received security data, and controlling an execution of at least a predetermined function out of at least one first and at least one second processing function based on the validation data, wherein the at least one first processing function is for modifying data retrieved from storage means and the at least one the second processing function for providing information for glycemic control based on received blood glucose value data and data retrieved from the storage means.

In further aspect of the present invention, a computer program, a computer program product and a computer readable medium is disclosed for providing information for glycemic control. The computer program comprises code for receiving security data, code for validating the received security data, code for providing validation data corresponding to the validation of the received security data, and code for controlling an execution of at least a predetermined function out of at least one first and at least one second processing function based on the validation data, wherein the at least one first processing function is for modifying data retrieved from a storage means and the at least one the second processing function for providing information for glycemic control based on received blood glucose value data and data retrieved from the storage means.

In a preferred embodiment the method and computer program further comprise measuring a blood glucose value and providing the blood glucose value data corresponding to the measured blood glucose value.

Moreover, the method and computer program preferably further comprise setting a dose of insulin based on the information for glycemic control. Preferably, the information for glycemic control is a value for a dose of insulin to be set, one of the second processing functions is a processing function for determining the value for the dose of insulin to be set, and the control of the execution of at least the predetermined function out of the first and second processing functions based on the validation data is arranged by unlocking the predetermined function for execution.

Furthermore, preferably the security data is a password or an activation key and wherein the validating step comprises validating the password or the activation key based on predefined stored data.

The method and computer program preferably further comprise storing profile parameters for different dose adjustment profiles, wherein one of the first processing functions is a processing function for adjusting the profile parameters for a selected dose adjustment profile and wherein one of the second processing functions is a processing function for stepwise adapting a dose on insulin based at least on the selected dose adjustment profile wherein one of the first processing functions is a processing function for selecting a specific initial dose value from a predefined set of initial dose values, a specific first dose increase step from a predefined set of first dose increase steps, a specific first time interval for increasing the dose from a predefined set of first time intervals, a specific first target blood glucose value from a predefined set of first target blood glucose values, a specific second dose increase step from a predefined set of second dose increase steps, a specific second time interval for increasing the dose from a predefined set of second time intervals, a specific second target blood glucose value from a predefined set of second target blood glucose values, a specific low blood glucose threshold value from a predefined set of low blood glucose threshold values, a specific low blood glucose dose decrease step from a predefined set of low blood glucose dose decrease steps, a specific hypoglycemic blood glucose threshold value from a predefined set of hypoglycemic blood glucose threshold values, a specific hypoglycemic blood glucose dose decrease step from a predefined set of hypoglycemic blood glucose dose decrease steps, and for storing the selected data in the storage means.

Still a further aspect of the present invention is to provide a method for configuring a process for determining a dose of insulin to be administered for glycemic control, wherein the dose is stepwise adapted. The method comprises the steps of defining different dose adjustment profiles for stepwise adapting the dose, wherein each of the different dose adjustment profiles is based at least on a specific initial dose value, a specific time interval for increasing the dose, a specific dose increase step and a specific low blood glucose threshold value, storing the different dose adjustment profiles, selecting one of the stored different dose adjustment profiles based on specific requirements for stepwise adapting the dose, and personalizing the selected dose adjustment profile by defining at least a specific target blood glucose value for a specific user.

In a preferred embodiment, the specific requirements are defined by a type of a diabetes patient and the personalizing step comprises identifying the user of the selected dose adjustment profile. Furthermore, the different dose adjustment profiles are defined by selecting the specific initial dose value from a predefined set of initial dose values, the specific time interval for increasing the dose from a predefined set of time intervals, the specific dose increase step from a predefined set of dose increase steps and the specific low blood glucose threshold value from a predefined set of low blood glucose threshold values.

The method preferably further comprises the step of defining plausibility rules which define predetermined combinations for selectable initial dose values, low blood glucose threshold values, time intervals and dose increase steps, and the step of protecting the defined different dose adjustment profiles from unauthorized changes, wherein the protecting step comprises receiving security data, validating the received security data, providing validation data corresponding to the validation of the received security data, and controlling the defining step based on the validation data.

Preferably, the different dose adjustment profiles are defined on a data processing unit and the defined different dose adjustment profiles are transmitted to a device for determining a dose of insulin to be administered for glycemic control.

According to another preferred embodiment a system for configuring a process for determining a dose of insulin to be administered for glycemic control, wherein the dose is stepwise adapted. The system comprises defining means arranged to define different dose adjustment profiles for stepwise adapting the dose, wherein each of the different dose adjustment profiles is based at least on a specific initial dose value, a specific time interval for increasing the dose, a specific dose increase step and a specific low blood glucose threshold value, a storing unit arranged to store the different dose adjustment profiles, selection means arranged to select one of the stored different dose adjustment profiles based on specific requirements for stepwise adapting the dose, personalizing means arranged to personalize the selected dose adjustment profile by defining at least a specific target blood glucose value for a specific user, and adapting means arranged to stepwise adapt the dose according to the selected dose adjustment profile.

Preferably, the specific requirements are defined by a diabetes type and an age of a diabetes patient, wherein the personalizing means are further arranged to identify the user of the selected dose adjustment profile.

Furthermore, preferably the defining means are further arranged to provide a predefined set of initial dose values, a predefined set of target blood glucose values, a predefined set of low blood glucose threshold values, a predefined set of time intervals and a predefined set of dose increases and to select the specific initial dose value from the predefined set of initial dose values, the specific target blood glucose value from the predefined set of target blood glucose values, the specific low blood glucose threshold value from the predefined set of low blood glucose threshold values, the specific time interval for increasing the dose from the predefined set of time intervals and the specific dose increase step from the predefined set of dose increase steps.

In the preferred embodiment the defining means are further arranged to define plausibility rules which define predetermined combinations for selectable initial dose values, target blood glucose values, low blood glucose threshold values, time intervals and dose increases. The system preferably further comprises a protection unit arranged to protect the defined different dose adjustment profiles from unauthorized changes, wherein the protection unit comprises receiving means arranged to receive security data, validating means arranged to validate the received security data and to provide validation data corresponding to the validation of the received security data, and safety means arranged to control the defining means based on the validation data.

Preferably, the system consists of at least a data processing unit and a device for determining a dose of insulin to be administered for glycemic control, wherein the data processing unit comprises the defining means and data transmission means arranged for transmitting the defined different dose adjustment profiles to the device for determining a dose of insulin, and wherein the device for determining a dose of insulin comprises receiving means arranged for receiving the defined different dose adjustment profiles, the storing unit, the selection means and the adapting means.

Yet another aspect of the present invention is to provide a method for determining a dose of insulin to be administered for glycemic control, wherein the dose is stepwise adapted. The method comprises the steps of receiving glycemic event information in respect to a predetermined glycemic event, wherein the predetermined glycemic event occurred within a predetermined time interval, receiving a range information indicating that at least one specific blood glucose value is within a specific range in respect to a target blood glucose value, and determining based on at least said glycemic event information and said range information, to terminate increasing the dose according to at least one parameter.

According to a preferred embodiment of the method the glycemic event information is a user input indicating that a hypoglycemic event happened within the predetermined time interval.

Preferably, the method further comprises the step of determining a blood glucose value, wherein the at least one specific blood glucose value is the determined blood glucose value. Preferably, the at least one specific blood glucose value is a blood glucose value preceding the determined blood glucose value.

The preferred embodiment of the method further comprises the steps of receiving a low blood glucose threshold value, and reducing the dose by a predetermined amount if the actually determined blood glucose value is below the low blood glucose threshold value. Preferably, the determined blood glucose value is a fasting blood glucose value. Moreover, the range information preferably represents information that the at least one specific blood glucose value is equal or below a specific threshold value and above or equal to the target blood glucose value, wherein the range information is represented by Boolean values yes or no.

Moreover, the method preferably comprises the step of indicating that the increasing of the dose has been terminated based on at least said glycemic event information and said range information and the step of storing at least one determined blood glucose value in relation with date and time when the blood glucose value is determined, wherein the step of storing further comprises storing an adapted dose in relation with adapting date and time.

The preferred embodiment of the method further comprises the step of storing termination data in relation to a dose administered previous to the termination, wherein the termination data indicate that the increasing of the dose has been terminated.

According to a further preferred embodiment a device for determining a dose of insulin to be administered for glycemic control is provided. The device comprises a receiving unit arranged to receive a glycemic event information in respect to a predetermined glycemic event within a predetermined time interval and for receiving a range information indicating that at least one specific blood glucose value is within a specific range in respect to a target blood glucose value, a determining unit arranged to determine, based on at least said glycemic event information and said range information, to terminate increasing the dose according to at least one parameter, and adapting means arranged to stepwise adapting the dose according to the output of the receiving unit and the determining unit.

Preferably, the device further comprises a user input unit arranged to receive a user input indicating that a hypoglycemic event happened within the predetermined time interval and to forward this information as the glycemic event information to the determining unit, wherein the user input unit is further arranged to receive a low blood glucose threshold value and the adapting means are further arranged to reduce the dose by a predetermined amount if the actual blood glucose value is below the low blood glucose threshold value.

The device according to the preferred embodiment further comprises a measurement unit arranged to measure an actual blood glucose value, and a storage unit arranged to store at least one measured blood glucose value in relation with date and time of a respective blood glucose measurement, wherein the storage unit is further arranged to store an adapted dose in relation with adapting date and time and to store termination data in relation to a dose administered previous to the termination, wherein the termination data indicate that the increasing of the dose has been terminated.

Still a further aspect of the present invention is to provide a method for determining a dose of insulin to be administered for glycemic control, wherein the dose is stepwise adapted. the method comprises the steps of determining a blood glucose value, receiving glycemic event information in respect to a predetermined glycemic event, wherein the predetermined glycemic event occurred within a predetermined time interval, receiving a previously adapted dose value stored in a storage unit, and setting an alert based on at least the blood glucose value, the glycemic event information and the previously adapted dose, wherein the alert indicates that the blood glucose value and the predetermined glycemic event are not in a specified relation to the previously adapted dose value.

In a preferred embodiment the method further comprises the step of defining the specified relation between the blood glucose value and the predetermined glycemic event and the previously adapted dose value by providing at least one specific blood glucose value range and at least one specific predetermined glycemic event, both corresponding to at least one specific dose value, and the step of stopping to further increase the dose, wherein the stopping of the further increase of the dose is triggered by the alert, and wherein a predetermined user input is needed to deactivate the stopping of the further increase of the dose.

Preferably, the method further comprises the step of creating retest information, wherein the creating of the retest information is triggered by the alert and the retest information is for initiating a retest of the blood glucose value within a predetermined time, and the step of displaying a message on a display indicating that the alert occurred, wherein the message comprises at least predefined safety instructions, wherein the retest information is displayed on the display for prompting a user to retest the blood glucose value within the predetermined time.

Furthermore, the method according to the preferred embodiment further comprises the step of sending an additional message to a predetermined destination, wherein the sending of the additional message is triggered by the alert, and wherein the additional message comprises at least information indicating that the blood glucose value and the predetermined glycemic event are not in a specified relation to the previously adapted dose value.

According to another preferred embodiment a device for determining a dose of insulin to be administered for glycemic control is provided. The device comprises a blood glucose determining unit adapted to determine at least a blood glucose value, a storage unit adapted to store a previously adapted dose value, a receiving unit arranged to receive a glycemic event information in respect to a predetermined glycemic event within a predetermined time interval and for receiving the previously adapted dose value stored in a storage unit, adapting means arranged to stepwise adapting the dose according to the output of the receiving unit and the determining unit, and an alert unit adapted to set an alert based on at least the blood glucose value, the glycemic event information and the previously adapted dose, wherein the alert unit is adapted to create the alert indicating that the blood glucose value and the predetermined glycemic event are not in a specified relation to the previously adapted dose value.

The device according to the preferred embodiment further comprises a user interface adapted to receive instructions for defining the specified relation between the blood glucose value and the predetermined glycemic event and the previously adapted dose value by providing at least one specific blood glucose value range and at least one specific predetermined glycemic event both corresponding to at least one specific dose value, wherein the storage unit is further adapted to store the at least one specific blood glucose value range and the at least one specific predetermined glycemic event.

Preferably, the device further comprises a determining unit arranged to determine to stop the further increase of the dose based on the alert and arranged to receive a predetermined user input via the user interface for deactivating the stopping of the further increase of the dose, a message generation unit arranged to create retest information, wherein message generation unit is arranged to receive an alert signal from the alert unit and to generate the retest information for initiating a retest of the blood glucose value within a predetermined time, and a display unit arranged to display a message indicating that the alert occurred, wherein the message generation unit is further arranged to create a message comprising at least predefined safety instructions, wherein the display unit is further arranged to display the retest information for prompting a user to retest the blood glucose value within the predetermined time.

Preferably, the message generation unit further comprises a communication interface adapted to transmit an additional message to a predetermined destination, wherein the communication interface is arranged to transmit the additional message triggered by the alert, and wherein the message generation unit is further arranged to create the additional message comprising at least information indicating that the blood glucose value and the predetermined glycemic event are not in a specified relation to the previously adapted dose value.

Still a further aspect of the present invention is to provide a medical device for providing information for glycemic control. The device comprises a storage unit arranged to store information on an initial dose of insulin and to store information on a blood glucose level measured after the initial dose of insulin was administered and after specific food was consumed, and a determining unit arranged to determine a subsequent dose of insulin to be administered before the specific food is consumed based at least on said information on the initial dose of insulin and said information on the blood glucose level.

According to a preferred embodiment of the device, the storage unit is further arranged to store information on the specific food consumed, wherein the information on specific food consumed comprises data relevant for the glycemic control. Moreover, the device preferably further comprises a user input unit arranged to receive the information on the specific food consumed, wherein the storage unit is further arranged to store information on time elapsed between administration of the predetermined dose of insulin, consumption of the specific food and measurement of the blood glucose level.

Preferably, the determining unit is further arranged to calculate the initial dose of insulin only based on the information on the specific food consumed, and wherein the information on the blood glucose level is a measured blood glucose value. Furthermore, the determining unit is preferably further arranged to determine for each specific food a specific adjustment value for the subsequent dose of insulin based at least on the information on the specific food consumed, the initial dose of insulin calculated for the specific food and a deviation of the measured blood glucose value from a predefined blood glucose value.

In the preferred embodiment of the device the determining unit is further arranged to determine the specific adjustment value additionally based on information on a blood glucose level measured before the specific food was consumed and based on the time elapsed between administration of the predetermined dose of insulin, consumption of the specific food and measurement of the blood glucose level after the consumption. Preferably, the determining unit is further arranged to determine the subsequent dose of insulin additionally based on information on an additional predetermined dose of long-acting basal insulin administered.

According to a further preferred embodiment a method for providing information for glycemic control is provided. The method comprising the steps of storing information on an initial dose of insulin and information on a blood glucose level measured after the initial dose of insulin was administered and after specific food was consumed, and determining a subsequent dose of insulin to be administered before the specific food is consumed based at least on said information on the initial dose of insulin and said information on the blood glucose level.

The preferred embodiment of the method further comprises the step of storing information on the specific food consumed, wherein the information on specific food consumed comprises data relevant for the glycemic control, and the step of storing information on time elapsed between administration of the predetermined dose of insulin, consumption of the specific food and measurement of the blood glucose level.

Preferably, the method further comprises the step of calculating the initial dose of insulin only based on the information on the specific food consumed, wherein the information on the blood glucose level is a measured blood glucose value.

The method preferably also comprises the step of determining for each specific food a specific adjustment value for the subsequent dose of insulin based at least on the information on the specific food consumed, the initial dose of insulin calculated for the specific food and a deviation of the measured blood glucose value from a predefined blood glucose value. Preferably, the subsequent dose of insulin is additionally determined based on information on an additional predetermined dose of long-acting basal insulin administered.

Yet another aspect of the present invention is to provide a medical device for determining a dose of insulin to be administered for glycemic control. The medical device comprises a blood glucose measurement unit arranged to measure at least one blood glucose value before and at least one blood glucose value after every meal of a day, a determining unit arranged to determine for each meal a difference between a respective blood glucose value measured before the respective meal and the respective blood glucose value measured after the respective meal, and arranged to determine the meal with the biggest difference, and adapting means arranged to determine the dose for the determined meal.

According to a further preferred embodiment a method for determining a dose of insulin to be administered for glycemic control is provided. The method comprises the steps of measuring at least one blood glucose value before and at least one blood glucose value after every meal of a day, determining for each meal a difference between a respective blood glucose value measured before the respective meal and the respective blood glucose value measured after the respective meal, determining the meal with the biggest difference, and adapting the dose for the determined meal.

BRIEF DESCRIPTION OF THE DRAWINGS

Further advantages and preferred embodiments are included in the dependent claims and will be better understood from the below description of preferred embodiments, with reference to the accompanying drawings, in which

DETAILED DESCRIPTION OF THE INVENTION

The following paragraphs will describe various embodiments of the invention. For exemplary purpose only, most of the embodiments are outlined in relation to a medical device or system and the respective method. However, the used terminology and the description of the embodiments with respect to the medical device and system are not intended to limit the principles and ideas of the invention to such a single device or system. For example, the invention is also applicable to a distributed system of components which communicate with each other via a wired or a wireless network.

Also, the detailed explanations given in the background of the invention section above are merely intended to better understand the constraints of an insulin treatment or a treatment with other hormones. Furthermore, the titration methods described herein can be applied to basal, premixed and mealtime insulin. In the following, the term insulin is used for all kinds of insulin and glargine unless otherwise stated.

Figure 1:
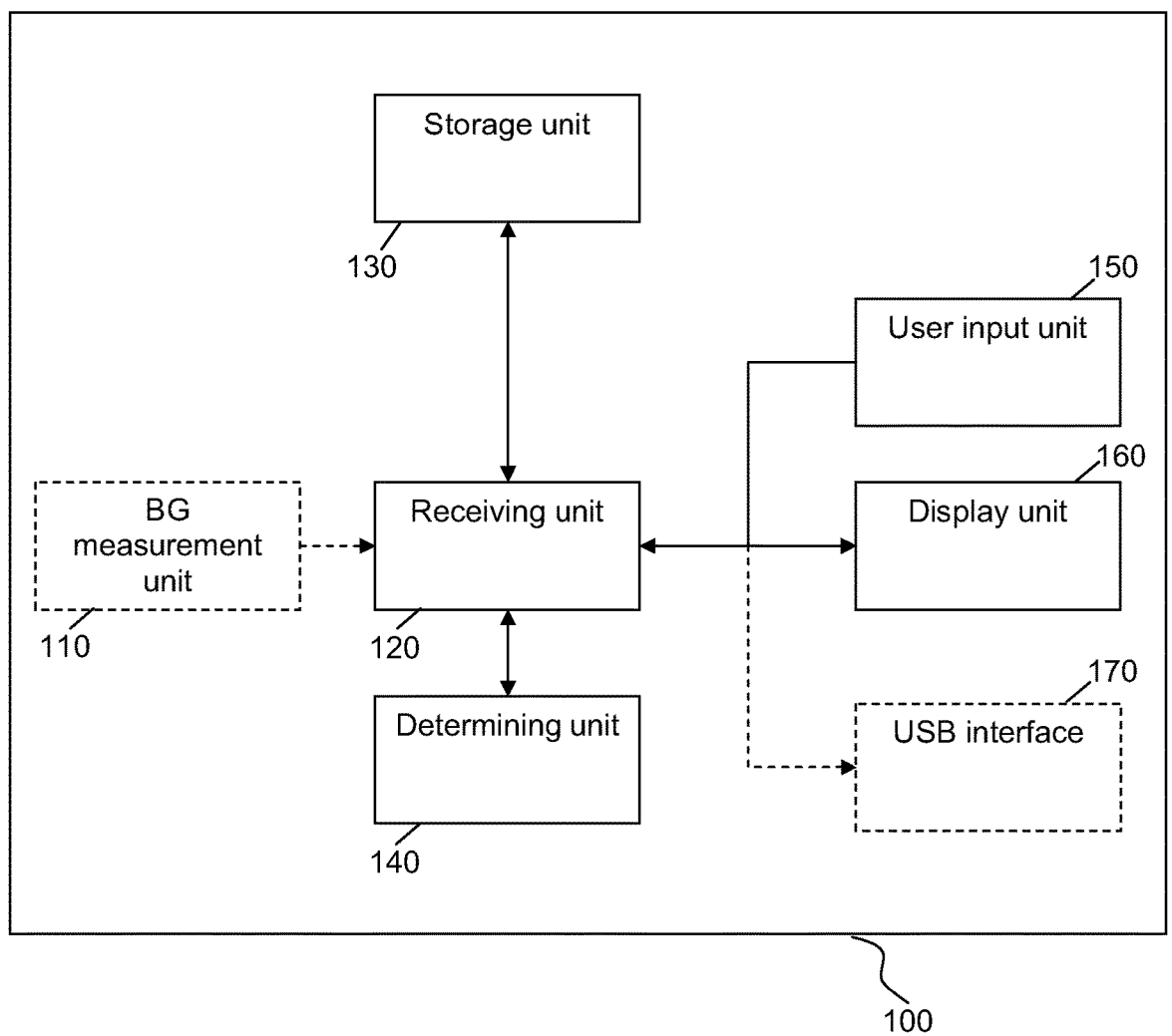
FIG. 1 is a schematic diagram of the medical device according to a preferred embodiment of the invention.

FIG. 1 is a schematic diagram of the medical device according to a preferred embodiment of the invention. Preferably, the medical device 100 comprises a blood glucose measurement unit 110, which is arranged to measure the blood glucose level e.g. of the user of the medical device. The blood glucose measurement unit 110 is connected to a receiving unit 120, which is arranged to forward e.g. blood glucose value data received from blood glucose measurement unit 110 to the storage unit 130. Alternatively, the receiving unit may retrieve stored data such as e.g. blood glucose value data from the storage unit and forward it to the determining unit 140. Alternatively, the receiving unit 120 directly forwards the blood glucose value data received from the blood glucose measurement unit 110 to a determining unit 140.

Receiving unit 120 is further connected to user input unit 150. The user input unit 150 is arranged to receive input from the user of the medical device 100. The user input data are forwarded from the user input unit 150 to the receiving unit 120, which either forwards it to the determining unit 140 or to the storage unit 130.

Furthermore, the medical device 100 preferably comprises a display unit 160, which is connected to the receiving unit 120. Preferably, the display unit 160 receives data to be displayed from the receiving unit 120. Preferably, the medical device 100 additionally comprises a further interface 170, such as a USB interface, an IRDA interface, Bluetooth interface, etc., in order to receive data and to transmit data. The interface 170 is preferably connected to the receiving unit 120 in order to receive data from the receiving unit 120 and to forward data to the receiving unit 120.

As outlined above, the medical device 100 preferably comprises a blood glucose measurement unit 110. Preferably, the blood glucose measurement unit 110 is arranged to measure the blood glucose level in the blood of e.g. the user by testing a drop of blood on a respective test strip. The measured blood glucose value is then transformed to blood glucose value data and forwarded preferably immediately or on demand to the receiving unit 120. Alternatively, the blood glucose measurement unit 110 is arranged to measure the blood glucose level of e.g. the user via infrared diagnosis or an alternative contactless measurement method.

According to a further alternative the blood glucose measurement unit 110 is implanted in the body of the user of the medical device 100 and forwards the data to the receiving unit 120 either via a wired connection or via a wireless connection. Preferably, such an implanted blood glucose measurement unit 110 is a continuous measurement sensor e.g. based on a bio chip which allows a continuous closed loop control. In the latter case the blood glucose measurement unit 110 preferably forwards the blood glucose measurement value data to the receiving unit 120 via interface 170. According to a further alternative the medical device 100 does not comprise a blood glucose measurement unit 110 which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated based on user input which is received via user input unit 150. Alternatively, the trigger signal is generated automatically by a timer unit or by determining unit 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120 data are retrieved from the storage unit 130 on demand and forwarded to the determining unit 140, to the display unit 160 or to the interface 170. Moreover, the receiving unit 120 forwards control signals, such as trigger signals or control signals e.g. to the blood glucose measurement unit 110, the display unit 160 or the interface 170.

The storage unit 130 is arranged to store data input via the user input unit 150, data received by the blood glucose measurement unit 110, data processed by the determining unit 140 and/or data received via interface 170. Furthermore, storage unit 130 is arranged to provide the stored data to the determining unit 140, to the display unit 160 and/or to the interface 170. The storage unit 130 is preferably implemented as a semiconductor memory. Alternatively, it is implemented as a hard disk memory or an on-chip memory of the determining unit 140.

The determining unit 140 is preferably a microprocessor or any other functional unit capable of processing data. The user input unit 150 is preferably implemented as one or more push buttons or alternatively as so called soft keys wherein the function of the respective soft key is displayed on the display unit 160. Alternatively, the user input unit 150 is a key board or a touch screen. Alternatively, the user input unit 150 comprises a microphone for receiving speech input so that data can be entered via speech input.

The display unit 160 preferably comprises an LCD or LED display. Preferably, the display can display a number of alphanumerical characters so that e.g. the actual measured blood glucose value can be displayed together with additional instructions for the user. Alternatively, the display unit 160 comprises a graphic display in order to display graphs or graphics.

The interface 170 is preferably a wireless interface, such as IRDA, Bluetooth, GSM, UMTS, ZigBee, or WI-FI, etc. Alternatively, the interface is a wired interface, such as a USB port, serial port, parallel port, network card, etc., for receiving and transmitting data. In a further alternative the medical device 100 does not comprise an interface 170.

According to another alternative medical device 100 comprises additionally to the interface 170 a chip-card reader or a chip-card reader interface. The chip-card reader is preferably adapted to read a chip card, such as a SIM card or a chip card with information. For this, the chip card comprises a memory, wherein preferably a selected algorithm together with corresponding parameters and a history of the blood glucose values and doses administered, etc. is stored. Thus, in the case that the medical device 100 has a defect, the relevant data can be easily removed from the medical device 100 via the chip card and transferred to a new medical device 100. Moreover, the chip card 100 may be used in order to provide information on the history of the treatment to e.g. an HCP.

In the case that a SIM card is used together with the chip-card reader of the medical device 100 and the interface unit 170 is additionally a mobile communication interface, the basic functions of the medical device 100 can be unlocked by the provider of the SIM card via a telecommunication channel. This additionally offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via administration unit 2000 by addressing the mobile communication unit e.g. with a phone number.

Furthermore, the medical device 100 is able to transmit data via SMS, e-mail or via mobile Internet connection. Moreover, this offers the possibility to locate the medical device 100 in an emergency case.

Figure 2:
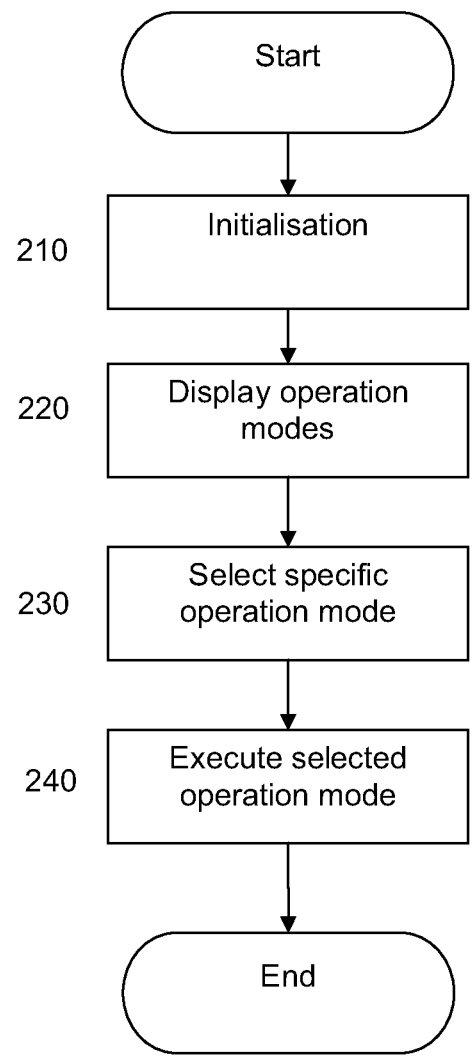
FIG. 2 is a flow diagram illustrating steps of operation of the medical device according to a preferred embodiment of the invention.

As shown in FIG. 2, the medical device 100 is preferably capable to perform a number of operating processes. According to a preferred alternative after switching on, the medical device 100 performs initialization step 210 for initializing the functional components of the medical device 100. After this, the different operation modes of which the medical device 100 is capable, are displayed in the display step 220. Preferably, modes such as "Measure BG", "Output insulin dose", "Mark event", "Review history" and/or "Change settings" can be selected in step 220. In step 230 the user selects one of the displayed operation modes via the user input unit 150. In step 240 the selected operation mode is executed.

According to an alternative version of the operation process steps 220 and 230 may be skipped in the case that a specific operation mode is preselected. In that case, after initialization 210, the preselected operation mode, which is either preselected by the user or automatically selected in accordance with a specific event, the operating process proceeds with step 240 and executes the preselected one or more operation modes.

Depending on the operation mode, the operation process may continue after the execution of the selected mode with step 220 in order to give the user of the medical device 100 the option to choose a further operation mode or the operation process ends. In the latter case the medical device 100 is preferably switched off automatically.

Figure 3:
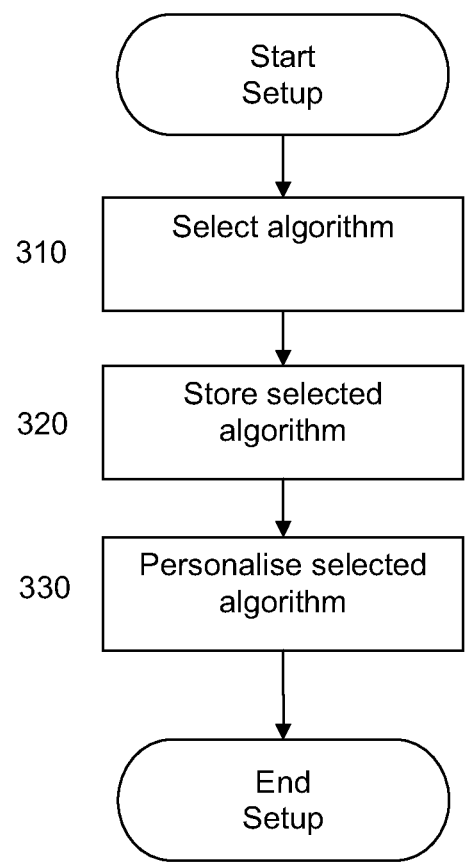
FIG. 3 is a flow diagram illustrating steps of a further operating procedure of the medical device according to a preferred embodiment of the invention.

One specific operation mode is the set up mode, which is also called change setting mode. FIG. 3 shows a schematic flow diagram of a preferred setup procedure.

As outlined above, the medical device 100 is adapted according to a preferred embodiment of the invention to measure the blood sugar. Furthermore, it is arranged to review the history of the measured blood sugar. Preferably, the medical device 100 displays not only the recent blood glucose value data, but also the insulin dose administered. Moreover, the medical device 100 and in particular the determining unit 140 determine e.g. a dose of insulin to be administered based on specific parameters. Furthermore, the medical device 100 is preferably arranged to receive data either via user input or electronically via interface 170, which indicate specific events. Preferably, these functions or at least some of these functions can be adjusted to the needs of the user of the medical device 100. FIG. 3 shows such a setup procedure for customizing the functions of the medical device 100 to determine the dose to be administered.

As outlined above, a number of algorithms exists on how to determine the dose to be administered based on the FBG value and the dose administered recently. In order to optimize the functionality of the medical device 100, the setup procedure shown in FIG. 3 provides step 310 for selecting an algorithm appropriate for the optimal glycemic control of the user's blood sugar. In step 310 either a predefined algorithm is chosen or a new algorithm is defined. In step 320 the selected predefined or newly defined algorithm is stored or marked with an identifier, such as a flag or pointer, as the selected algorithm. Preferably, in a further step 330 the selected algorithm is further personalized. In the personalizing step 330 specific parameters of the selected algorithm can be further specified and/or selected in relation to the needs and requirements of the user of the medical device 100.

Details of the steps 310 to 330 are explained in more detail further below.

Figure 4:
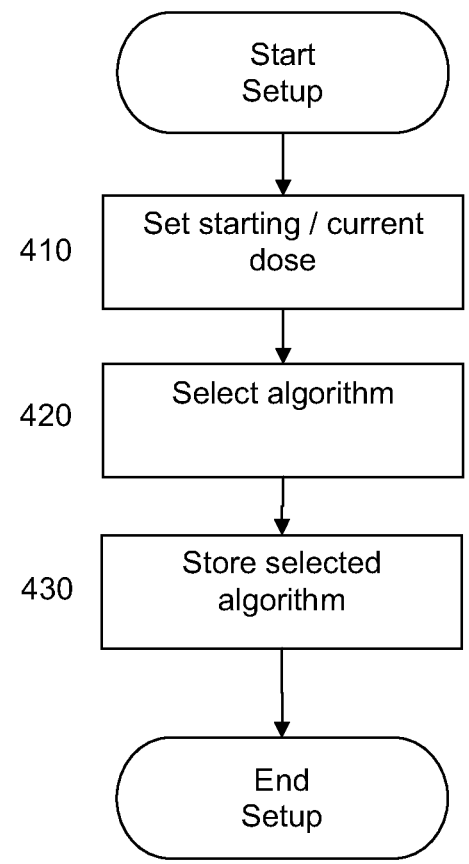
FIG. 4 is a flow diagram illustrating steps of another operating procedure of the medical device according to a preferred embodiment of the invention.

FIG. 4 shows an alternative way for setting up the algorithm for determining the dose to be administered. This alternative setup procedure preferably refers to algorithms, which provide fewer options to be personalized and, thus, provide more parameters, which have been predefined. Accordingly, only few parameters have to be adjusted in order to adapt the function for determining the dose to be administered to the needs and requirements of the user of the medical device 100. As shown in FIG. 4 in the alternative setup procedure, the starting dose or the current dose used by the user is input and stored in step 410. Preferably, the starting dose with which the user-directed titration is started is in the range of 10 to 20 units. Alternatively, in other cases lower or higher values are used. In the case that the user of the medical device 100 already uses a specific dose for obtaining appropriate glycemic control, this dose or a dose equivalent to another insulin type is chosen in step 410 as the current dose. In this case, preferably a safety approach is chosen and the starting dose is determined to be lower dose than the dose equivalent to the other insulin type.

In step 420 a suitable algorithm is chosen and stored in step 430. As outlined before, storing of the selected algorithm does not necessarily require that the selected algorithm is stored additionally in the storage unit 130. Alternatively, the selected algorithm is identified with an identifier such as a pointer or a flag which is stored in the storage unit 130 in relation to the selected algorithm.

Figure 5:
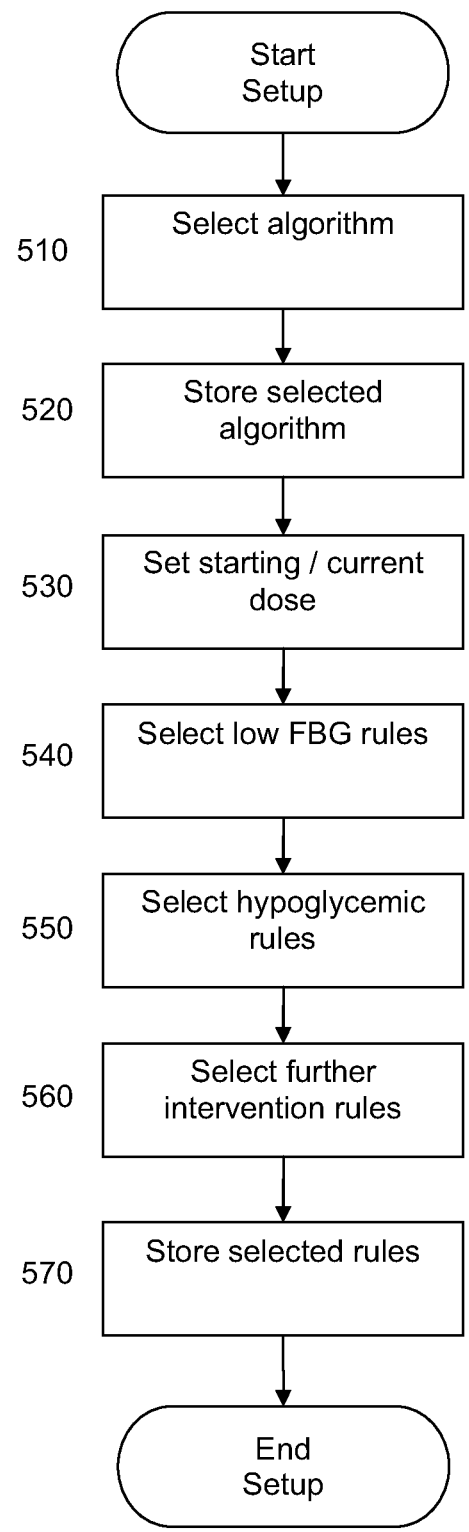
FIG. 5 is a flow diagram illustrating steps of a further operating procedure of the medical device according to a preferred embodiment of the invention.

FIG. 5 shows a further alternative setup procedure, which provides further configuration options for personalizing the process for determining the dose to be administered.

In step 510 an algorithm is chosen which fits best to the needs and requirements of the user of the medical device 100. In step 520 the selected algorithm is stored. Similar to step 410 the current dose or the starting dose for starting the glycemic control process is set in step 530. Furthermore, the setup procedure shown in FIG. 5 provides the option to select specific rules in the case that a blood glucose value and preferably the FBG value is beyond a specific threshold. Preferably, this specific threshold is around 70 mg/dl for a FBG value, which indicates a low blood sugar level. These rules, in the following "low FBG rules", define specific actions, which will be undertaken by the dose determining process if the blood glucose value, and in particular the FBG value, is below the specific threshold. One of theses actions is preferably that the amount of the dose to be administered is not increased for the time being.

In step 550 specific hypoglycemic rules are selected out of a number of predefined hypoglycemic rules. Alternatively, new hypoglycemic rules are defined in step 550. Preferably, hypoglycemic rules define actions, which are undertaken by the dose determining process in the case that the measured blood glucose value is below a further specific threshold. This further specific threshold defines a range, which is also described as a hypoglycemic range. Preferably, hypoglycemic rules are applied in the dose determining process if the blood glucose level is below 56 mg/dl.

Generally, hypoglycemia defines a range below about 70 mg/dl. Thus, the range between about 70 mg/dl to about 56 mg/dl to 50 mg/dl defines a first level of hypoglycemia also called in the following low blood glucose range. The range below about 56 mg/dl to 50 mg/dl defines a second level of hypoglycemia also called in the following hypoglycemic range.

In the case that the blood glucose concentration is lower than this further specific threshold value, a pathologic state is reached, wherein the level of the blood glucose is lower than the normal level. This state, also called hypoglycemia, can produce a variety of symptoms and effects which might be dangerous for the person being in this state. Therefore, the hypoglycemic rules provide actions, which are undertaken by the dose determining process in order to minimize the risk for the user of the medical device 100, in the case that such a low blood glucose value is measured.

Preferably, actions defined via hypoglycemic rules are e.g. to alert the user of the medical device 100, to advise the user of the medical device 100, to contact health care professionals, to decrease the next dose to be administered and/or pause titration for a specific period, etc.

Preferably, in step 560 further intervention rules are defined. Such further intervention rules comprise actions undertaken by the dose determining process, such as safety checks, which check e.g. inappropriate patterns of the development of the blood glucose values in dependence from the doses administered. This preferably includes e.g. the monitoring of events that the dose is increased, but the FBG value does not decrease or even increase. Moreover, these safety checks might also include monitoring a mismatch between the dose manually input by a user and the respective effect on the FBG value. Moreover, these safety checks preferably also include monitoring whether hypoglycemia reoccurs within specific time intervals.

Additional intervention rules according to step 560 are e.g. actions undertaken if a blood glucose value is above a specific threshold, if a symptomatic hypoglycemia occurs, if a specific amount for the dose to be administered is reached, and/or if a final FBG target value or phase target value is reached.

Preferably, specific intervention rules are selected out of a number of predefined selection rules in step 560. In step 570, the rules selected in steps 540 to 560 are stored, preferably in the storing unit 130 and in relation to the selected algorithm.

Figure 6:
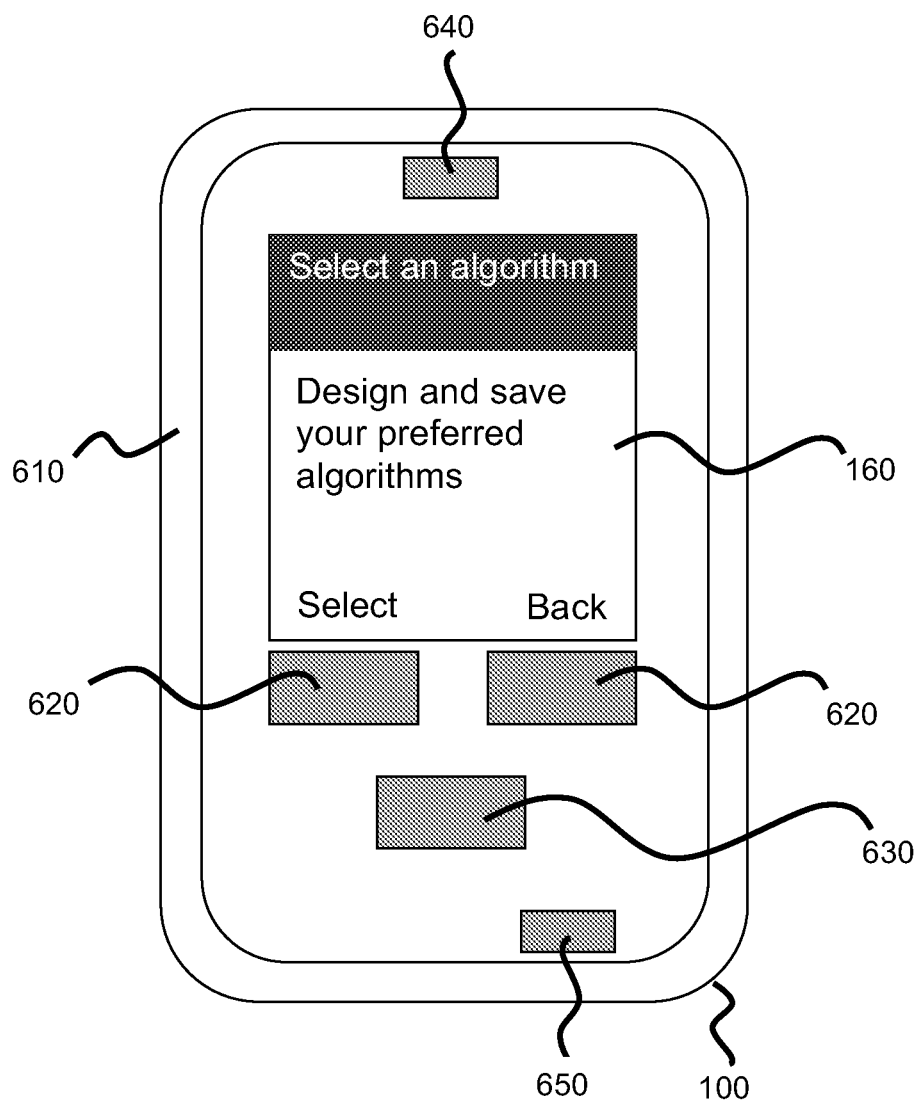
FIG. 6 is another schematic diagram of the medical device shown in FIG. 1.

FIG. 6 shows a further schematic diagram of the medical device 100 according to a preferred embodiment of the invention. In particular, FIG. 6 shows details of the housing and the display of the medical device 100 according to a preferred embodiment of the invention. The medical device 100 comprises housing 610 wherein in the upper side of the housing 610 the display unit 160 is placed. Next to the display unit 160, the housing 610 shows a section wherein soft keys 620 and a navigation key 630 are placed. The soft keys 620 are placed directly next to the display, preferably to the lower left and lower right side of the display. Thus, the display can show the function actually assigned to the soft keys 620.

Preferably, a soft key is a button located alongside the display unit 160. This soft key performs the function dependent on the text shown near it at the moment on the display.

The navigation key 630 is used for scrolling through the menu selections displayed in the display unit 160. Preferably, by pressing the upper part of key 630, one can scroll up the menu selections and by pressing the lower part of key 630, one can scroll to the lower part of the menu selections. Correspondingly, by pressing the left part of key 630, one can scroll to menu selections on the left side and when pressing the right part of key 630, one can scroll to the right part of the menu selections. By pressing the center of the key 630, one can select the chosen menu selection. Alternatively, a navigation pad or a touch screen is used for navigation.

Preferably, medical device 100 comprises a loudspeaker 640 connected to an acoustic module for output acoustic signals such as acoustic alerts or speech. Moreover, the medical device 100 preferably also comprises a microphone 650 for speech input, voice recognition or for communicating via a network connection.

As shown in FIG. 6, the medical device 100 performs the setup procedure wherein a selection can be made between selecting a predetermined algorithm or designing and saving a preferred algorithm.

Figure 7:
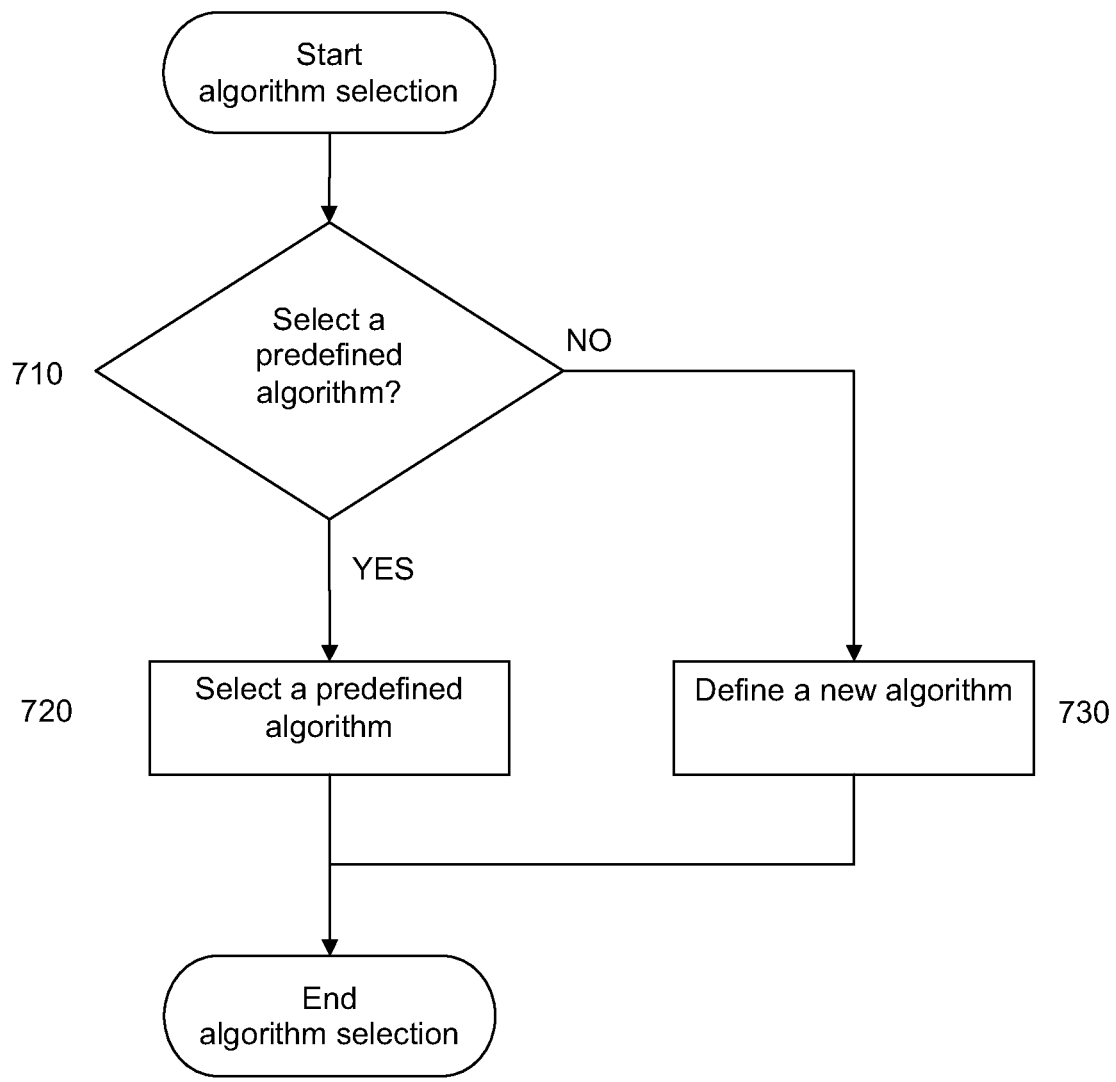
FIG. 7 is a flow diagram illustrating steps of the operating procedure shown in FIG. 3 in further detail.

FIG. 7 shows a flow diagram illustrating the steps of the operating procedure for selecting an algorithm as shown in FIG. 3 in step 310. If it is decided in step 710 of the algorithm selection procedure to select a predefined algorithm, it is proceeded to step 720 in which a predefined algorithm is selected. In the case that it is decided not to select a predefined algorithm, but to define a new algorithm, the method proceeds with step 730. As already explained in regard to FIG. 5, step 720 preferably also includes the selection of low FBG rules, hypoglycemic rules and further intervention rules. The substeps for defining a new algorithm are explained in further detail in regard to FIG. 8.

Figure 8:
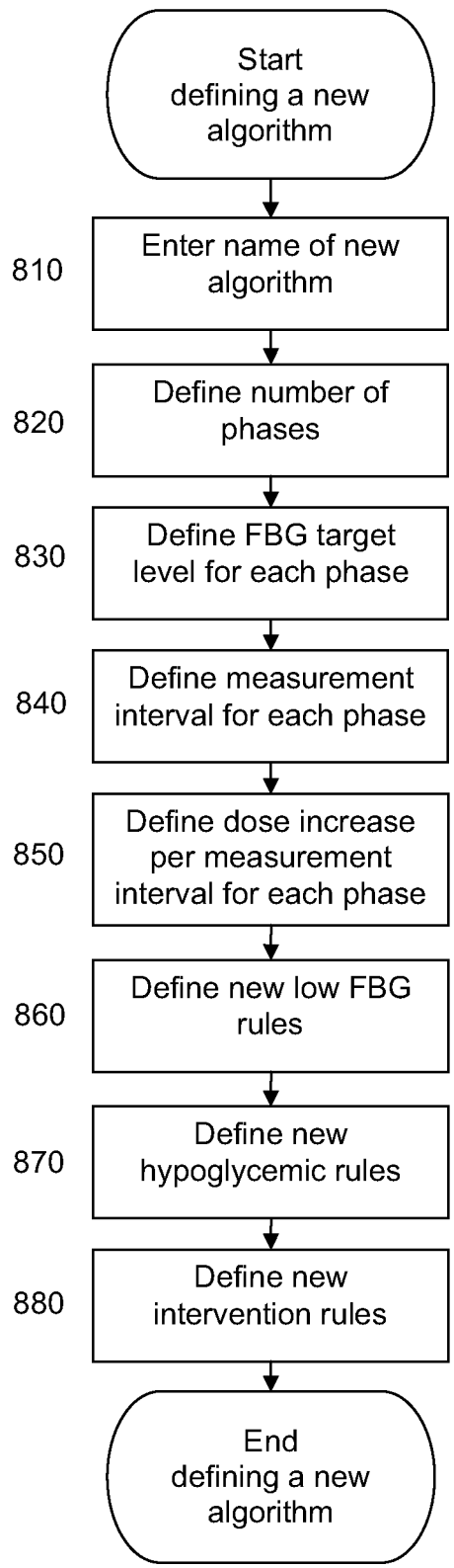
FIG. 8 is a flow diagram illustrating steps of the operating procedure as shown in FIG. 7 in more detail.

FIG. 8 is a flow diagram illustrating substeps of the procedure for defining a new algorithm. As shown in FIG. 8, preferably the procedure for defining a new algorithm starts in step 810 with entering a name for the new algorithm. This may be entered by the user via the user input unit 150. Alternatively, a name for the new algorithm is chosen automatically. Once the name of the new algorithm is defined in step 810, the number of phases of the algorithm is defined in step 820. Preferably, the algorithm is defined by more than one phases. Each phase defines a target which has to be achieved. If this target is achieved, the next phase is initiated. Preferably, each phase is defined by a blood glucose target value or a blood glucose target range to be achieved. Alternatively, only one phase is chosen for the new algorithm.

In step 830, the target level for each phase is defined. Preferably, the target level is a FBG target value defined for each phase. Such a design of the new algorithm allows defining different parameter sets for each phase. Thus, it is possible to define different titration intervals or dose increase steps for the different phases. Such a design of the algorithm allows choosing larger dose increasing steps at the beginning of the self-titration i.e. in a first phase and to decrease the dose increase steps in a subsequent phase when the FBG value is closer to the final FBG target value. In step 840, the measurement interval or titration interval is defined for each phase. The dose increase per measurement interval for each phase is defined in step 850. In step 860, new low FBG rules are defined preferably. Alternatively, predefined low FBG rules can be chosen for the newly defined algorithm. According to another alternative, different low FBG rules are chosen for each of the phases. In the same way new hypoglycemic rules are defined in step 870. Alternatively, predefined hypoglycemic rules are selected for the new algorithm or different hypoglycemic rules are newly defined or selected for each phase. In step 880, new intervention rules are defined. As already outlined for steps 860 and 870 in a further alternative predefined intervention rules are selected or predefined intervention rules or newly defined intervention rules are selected for each phase.

Figure 9:
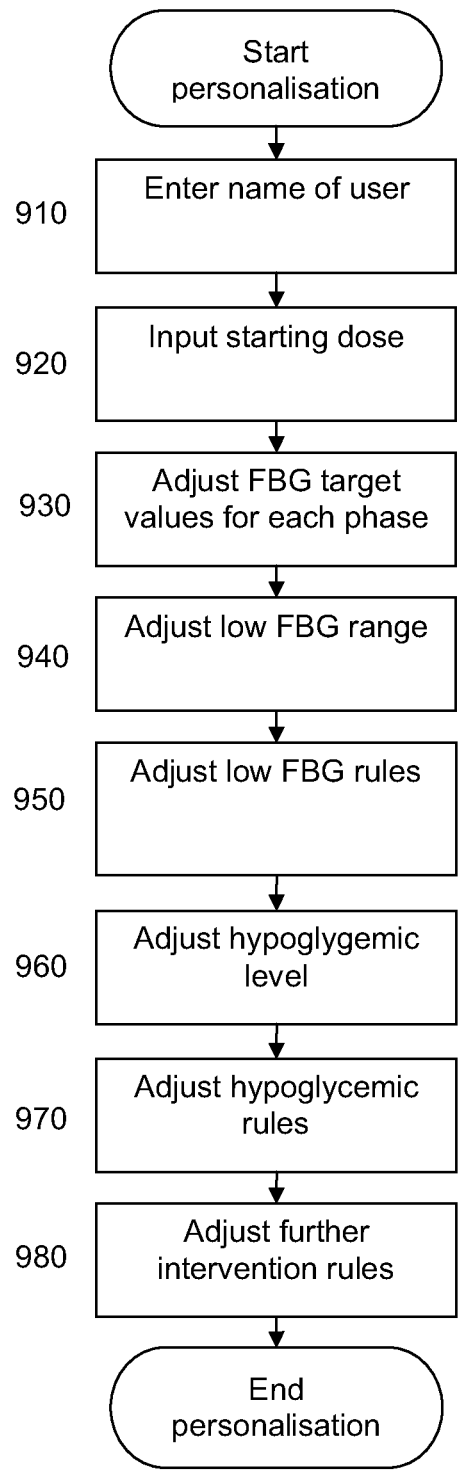
FIG. 9 is a flow diagram illustrating further steps of the operation procedure as shown in FIG. 3 in further detail.

FIG. 9 is a flow diagram illustrating the substeps of the personalization procedure. Preferably, the personalization procedure is started in the personalization step 330 shown in FIG. 3.

In step 910 of the personalization procedure, a name of the user of the medical device 100 is entered either via the user input unit 150 or electronically via interface 170. Preferably, the input of the name of the user is requested in order to identify the medical device 100 as the device used by the user. Alternatively, other information maybe input, such as picture data for a specific background picture, or even sound data so that the medical device 100 can be identified as the device used by the user. Step 910 offers the possibility that the medical device 100 can be differentiated from other medical devices 100 of the same kind used by other users. Personalizing e.g. the display, the sound, the appearance or specific functions of the medical device 100 reduces the risk that medical devices 100 belonging to different users are mixed up and a user uses the wrong medical device 100 and, thus, the wrong dose determining process for determining the dose to be administered.

In step 920, the starting dose or the dose currently used by the user is input e.g. via the user input unit 150 or alternatively via interface 170. In the case that the personalization also requires the adjustment of the target values for each phase these values will be adjusted in step 930. Preferably, the FBG target values are adjusted as the target values for each phase. Alternatively, it is not necessary to define target values for each phase but only the final target value for the last phase. In that case the different phase target values are calculated by the determining unit 140. In a further alternative, even no final target value has to be defined, as this is already defined by the algorithm selected. In such a case, the personalization procedure ends after step 920.

Depending on the algorithm selected, further values and rules are defined in steps 940 to 980. In the case that the selected algorithm does not allow a personalization of e.g. the low FBG range, the low FBG rules, the hypoglycemic levels and the hypoglycemic rules, the personalization procedure will end after step 930. However, if the algorithm selected allows the personalization of these values and rules, the personalization procedure proceeds with steps 940 to 980. In step 940, the low FBG range is adjusted. Preferably, this is done by selecting a specific threshold value out of a selection of threshold values or by selecting a range from a selection of ranges. Alternatively, a specific threshold value or values for a specific range are input via the user input unit 150 or the interface unit 170.

In step 950, the low FBG rules are adjusted. Preferably, this step comprises the selection of specific low FBG rules out of a set of predefined low FBG rules. Alternatively, additional low FBG rules can be defined and added. In step 960, the hypoglycemic levels are adjusted. Preferably, this adjustment of the hypoglycemic levels is performed in a similar way than the adjustment of the low FBG range in step 940. Preferably, the hypoglycemic rules are adjusted by selecting specific hypoglycemic rules from a set of predefined hypoglycemic rules. This adjustment is performed in step 970. Alternatively, additional hypoglycemic rules are defined in this step. Similarly, further intervention rules are defined in step 980.

Alternatively, the range values and rules defined in steps 940 to 980 are not defined in general for all phases, but for each phase. Furthermore, the data input or values and rules selected in steps 910 to 980 are stored automatically after they have been input or adjusted.

Figure 10:
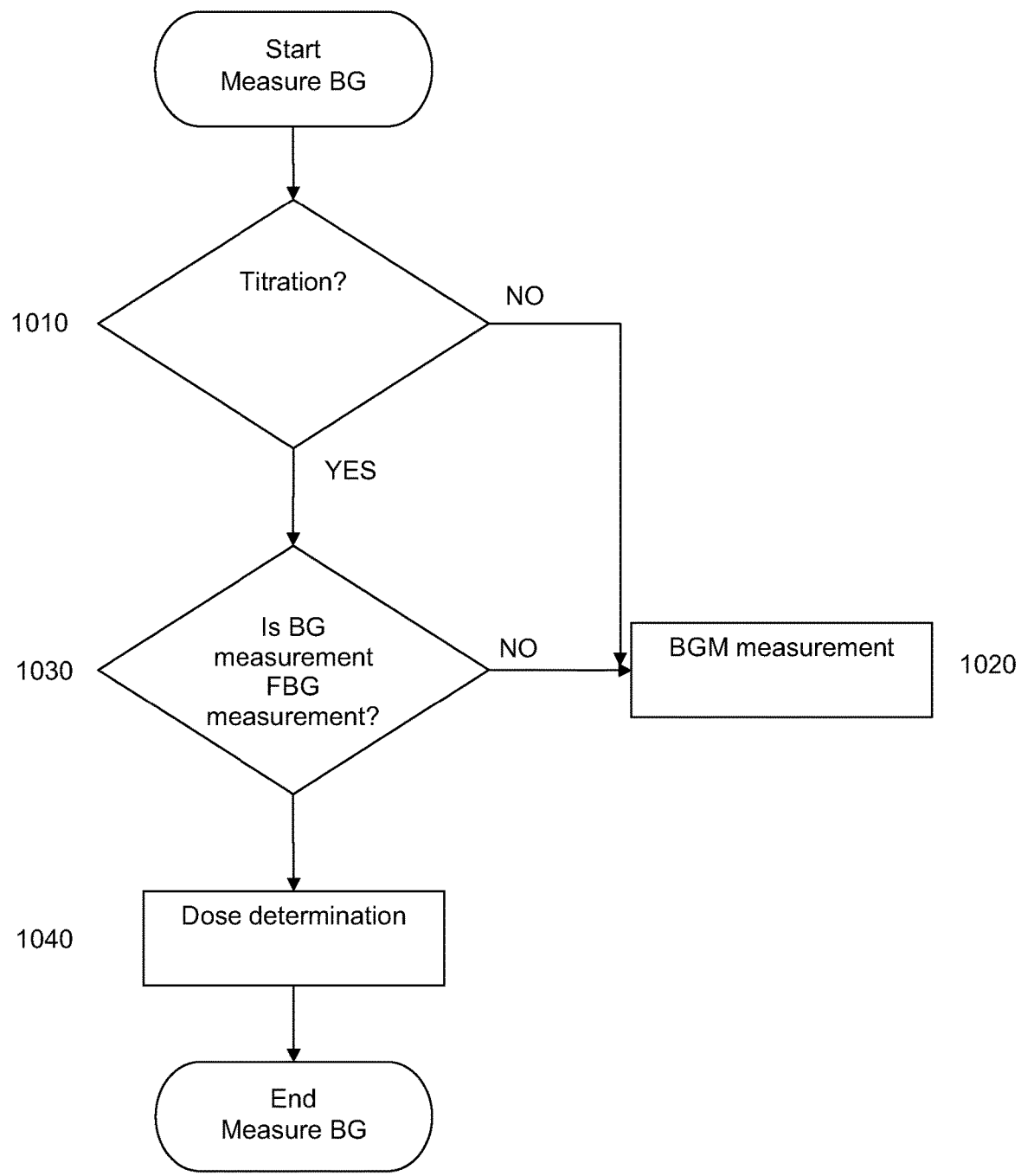
FIG. 10 is a flow diagram illustrating steps of the operation procedure shown in FIG. 2 in more detail.

As outlined above, the medical device 100 also provides the function for measuring the blood sugar level, preferably in the blood of the user. Preferably, the measurement of the blood sugar level, also called blood glucose value, is combined with the dose determination procedure as shown in FIG. 10. Alternatively, the medical device 100 provides different operation modes for measuring only the blood glucose value and for measuring the blood glucose value together with determining the dose to be administered.

Preferably, the blood glucose measurement procedure starts with detection, whether the medical device 100 is in a titration mode or not. This detection is performed in step 1010. Whether the medical device 100 is in a titration mode or not is preferably detected automatically via parameters stored in the storage unit 130 or determined by the determining unit 140. Preferably, such a parameter is the titration interval or the time of day. In the case that the parameter is the titration interval and the titration interval is, for example three days, the medical device 100 is automatically in the titration mode if the last titration has been three days ago. Alternatively, if the titration is based on the FBG value and, thus, the titration is performed in the morning, the medical device 100 is in the titration mode every morning. According to a further alternative, the medical device 100 is switched automatically to the titration mode based on a combination of both parameters, such as titration interval and time of day. In such a case, the medical device 100 is automatically switched to the titration mode if the titration interval has passed and when the time of day is when the titration is usually performed.

Alternatively, if no FBG value is measured the dose recommendation is given based on the previous FBG value and based on the previous measured or reported other blood glucose values. Preferably, a dose guidance is given even if no actual FBG value is available as long as this function is activated.

According to another alternative, the medical device 100 is switched to the titration mode manually via user input through the user input unit 150 or via input through interface 170.

In the case that the medical device 100 is not in the titration mode, the blood glucose measurement procedure proceeds to step 1020 in which the blood glucose value is measured. This blood glucose measurement step 1020 preferably includes that the blood glucose value is determined and transformed to a blood glucose value data which is forwarded to the storage unit 130 and stored in relation with the time and date indicating when the measurement has been made. Optionally, the user may mark this blood glucose value data as FBG value data or other blood glucose value data.

In the case that the medical device 100 is in the titration mode, then the blood glucose measurement procedure proceeds to step 1030, in which it is detected, whether the measurement is a FBG measurement or any other blood glucose measurement. In the case that the determination of the dose to be administered is based on the measurement of the FBG value, the blood glucose measurement procedure proceeds only to the dose determination step 1040 if the blood glucose measurement is a FBG measurement.

In dose determination step 1040, a dose to be administered is proposed and preferably the user is asked, whether the proposed dose should be maintained or changed to a different value.

As already indicated above, if the FBG measurement was not carried out as the it was e.g. forgotten or skipped for any reasons nevertheless a dose guidance is given. This includes that a dose recommendation for the dose to be administered is given preferably based on the previous FBG value or previous FBG values and based on the previous measured or reported other blood glucose values.

Preferably, it is automatically detected, whether or not the blood glucose measurement is a FBG measurement. Preferably, this detection is based on the time of day. In the case that the FBG measurement is usually performed in the morning, the medical device is automatically switched to the FBG measurement mode if the blood glucose measurement procedure is performed at morning time. Alternatively, the FBG measurement mode is detected via other parameters or defined via user input. In the latter case, the user is requested to select the respective mode. In the case that the medical device is not in the FBG measurement mode, the blood glucose measurement procedure proceeds to step 1020. In the case that the medical device 100 is in the FBG measurement mode, the blood glucose measurement procedure proceeds to step 1040 for determining the dose to be administered.

Figure 11:
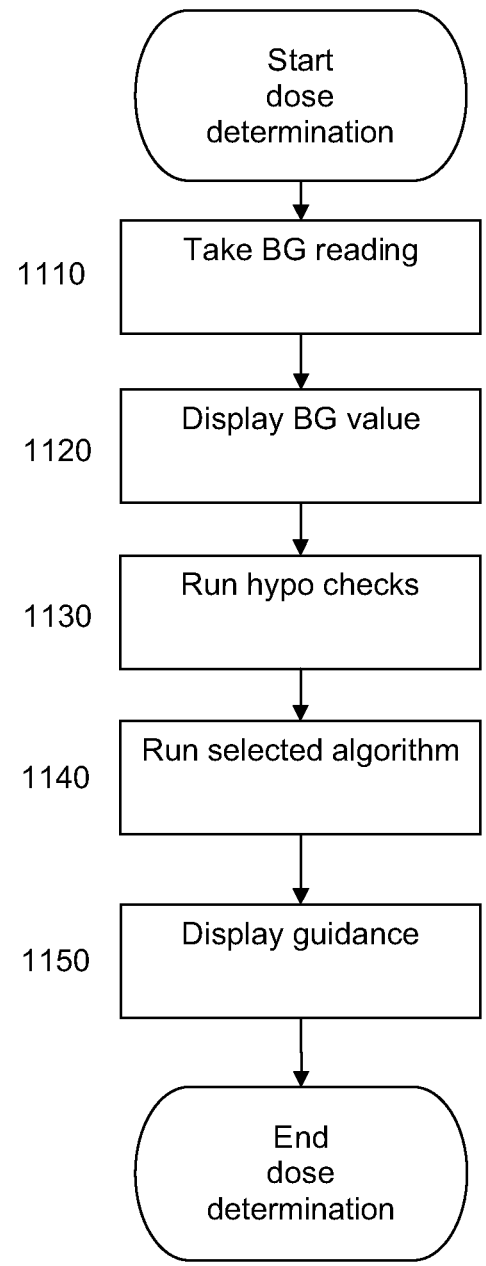
FIG. 11 is a flow diagram illustrating steps of the operating process as shown in FIG. 10 in more detail.

The substeps of the dose determination step 1040 are illustrated in more detail in FIG. 11.

FIG. 11 is a flow diagram illustrating the substeps of the dose determination procedure. In step 1110, the blood glucose level is measured and the corresponding blood glucose value determined. Preferably, the respective blood glucose value data is stored in the storage unit 130 together with the time and date when the blood glucose measurement was performed. As the blood glucose measurement is a FBG measurement, the stored value is preferably automatically marked as a FBG measurement value.

In step 1120, the measured blood glucose value is displayed on the display unit 160, preferably together with the time and date when the measurement was performed. Additionally, it is preferably also displayed on the display unit 160 that the blood glucose value is a FBG value. Moreover, the blood glucose value is displayed in unit mg/dl.

Either automatically after a specific predetermined time interval or depending on a user input, the dose determination procedure proceeds to step 1130, in order to run hypoglycemic checks. These hypoglycemic checks will be explained in more detail further below. In the case that the hypoglycemic checks performed in step 1130 do not come to a negative result, the dose determination procedure proceeds to step 1140. In step 1140, the selected algorithm is executed for determining the dose to be administered. When the dose to be administered has been determined in step 1140, guidance is displayed in step 1150. Preferably, this guidance includes information about the most recent FBG values and the actual FBG values together with the respective administered doses. Furthermore, the displayed guidance includes information about the actual dose to be administered. The guidance displayed will be explained in more detail further below in context with FIG. 14.

In the case that the dose determined in step 1140 is accepted by the user, the dose is stored in relation to the time and date when determined in the storage unit 130. In the case that the medical device 100 comprises a dose setting unit and a dose delivering unit, data representing the dose determined, are transmitted to the dose setting unit. Alternatively, data representing the dose to be administered are transmitted to an external dose setting unit and dose delivering unit.

Figure 12:
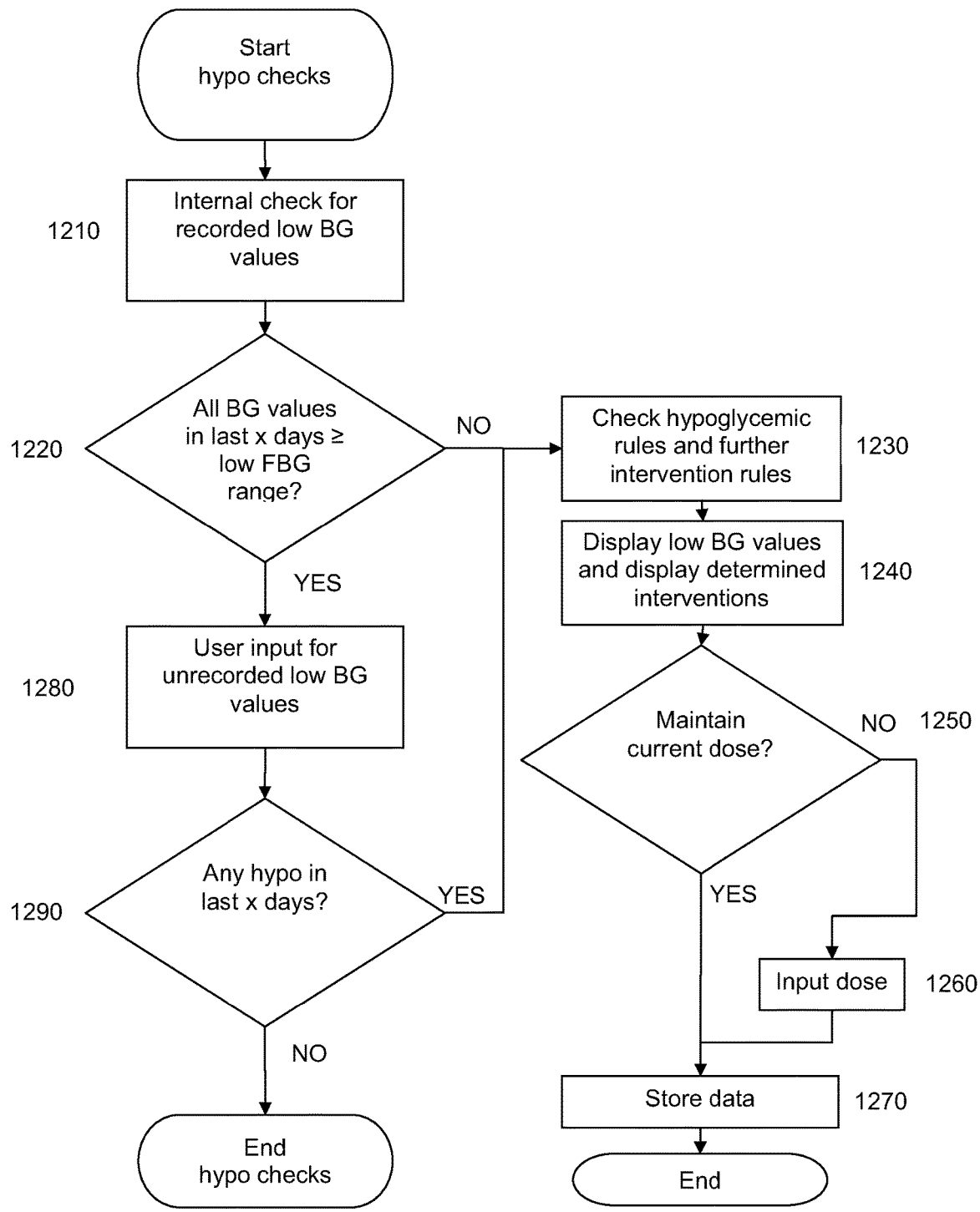
FIG. 12 is a flow diagram illustrating steps of the operating process shown in FIG. 11 in more detail.

FIG. 12 is a flow diagram illustrating the substeps of the hypoglycemic checks procedure. The hypoglycemic checks procedure is based on the hypoglycemic levels and hypoglycemic rules defined and personalized for the selected algorithm. In step 1210, an internal check is performed, whether low blood glucose values have been recorded. This internal check is preferably performed by checking, whether stored blood glucose values are below one ore more threshold values defined for the selected algorithm and for the respective phase currently being executed by the selected algorithm. In step 1220, it is checked whether or not the blood glucose values measured within a predetermined interval of days are equal or greater than the low FBG range defined for the selected algorithm and/or the current phase of the selected algorithm. In the case that one or more blood glucose values are below the defined low FBG range, the hypoglycemic checks procedure proceeds to step 1230.

In step 1230, preferably the low FBG rules and the hypoglycemic rules, together with the further intervention rules are checked. During this check it is determined, whether further actions have to be undertaken.

Alternatively, low FBG rules and the hypoglycemic rules are combined and use a common rule set.

In step 1240, preferably the determined low blood glucose values are displayed together with interventions determined according to the low FBG rules, hypoglycemic rules and further intervention rules. Alternatively, additional actions are undertaken, e.g. transmitting the low blood glucose values together with the corresponding dates and times and the corresponding administered doses to a computer system, network system or telecommunication system, to which e.g. health care professionals are connected.

Alternatively, an additional alert is transmitted via interface 170. Preferably, the recently administered dose is also displayed on the display unit in step 1240.

In step 1250, the user is asked, whether the proposed dose should be maintained or changed to a different value. The proposed dose, is preferably either the previous or a dose decreased in comparison to the previous dose.

In the case that the user of the medical device 100 is of the opinion that the proposed dose should not be maintained, the hypoglycemic checks procedure proceeds to step 1260, wherein the user can input a new value for the current dose, preferably via user input unit 150. Preferably, the input dose value is smaller than the current dose value. After the new dose value has been input, the hypoglycemic checks procedure proceeds to step 1270, wherein the input new dose value is stored, preferably in the storage unit 130.

In the case that the user is of the opinion that the currently proposed dose can be maintained, the hypoglycemic checks procedure directly proceeds to step 1270 for storing the current dose as the dose to be administered. Preferably, the dose is stored in relation to the time and date when it has been determined that this dose value is the dose value to be administered. After step 1270, the medical device preferably returns automatically to an operation mode, wherein specific operation procedures can be selected. Alternatively, the medical device 100 is switched off automatically or via user input.

In the case that in step 1220 it is determined that all blood glucose values of the last specified days have been equal or above the defined low FBG threshold value, i.e. the low FBG range, the hypoglycemic checks procedure proceeds to step 1280. In this step, the user is asked, whether a low blood glucose value has been detected by the user, but not recorded in the medical device 100. Via user input unit 150 the user is able to input the requested information. In the case that no additional low blood glucose values, i.e. unrecorded low blood glucose values are reported for a specific time interval, it is decided in step 1290 to end the hypoglycemic checks procedure. Preferably, after the hypoglycemic checks procedure, the selected algorithm for determining the dose to be administered is executed as shown, e.g. in FIG. 11. In the case that unrecorded low blood glucose values are reported by the user, it is decided in step 1290 to proceed with step 1230.

Preferably, the time intervals in steps 1220 and 1290 are identical. Alternatively, both time intervals may differ, depending on the parameters defined in the selected algorithm.

Figure 13:
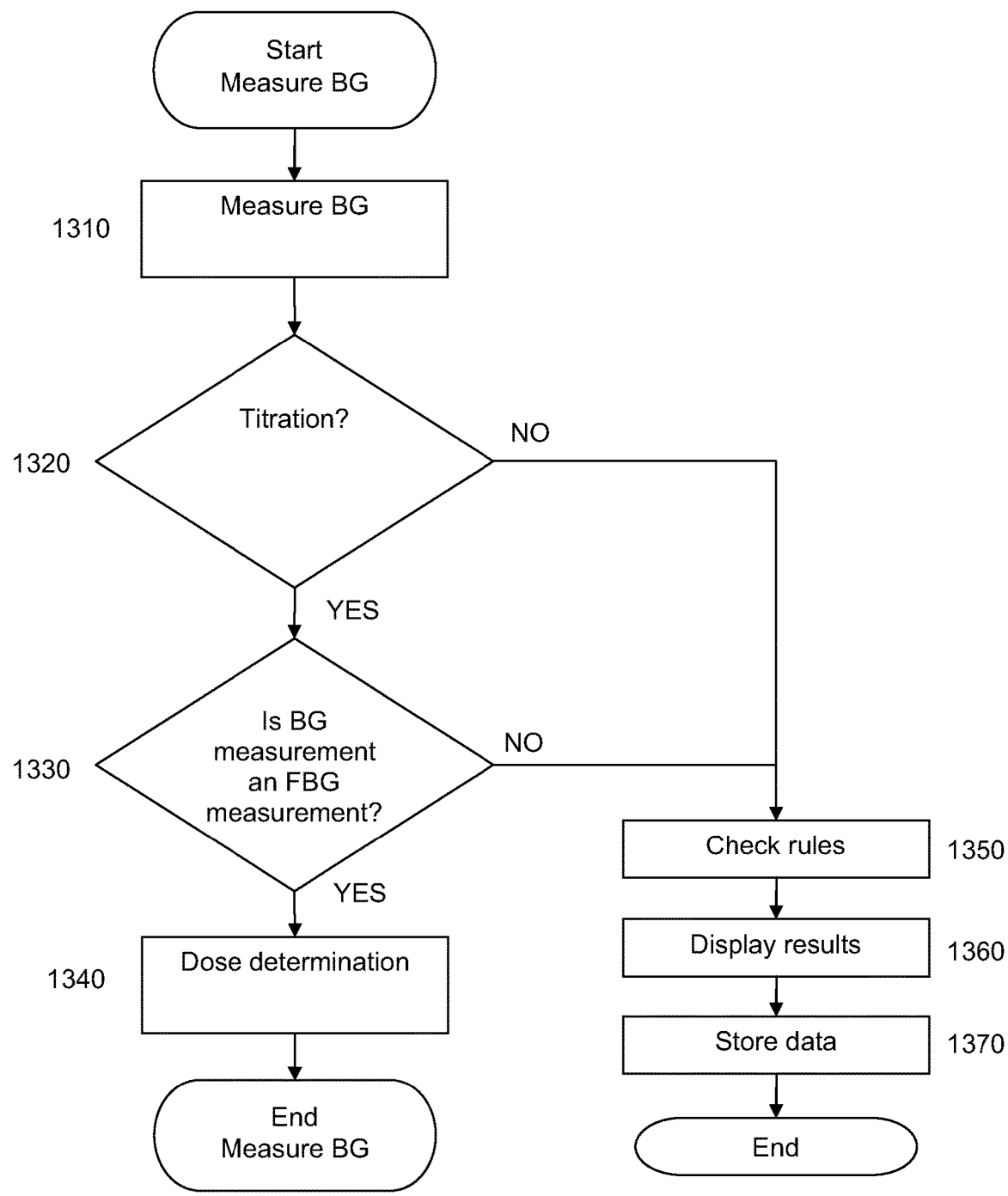
FIG. 13 is a flow diagram illustrating an alternative version of the steps of the operating process shown in FIG. 10.

FIG. 13 is a flow diagram illustrating an alternative version of the blood glucose measurement procedure shown in FIG. 10. The alternative version of the blood glucose measurement procedure starts in step 1310 with the measurement of the blood glucose value, as already explained in regard to step 1110. In step 1320 it is detected, whether or not the medical device 100 is in the titration mode or not. This detection is performed in a way, as already explained in context with step 1010. In the case that the medical device is in the titration mode, the alternative version for the blood glucose measurement procedure proceeds with step 1330, wherein it is detected, whether the blood glucose measurement is a FBG measurement. This detection is preferably performed in the same way as already outlined in regard to step 1030. In the case that the blood glucose measurement is a FBG measurement, the alternative version of the blood glucose measurement procedure proceeds with step 1340 for determining the dose to be administered. Step 1340 preferably corresponds to step 1040.

In the case that it is detected in step 1320 that the medical device 100 is not in the titration mode, the alternative version of the blood glucose measurement procedure proceeds to step 1350. In this step, the FBG rules, the hypoglycemic rules and the further intervention rules are checked according to the selected algorithm. When the respective rules have been checked, the alternative version of the blood glucose measurement procedure proceeds to step 1360, wherein the results of the rules check and the measured blood glucose value is displayed. Preferably, the same steps are undertaken in step 1360, as described for steps 1240 to 1260. In the subsequent step 1370, the respective data is stored, preferably together with the corresponding date and time. After step 1370, the medical device preferably returns automatically to an operation mode, wherein specific operation procedures can be selected. Alternatively, the medical device 100 is switched off. According to a further alternative, the results displayed in step 1360 are displayed until the medical device 100 is switched via user input to a different operation mode.

Figure 14:
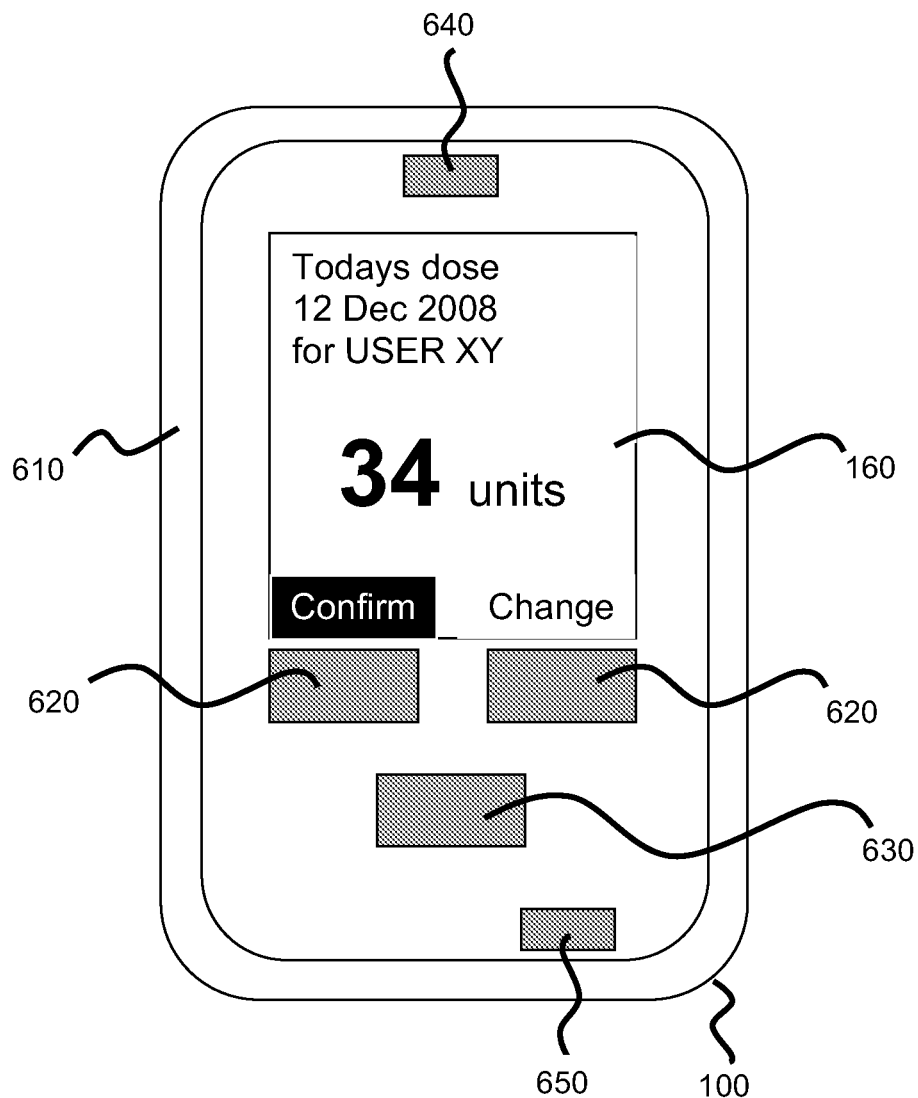
FIG. 14 is a further schematic diagram of the medical device shown in FIG. 1.

FIG. 14 is a schematic diagram showing the display of the medical device 100 for an operation mode, as explained in context with step 1150. The display unit 160 displays the guidance for the user. Preferably, this is the dose to be administered. As shown in FIG. 14, the functions "confirm" and "change" are assigned to the soft keys 620, so that the user of the medical device 100 can accept the dose determined in step 1140 or can change it. Alternatively, not only the determined dose is displayed but also the previously administered doses together with the corresponding measured FBG values. Thus, the user of the medical device 100 has additional information for deciding, whether to accept the determined and displayed dose or not. Moreover, personalization information is displayed in the display unit 160, such as the user name, so that the user can easily identify that the dose has been determined based on the algorithm and parameters selected and personalized for the user.

In the case that the medical device 100 is connected via a wired or wireless interface to an external dose setting unit, preferably the user will be requested, whether data corresponding to the displayed units for the dose to be administered shall be transmitted to the dose setting unit. In the case that the user confirms the transmission, respective data corresponding to the displayed dose are transmitted to the dose setting unit.

Alternatively, all information displayed on the display unit 160 is output via a voice module. The output via the voice module is preferably triggered via a user input. Alternatively, the output via voice module is performed automatically based on a user selection in a setup menu. According to a further alternative version, the information displayed on the display is transmitted to a headset, preferably via Bluetooth.

Figure 15:
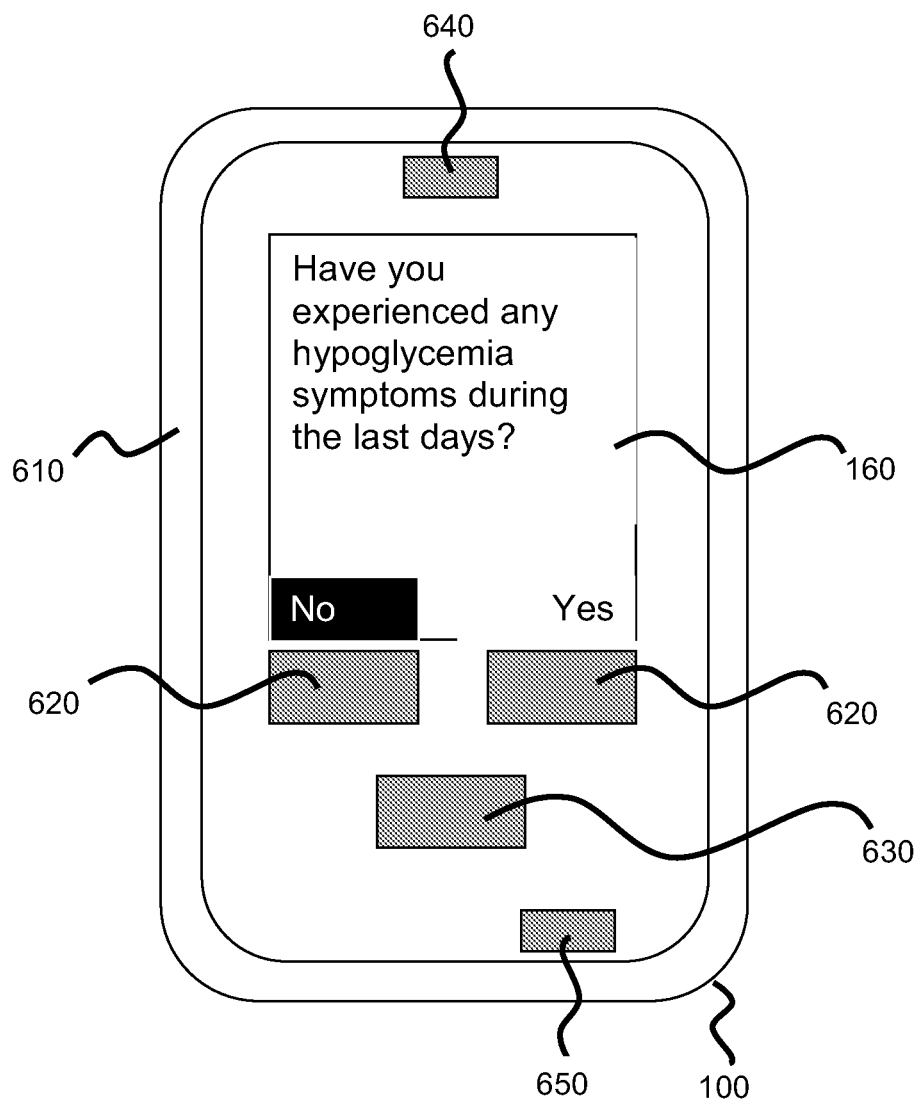
FIG. 15 is yet another schematic diagram of the medical device shown in FIG. 1.

FIG. 15 is a schematic diagram showing the display of the medical device 100, as preferably used in step 1290. Via display unit 160, the user is requested to report unrecorded hypoglycemia symptoms during the last days. Via soft keys 620, the user can select specific options for answering the questions displayed on the display unit 160.

Alternatively or additionally, hard keys are used such a back button.

In the case that the user has experienced no hypoglycemia symptoms, the user will press the left soft key 620 which represents the option "No". In the case that the user has experience hypoglycemia symptoms during the last days, the user will press the right soft key 620 which represents the option "Yes".

Alternatively, the options are selected via speech input. For this the voice module additionally comprises a microphone 650 and a speech recognition unit so that the voice input can be transformed into data.

A similar menu, as shown in FIG. 15, is preferably used to report or mark specific events independently from a blood glucose measurement procedure.

Figure 16:
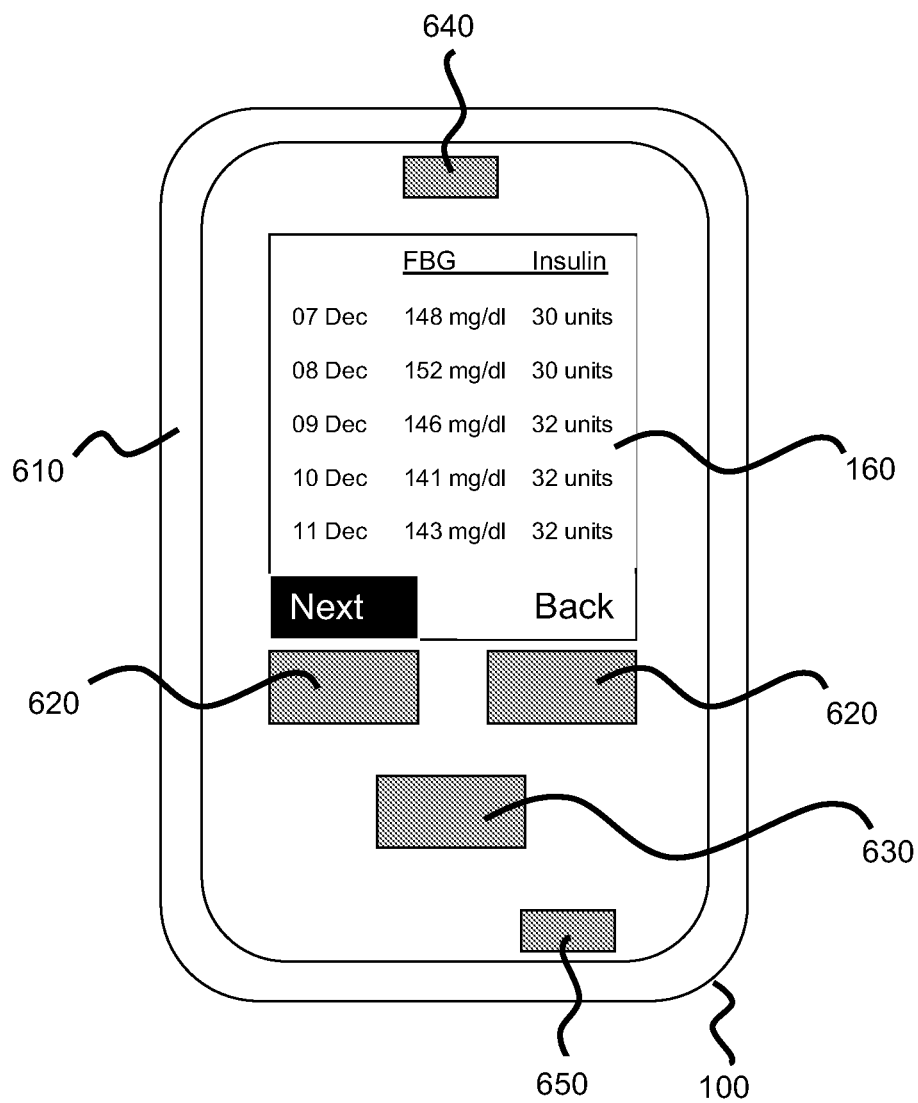
FIG. 16 is still a further schematic diagram of the medical device shown in FIG. 1.

FIG. 16 is a schematic diagram showing an exemplary display of the medical device for the operation mode "Review History". In such an operation mode, the user is able to retrieve data of the measured FBG values in correlation with the respective date and the respective administered doses. As shown in FIG. 16, a list of FBG values and administered insulin units is displayed on the display unit 160. In the left column, the respective date is displayed when the FBG value is measured and when the respective dose of insulin had been administered. Via the soft keys 620, the user is able to scroll through the list of dates, FBG values and dose of insulin. This function offers the user of the medical device 100 to monitor the progress of the treatment. Alternatively, the results may be displayed graphically, whereby the tendency of the development of the FBG values is additionally analyzed via a statistical module.

Preferably, for reviewing the history of the measurements the user can define whether the FBG values shall be displayed or, whether the recorded events shall be displayed or the reported events shall be displayed or all events should be displayed or whether all blood glucose values should be displayed on the display unit 160.

Moreover, additional functions are preferably implemented in the medical device 100 and configurable via a setup menu. This preferably includes the function of automatic switching on the medical device 100 at a predefined time. Preferably, the predefined time is the time for measuring the FBG value. Thus, the user of the medical device 100 is reminded of measuring the FBG or to perform the titration. Preferably, either an acoustic or a visual alarm is used to remind the user of the medical device 100. For the acoustic alarm the loudspeaker 640 is preferably used. Additionally, the alarm which is preferably also active when the other functions of the medical device are switched off is used to remind the user of the medical device 100 to administer a dose of insulin.

Figure 17:
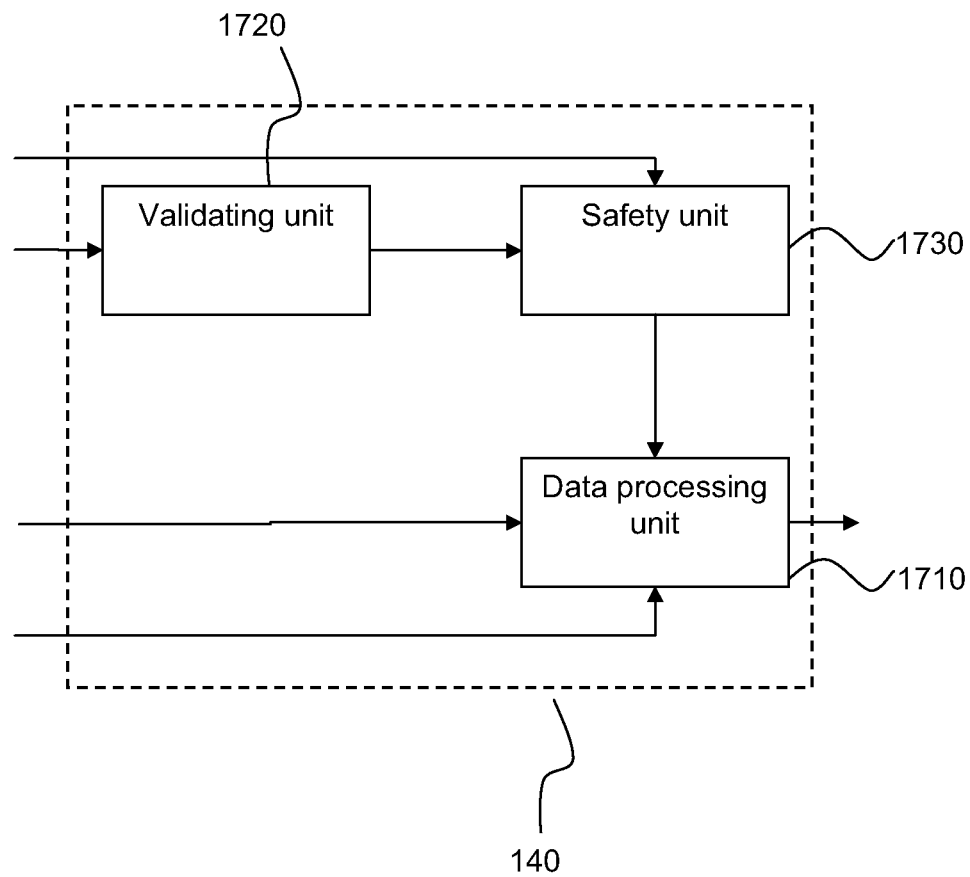
FIG. 17 is a schematic diagram of the determining unit of the medical device shown in FIG. 1.

FIG. 17 is a schematic diagram of the determining unit 140 of the medical device 100. Preferably, the determining unit 140 comprises a data processing unit 1710 for executing at least one processing function. Preferably, the data processing unit 1710 is arranged to execute a number of processing functions, wherein at least one processing function is for modifying data retrieved from the storage unit 130 and at least one further processing function for providing information for glycemic control based on blood glucose value data received from the receiving unit 120 and data received from the storage unit 130. In particular, the data processing unit is adapted to execute the selected algorithms for determining the dose to be administered. For this, the data processing unit is connected to the receiving unit 120. Thus, the data processing unit 1710 can receive data from the receiving unit 120 and forward data to the receiving unit 120.

Furthermore, the determining unit 140 comprises a validating unit 1720 arranged to validate received data such as identification data, authentication data, authorization data, etc. and to provide validation data corresponding to the validation of the received data. In order to receive these data, also called security data, the validating unit 1720 is preferably connected to the receiving unit 120. Alternatively, the validating unit 1720 and the data processing unit 1710 use a common data channel or line for receiving data from the receiving unit 120. Preferably, the security data is a password or an activation key, i.e. a code, wherein the validating unit 1720 validates the password or the activation key based on data stored in the storage unit 130 or data implemented in the validating unit 1720. Alternatively, the medical device 100 comprises a SIM card from which the validating unit 1720 receives the data to be compared with the received security data.

Based on the validation of the received security data and the corresponding data stored in the medical device 100, the validating unit 1720 outputs validation data indicating, whether the validation of the received security data was successful or not. Preferably, the validation data is a bit or flag indicating the result of the validating process. Alternatively, the validation data is a code word indicating the result of the validating process.

Preferably, the validation data are output to a safety unit 1730. Alternatively, the validation data are stored in the storage unit 130 or in an internal storage of the determining unit 140. Thus, the safety unit 1730 receives the validation data either from the validating unit 1720 directly or from the storage unit 130 or the internal storage of the determining unit 140.

The safety unit 1730 is arranged to control an execution of a predetermined function out of the processing functions which are executed by the data processing unit 1710. The control of the execution of the predetermined function is based on the validation data received by the safety unit 1730. Thus, the data processing unit 1710 can execute predetermined functions only if the safety unit 1730 allows the execution of the predetermined functions.

Preferably, the execution of one or more predetermined functions by the data processing unit 1710 is only allowed by the safety unit 1730 via a control signal provided to the data processing unit 1710 if the received security data was successfully validated by the validating unit 1720. Via this control circuit or unit, it can be prohibited that e.g. data are retrieved from the storage unit 130 and modified by the data processing unit 1710, without any valid validation. In that way, it can be prevented that an unauthorized person modifies the setup or in particular changes parameters in a selected algorithm which would lead to a determined dose value which might be harmful for the user of the medical device 100. By controlling only specific functions of the medical device 100 via the validation of security data, the user of the medical device 100 can use the medical device 100 in any case as a simple blood glucose meter according to a preferred alternative. The dose determining functions are furthermore only available according to the preferred alternative if they have been activated by an authorized person via the security data, such as an activation key or a password. In such a way, the medical device 100 provides the necessary functionality that critical functions are only available or can only be amended by an authorized person, such as health care professionals.

According to alternative versions of the preferred embodiment of the medical device 100, the interface 170 is a wired or wireless interface for receiving and transmitting data. Preferably, the interface 170 is a USB interface, an IEEE 1394 interface, a Bluetooth interface, ZigBee interface, a WI-FI interface, a UMTS interface or a GSM interface. Via such an interface 170, the medical device 100 is capable to receive security data and to provide it to the validation unit 1720. Moreover, such an interface allows it for health care professionals to configure the medical device 100 via remote control. This will be explained in detail further below.

Figure 18:
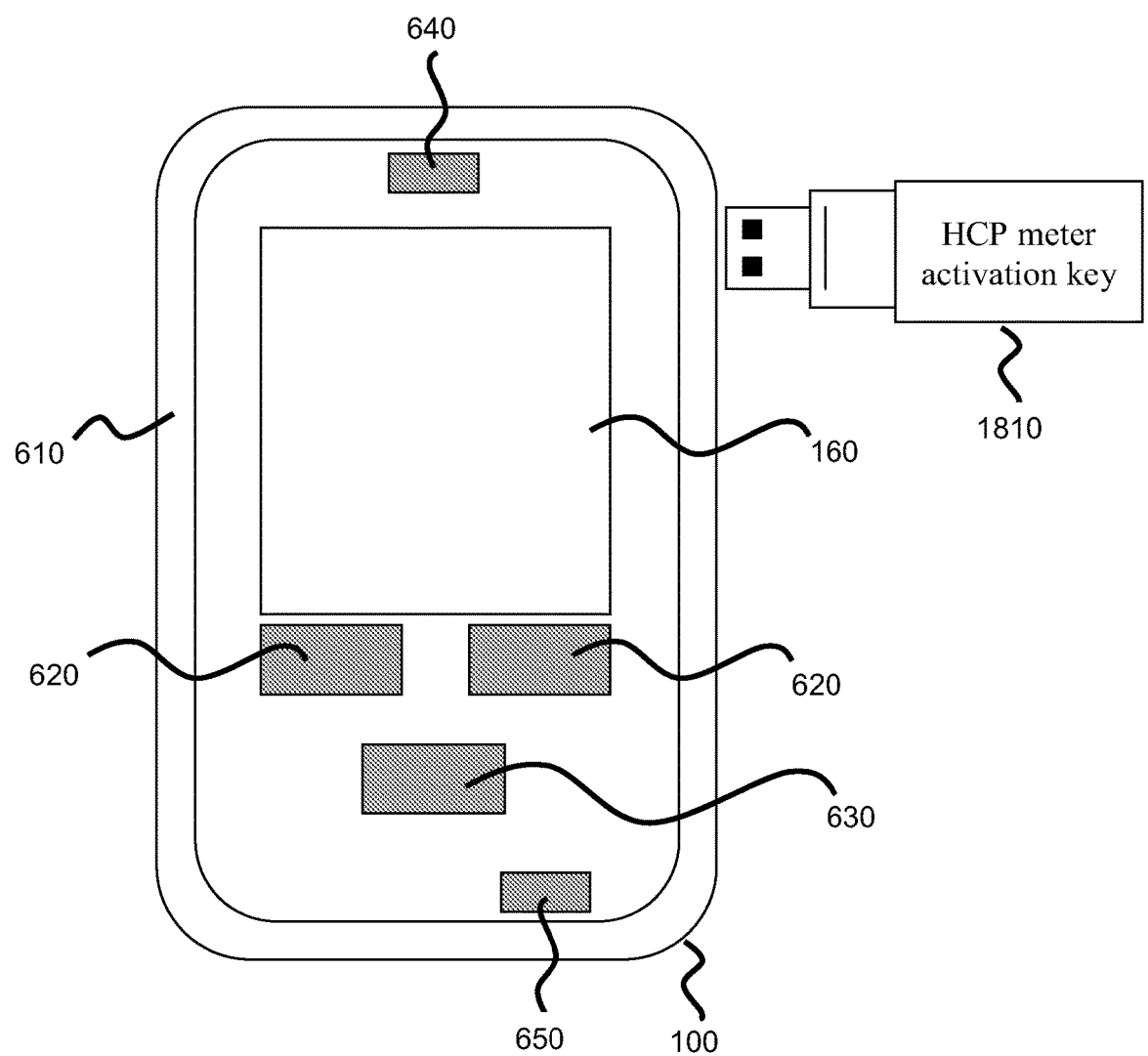
FIG. 18 is a schematic diagram illustrating the medical device according to a further preferred embodiment of the invention.

FIG. 18 shows a schematic diagram of the medical device 100 according to a preferred alternative of the preferred embodiment of the invention. The interface 170 is a USB interface capable to receive the security data via a USB stick 1810 or via a USB link. On the USB stick 1810 an HCP meter activation key is stored. In this preferred alternative the validating unit 1720 requests the HCP meter activation key continuously from the USB port. As long as the HCP meter activation key necessary for the validating process can be retrieved via the USB port, the data processing unit 1710 can execute the predetermined functions. In the case that the USB stick 1810 or the USB link is disconnected from the medical device 100 the validating unit 1720 can no more receive the necessary HCP meter activation key for the validating process. Accordingly, the validating unit 1720 outputs a validation signal indicating that the validation process was not successful. Thus, the safety unit 1730 prevents the data processing unit 1710 from executing the predetermined functions.

Figure 19:
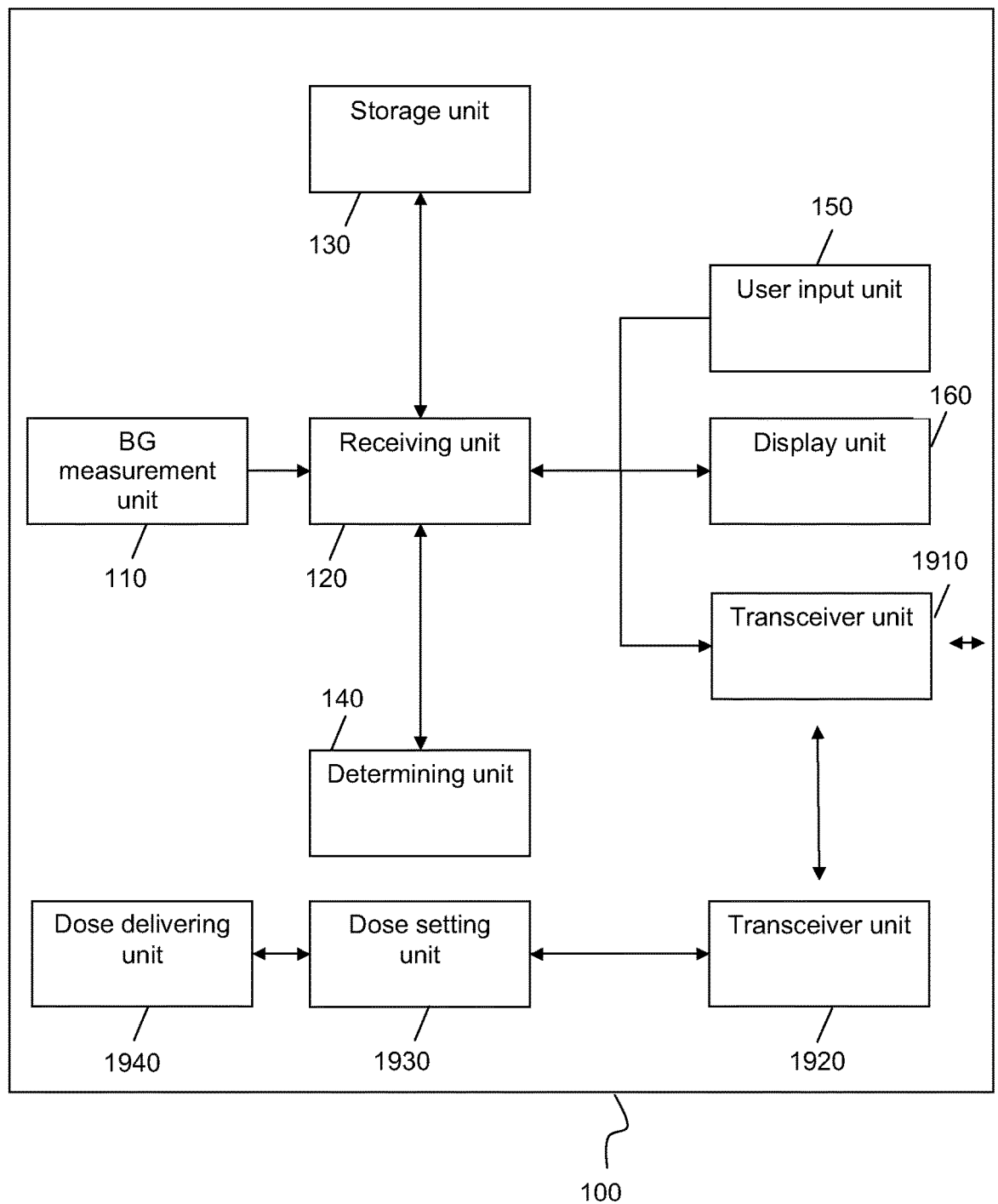
FIG. 19 is a schematic diagram illustrating the medical device according to another preferred embodiment of the invention.

FIG. 19 is a schematic diagram illustrating the medical device 100 according to a further preferred embodiment of the invention. The medical device 100 comprises a blood glucose measurement unit 110, a receiving unit 120, a storage unit 130 and a determining unit 140. Additionally, the medical device 100 comprises a user input unit 150 and a display unit 160, as already shown in FIG. 1. Additionally, the medical device 100 shown in FIG. 19 comprises a transceiver unit 1910 capable to communicate, preferably wireless, with additional internal and external components. Furthermore, the medical device 100 comprises a further transceiver unit 1920 capable to communicate with the transceiver unit 1910. The transceiver unit 1920 is connected to a dose setting unit 1930 for setting a dose to be administered according to the signals received from the transceiver unit 1920. The dose setting unit is further connected to a dose delivering unit 1940. Preferably, the transceiver unit 1920, the dose setting unit 1930 and the dose delivering unit 1940 form a functional and structural unit which is separated from the other components shown in FIG. 19. Preferably, the transceiver unit 1920, the dose setting unit 1930 and the dose delivering unit 1940 form an insulin pen or insulin pump or an inhale device which receives signals from the transceiver unit 1910 which dose has to be set in order to deliver a dose determined by the determining unit 140. If the transceiver unit 1920 receives the respective signals for setting a dose, the dose setting unit 1930 activates the respective dose setting mechanism for setting the dose according to the received signals. The delivery of the dose to be administered is either activated manually by the user of the medical device 100 or automatically activated. In the case of an insulin pen the activation is preferably done manually by the user. In the case of an insulin pump the activation is preferably done automatically. According to a preferred alternative the dose delivering unit 1940 forwards a signal to the transceiver unit 1920 that the dose set has been successfully delivered. Accordingly, the transceiver unit 1920 transmits the respective signal of the successful delivery of the dose set to the transceiver unit 1910. Thus, the successful delivery of the set dose can be protocolled by the determining unit 140 and stored in the storage unit 130.

In the case that the blood glucose measurement unit 110 is a continuous sensor which is e.g. implanted and the dose delivering unit 1940 is an insulin pump an automatic delivery system is provided. In the case that this full automatic delivery system asks for a user confirmation in the case of a dose increase a semi closed loop control is provided.

Figure 20:
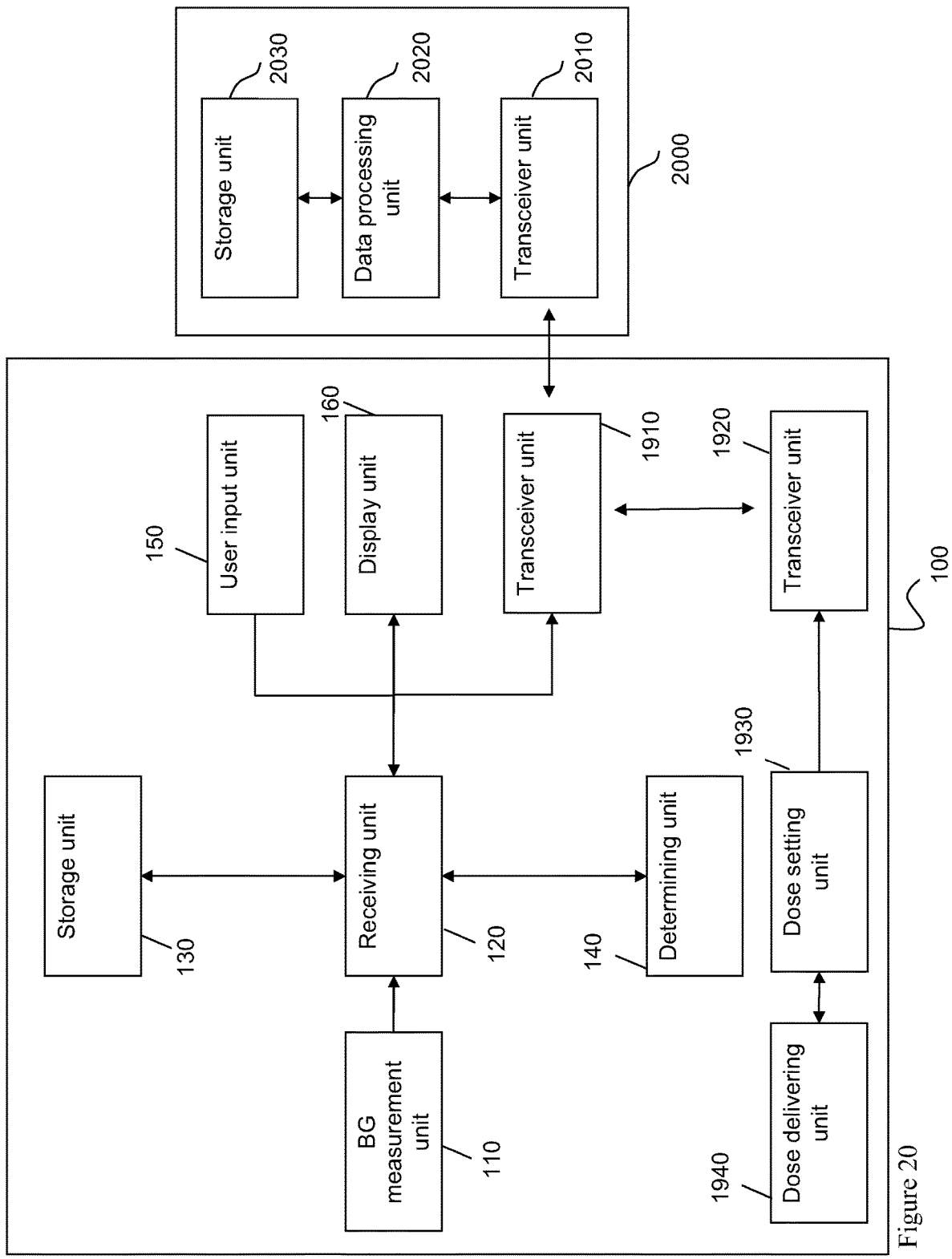
FIG. 20 is a schematic diagram showing the medical system according to another preferred embodiment of the invention.

FIG. 20 is a schematic diagram showing a medical system according to another preferred embodiment of the invention. In particular, FIG. 20 shows the medical device 100 as shown in FIG. 19 together with an administration device 2000. Preferably, the administration device 2000 comprises a transceiver unit 2010 which is connected to data processing unit 2020. Furthermore, the data processing unit 2020 is connected to a storage unit 2030. The transceiver unit 2010 is capable to communicate with the transceiver unit 1910. Preferably, both transceiver units 2010 and 1910 communicate via a wireless data connection. Alternatively, both transceiver units 2010 and 1910 communicate via a wired data connection such as a local area network (LAN) or Internet.

The data processing unit 2020 is arranged to provide security data, such as e.g. an HCP meter activation key, which is transmitted by the transceiver unit 2010 to the transceiver unit 1910. Thus, the administration unit 2000 can configure the medical device 100. Preferably, the data processing unit 1710 is capable to execute the predetermined functions controlled by the safety unit 1730 as long as the administration unit 2000 is in connection with the medical device 100. In the case that the administration unit 2000 is on a remote place, such as an office of the health care professional, the health care professional using the administration unit 2000 can configure, modify or control the medical device 100 also via the wireless connection between the transceiver unit 2010 and the transceiver unit 1910. As mentioned before preferred versions of the transceiver units are UMTS or GSM or WI-FI transceivers. Alternatively, at least one of the transceivers is capable to be connected to a LAN or Internet so that the medical device 100 and the administration unit 2000 can communicate via these networks. Such a medical system offers the possibility that critical functions of the medical device 100 are reconfigurable via remote control only by an authorized health care professional, while other functions of the medical device 100 can still be used and modified by the user of the medical device 100. Moreover, such a system offers the possibility to directly forward alerts produced by a low FBG check or a hypoglycemic check directly to the health care professional. These features will be described in more detail further below.

Besides the functions described above and below the medical device 100 is used as a so called "data recorder" and "data communication device" for assisting the self adjustment of the blood glucose level of the user of the medical device 100. Preferably, the medical device 100 measures the FBG values as described above and stores the FBG values, the administered doses and the blood glucose values measured within the titration interval in the storage unit 130. However, the dose determining function is deactivated in this mode.

The dose recommendation is predefined and selected by an HCP, who gets feedback on the measured FBG values and other blood glucose values. Preferably, the FBG values and the other blood glucose values and the respective measurement times are recorded over one week. Alternatively, any other time interval can be used. Preferably, these data are transmitted via a wired connection or a wireless connection either automatically after the predefined time interval or based on a user input to the HCP, i.e. preferably to administration unit 2000.

According to a further alternative an alert set on the medical device 100 reminds the user of the medical device 100 to transmit the recorded data to the administration unit 2000 of the HCP. On reception of the recorded data the administration unit 2000 performs a check of the data, preferably based on the low FBG rules and hypoglycemic rules described above, and determines the dose to be administered based on the above described algorithms. This can be done automatically or based on a user input of the HCP via a keyboard or other user interface of the administration unit 2000. Alternatively, an alert is output by the administration unit 2000 in the case that a specific event is identified according to the low FBG rules or the hypoglycemic rules.

As mentioned above, the dose recommendation is preferably determined automatically. In the case that no specific event has been identified by the administration unit 2000, the new dose recommendation for the next titration interval is transmitted to the medical device 100 automatically or based on a confirmation of the HCP. In the case that a specific event has been detected, the administration unit 2000 or alternatively the HCP modifies the dose, the titration interval or transmits a message to the user of the medical device 100 with further instructions.

Alternatively, the user of the medical device 100 contacts the HCP via phone or in person in order to get new instructions for the new titration interval.

Alternatively, the recorded data are transmitted to an administration unit 2000 placed in a service center, where the data are processed automatically. In the case of an identified specific event, an HCP is informed via e.g. a network connection who decides which further actions are undertaken.

Figure 21:
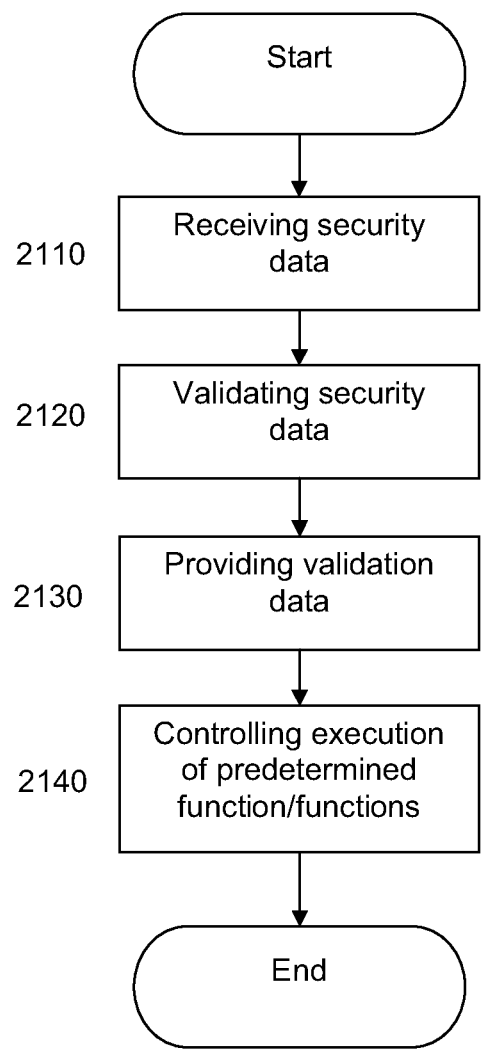
FIG. 21 is a flow diagram illustrating steps of another operating procedure of the medical device according to another preferred embodiment of the invention.

FIG. 21 is a flow diagram illustrating the steps of the method for providing information for glycemic control according to another preferred embodiment of the invention. In step 2110 security data are received. Preferably, the security data are received by the receiving unit 120 via interface 170. Furthermore, the received security data are preferably forwarded to the determining unit 140. The received security data are validated in the next step 2120. Preferably, the validation of the security is performed via comparing the received security data with reference data. In the case that the received security data is a password, the password is validated in step 2120 by comparing the password with a copy of the password stored in the medical device 100. Alternatively, a check sum of the received security data may be taken to validate the received security data. According to a further alternative an authentication key or code is used as security data, wherein in step 2120 a corresponding key or code is used in the validating step in order to validate the received authentication key or code. Preferably, an HCP meter activation key is such an authentication key.

Depending on the result of the validating step, validating data are provided in step 2130. Preferably, the validation data is a bit indicating, whether or not the validation was successful. For example, the validation data is the bit "1" if the security data was successfully validated in step 2120 in regard to the stored reference data. In the case that the received security data could not be validated successfully, in respect to the reference data, the validation data are represented by bit "0". Alternatively, the validation data is a Boolean value indicating, whether or not the validation step 2120 was successful. In that case the Boolean value would have the values "true" or "false". According to a further alternative version validation data are only provided in the case that the validation process in step 2120 was successful. In the case that the validation process in step 2120 was not successful, no validation data are provided.

Preferably, the validation data are provided by the validating unit 1720.

In step 2140 the execution of at least a predetermined function out of a number of different processing functions is controlled based on the validation data. Preferably, the execution of the predetermined function or functions is only permitted in the case that the validation process in step 2120 was successful. Thus, it is ensured that the predetermined function or functions can only be executed if the received security data are the correct security data corresponding to the stored reference data. Preferably, such a predetermined function is a processing function for modifying data retrieved from storage unit 130 such as e.g. the setup procedure or a processing function for providing information for glycemic control based on received blood glucose value data and data retrieved from the storage unit 130 such as e.g. the dose determining procedure.

Preferably, the step of controlling the execution of the predetermined function or functions differentiates between different authorization levels for controlling the respective predetermined functions. For example, for specific predetermined functions it is only necessary to receive the security data once so that the respective specific predetermined functions can be executed always if required, whereby other predetermined functions always require to receive the actually provided validation signal, in order to be executed. Thus, it is possible to activate specific predetermined functions by receiving the security data once. For other specific predetermined functions it is necessary to receive the security data in each case the respective predetermined function has to be executed.

In that way it is arranged that e.g. a process for determining the dose to be administered is activated by providing the security data once. After this initial activation the medical device 100 can be used for determining the respective dose to be administered, without any further need to receive the security data again. Other functions, such as modifying specific data in the storage unit 130, however, require receiving the password each time they are executed. Thus, it is ensured that only a specific person, such as a health care professional being capable of providing the security data, is able to modify data, such as parameters of the selected algorithm.

Preferably, a configuration file, a lookup table or a database is provided which provides information indicating which of the processing functions requires validation data and which do not require validation data. Furthermore, such a configuration file, lookup table or database provides information which of the processing functions requires the validation data only once and which require the validation data always. In such a configuration file, lookup table or database it is preferably also stored, whether the validation data have been already provided once, so that the processing functions which require only validation data once, stay executable even if the security data are no more provided.

The described steps 2110 to 2140, thus, define a method for providing information for glycemic control wherein specific predetermined functions are unlocked via security data and other specific functions can be only executed if the security data are provided before and/or during their execution.

Figure 22:
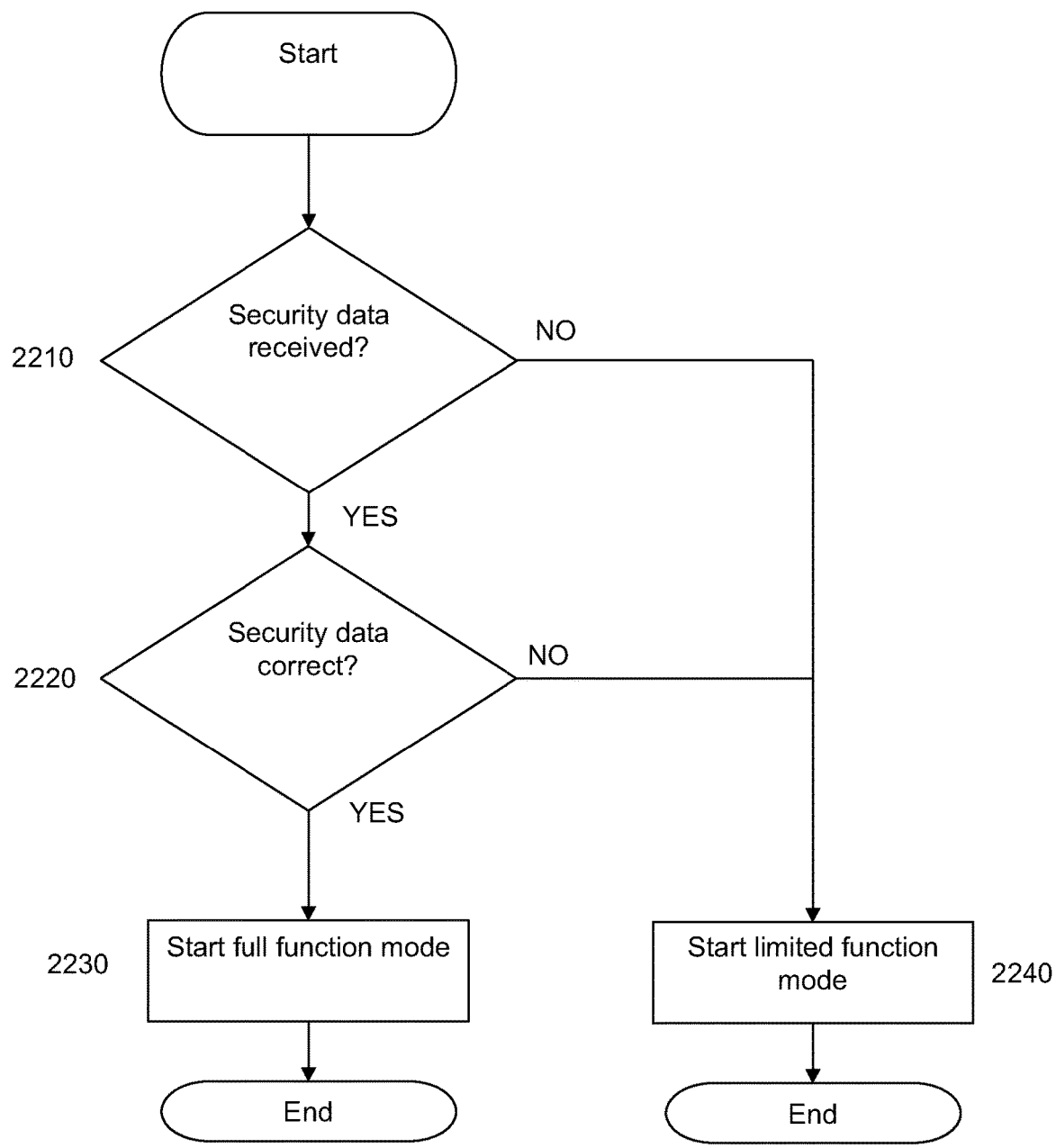
FIG. 22 is a flow diagram illustrating steps for an alternative operating procedure of the medical device according to another preferred embodiment of the invention.

FIG. 22 is a flow diagram illustrating the method for providing information for glycemic control according to another preferred embodiment of the invention. The method shown in FIG. 22 is preferably used when operating medical device 100. In step 2210 it is detected, whether security data have been received. Preferably, this includes the detection, whether the security data have been received once in the past and/or whether the security data are received actually. Whether the correct security data have been received once in the past is preferably checked by analyzing the above mentioned configuration file, lookup table or database. In the case that actually security data are received, the method for providing information for glycemic control proceeds with step 2220, wherein it is detected, whether the correct security data are received. This detection is preferably performed via steps 2120 and 2130 shown in FIG. 21. In the case that the received security data are correct, the method for providing information for glycemic control proceeds with step 2230. In this step the full function mode is started, i.e. all processing functions can be executed under control of the safety unit 1730. This means that not only blood glucose values can be measured, but also the dose to be administered can be determined and new algorithms defined, existing algorithms modified, new algorithms selected or the personalization of a selected algorithm changed.

In the case that in step 2210 it is detected that actually no security data are received, the method for providing information for glycemic control proceeds with step 2240. In this step the limited function mode is started, i.e. only a limited number of processing functions can be executed under the control of the safety unit 1730. In the case that the correct security data has been already provided in the past, the predetermined functions can be executed under the control of the safety unit 1730 which require only the unlocking of this function via receiving the security data once. As mentioned above, such processing functions are preferably processing functions for determining the dose to be administered. Furthermore, functions which do not require validation data for being executed are, for example, functions for measuring the blood glucose value. In such a case the medical device 100 can be used always as a blood glucose meter without any authentication or other kind of identification for use of the medical device 100. All other functions which require that the validation data are always provided before and/or during execution cannot be executed in the limited function mode.

In the case that in step 2220 it is detected that the received security data is incorrect, the method for providing information for glycemic control also proceeds to step 2240 providing the limited function mode. In such a case visual and/or acoustic information is provided to the user of the medical device 100 that the received security data are incorrect. Alternatively, no such information is provided. According, to a further alternative the user is asked by a message whether he wants to input new security data and to retry validating the security data. In such a case it is proceeded to step 2210 again.

Figure 23:
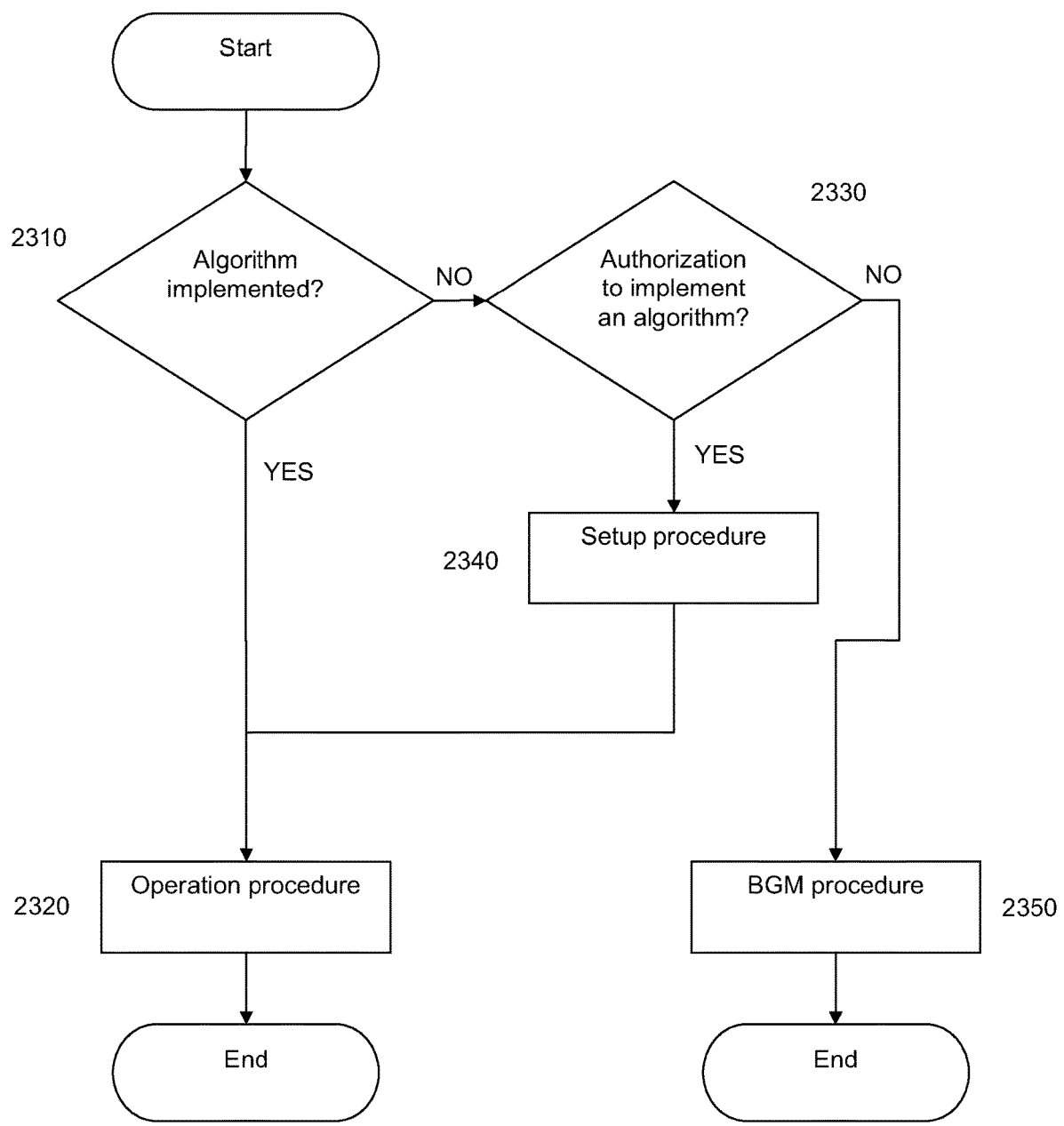
FIG. 23 is a flow diagram illustrating steps of another operating procedure of the medical device according to another preferred embodiment of the invention.

FIG. 23 is a flow diagram illustrating a further aspect of the method for providing information for glycemic control as shown in FIG. 21. In step 2310 it is detected, whether or not an algorithm for determining a dose to be administered is already implemented. As already outlined in regard to FIGS. 21 and 22, preferably an algorithm for determining a dose to be administered is only implemented if the correct security data have been already received once, as for selecting an algorithm for determining a dose to be administered preferably requires that this function has been unlocked via the security data. Thus, if the correct security data have already been received in the past and a respective algorithm has been selected and personalized correctly then the medical device 100 is capable to perform the necessary processing functions for determining a dose to be administered to the user of the medical device 100.

Therefore, if a selected and completely personalized algorithm is detected in step 2310 the method for providing information for glycemic control proceeds to step 2320 which preferably provides functions, such as measurement of the blood glucose level, determining the dose to be administered, marking of an event, reviewing the history and changing of settings in accordance with the activation rules provided by the safety unit 1730. In the case that it is detected in step 2310 that no algorithm is implemented or that a selected algorithm is not completely or incorrectly implemented, the method for providing information for glycemic control proceeds to step 2330 for detecting, whether the authorization for implementing or selecting an algorithm has been received. Step 2330 for detecting, whether the authorization to implement or select an algorithm has been received, is based on the steps 2110 to 2140, as explained in regard to FIG. 21.

As outlined above, for selecting an algorithm the correct security data have to be received. Moreover, as long as the selected algorithm is not correctly implemented, i.e. modified or personalized according to the requirements and needs of the use of the medical device 100, the selected algorithm is not ready to be used. In such a case always the correct security data are required in order to have the authorization to implement the selected algorithm correctly. Accordingly, it is necessary to receive security data before and/or during implementing the selected algorithm. In the case that the correct security data are received and the validation data indicate that the security data have been validated accordingly, the authorization for implementing an algorithm is given in step 2330 and the method for providing information for glycemic control proceeds to step 2340.

Step 2340 provides the setup procedure, wherein an algorithm can be selected and/or personalized. When the algorithm has been selected and personalized as described in respect to FIGS. 3 to 9, the method for providing information for glycemic control proceeds to step 2320. Once the algorithm has been selected and setup correctly according to step 2340, the medical device 100 will directly proceed to step 2320 the next time when being switched on according to the preferred embodiment of the invention. In the case that no authorization is given for implementing an algorithm, i.e. no valid security data are received, the method proceeds from step 2330 to step 2350, wherein only limited functionality is provided for the medical device 100. Preferably, only the functions for measuring the blood glucose level are provided in step 2350. In such a way it is prevented that the user of the medical device 100 chooses and configures by him an algorithm for determining the dose to be administered without advice of a health care professional. In such a way the risk is minimized that the user of the medical device 100 uses an algorithm which is not suitable for him. Nevertheless, the medical device 100 can be used as a blood glucose meter.

Preferably, only one activation key is used for unlocking and/or activating the processing functions provided by the determining unit 140. Alternatively, different security data are used which correspond to different authorization levels. For example, with a master security data or master key, which is preferably available for the health care professional, all predetermined functions, which are under control of the safety unit 1730, can be unlocked or/and activated. With a further security data or key, which is for a specific user, only specific predetermined functions can be unlocked or/and activated via the safety unit 1730.

Figure 24:
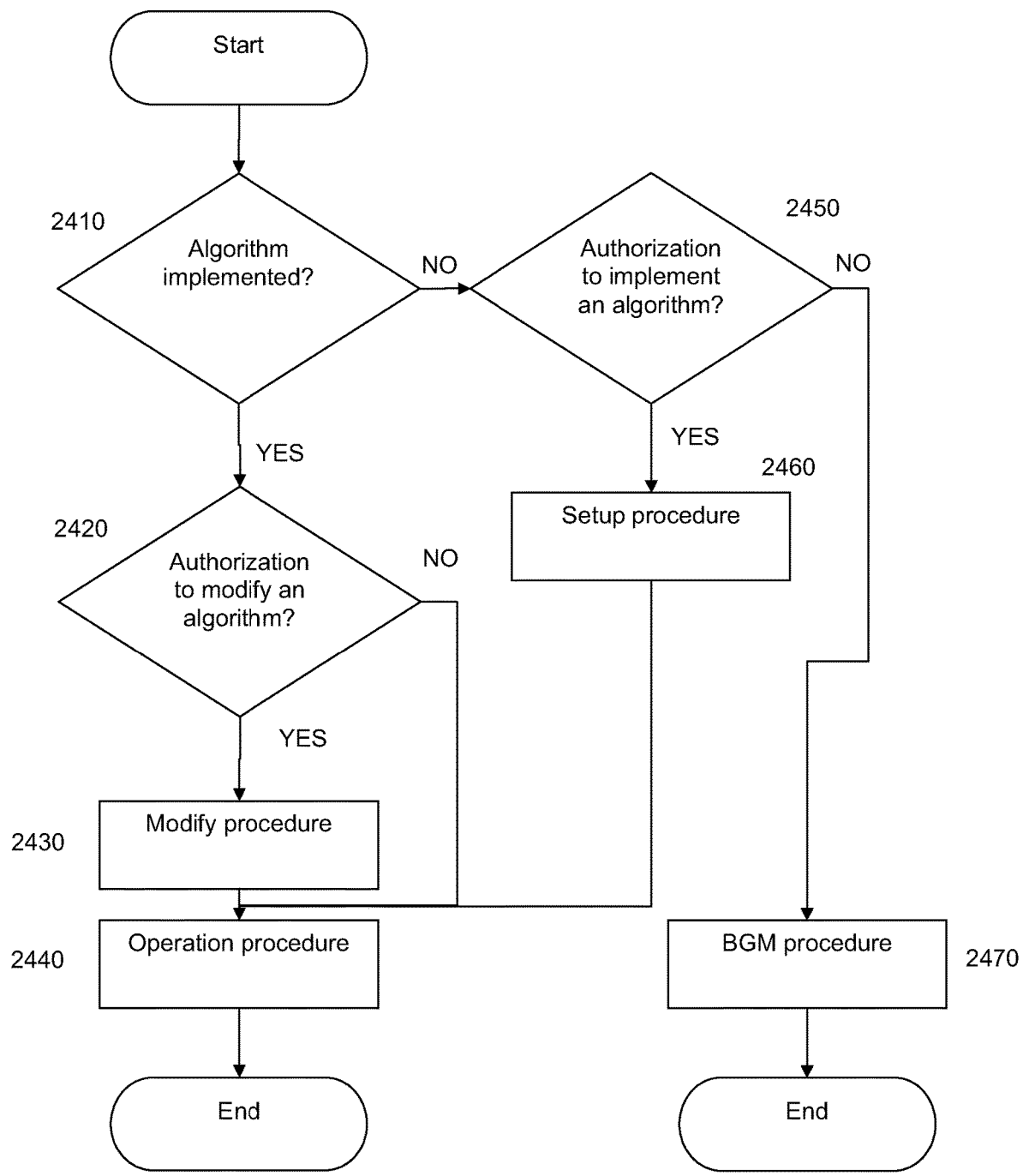
FIG. 24 is a flow diagram illustrating an alternative way for steps of the operating procedure shown in FIG. 23.

Such a user authorization via the security data allows an effective assignment of authorization levels to the respective groups. This provides the possibility that some specific parameter modifications still can be performed with such a normal user security data. In particular, this provides the possibility that data, which could be changed or modified by the user of the medical device 100, cannot be modified accidentally. According to a further alternative, several authorization levels, corresponding to several different security data and respective predetermined function groups, are provided, which are preferably assigned to specific user groups, such as health care professionals, users of medical device 100, emergency centers, specific call centers, etc. Preferably, this assignment is recorded in a configuration file, lookup table or database. These assignments are either defined by an authorized user or are factory settings FIG. 24 is a flow diagram illustrating an alternative way of the procedure shown in FIG. 23. In step 2410 it is detected whether an algorithm is already implemented. This step corresponds to the step 2310 already explained above for FIG. 23. If an algorithm has been already implemented correctly to determine a dose to be administered according to the needs and requirements of the user of the medical device 100, the method proceeds from step 2410 to step 2420. In step 2420 it is detected whether the authorization for modifying an algorithm, preferably the implemented algorithm, is given. For detecting, whether the authorization for modifying an algorithm or the implemented algorithm is given, the procedure as already explained for FIG. 21 is used.

In the case that it is detected in step 2420 that the authorization for modifying an algorithm or in particular the implemented algorithm is given, the method proceeds to step 2430. In this step the algorithm can be modified, which has already been explained in context with FIGS. 3 to 9.

Via such a configuration it is established that the method according to the preferred embodiment of the invention directly proceeds to the modifying procedure in the case that, e.g. a USB stick 1810 comprising, e.g. an HCP meter activation key, is connected to the receiving unit 170. Alternatively, any other kind of memory stick 170 or memory card is used.

In the case that an algorithm is already implemented, but no authorization for modifying an algorithm is detected, which might mean that no USB stick 1810 with HCP meter activation key is connected to the receiving unit 170, the method automatically proceeds to step 2440, which corresponds to the above described step 2320. As long as security data are provided to the medical device 100, full function mode is provided in step 2440. In the case that the security data are no longer provided, because, e.g. the USB stick 1810 has been disconnected, a limited functionality is provided in accordance with the safety unit 1730.

If it is detected in step 2410 that no algorithm is implemented, the method proceeds to step 2450 to detect whether the authorization to implement an algorithm is given. This corresponds to the procedure already described in context with FIG. 23. If the authorization is given, step 2450 proceeds to step 2460, wherein the setup procedure is started to select an algorithm, define a new algorithm or/and personalize the selected algorithm. When the setup procedure is finished and the algorithm is implemented correctly, step 2460 proceeds preferably to step 2440 for normal operation according to the validation data provided by the validating unit 1720. In the case that no authorization for implementing an algorithm is detected in step 2450, the method proceeds to step 2470 to provide preferably a procedure for measuring the blood glucose level.

Figure 25:
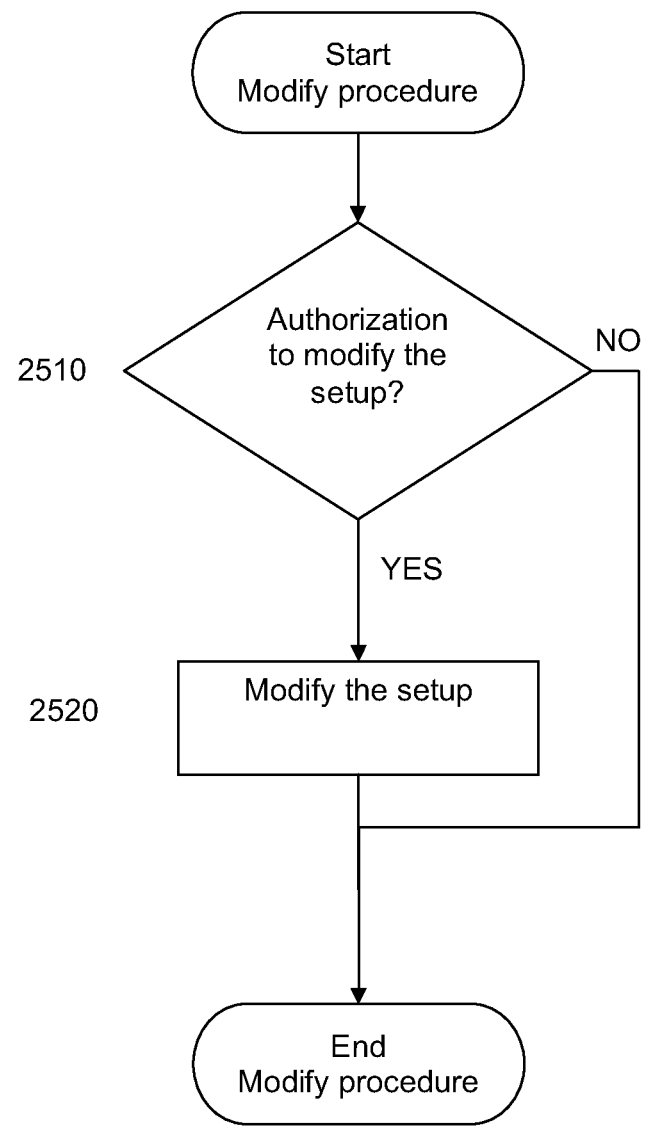
FIG. 25 is a flow diagram illustrating steps of the operating procedure shown in FIG. 24 in more detail.

FIG. 25 is a flow diagram illustrating the steps of an alternative version of the modified procedure according to the preferred embodiment of the invention. Alternatively to the procedure shown in FIG. 24, wherein the authorization for modifying the algorithm or other parameters stored in the storage unit 130 is performed before executing the modified procedure, the detecting of the authorization is performed within the modifying step. This gives the possibility to inform the user of the medical device 100 that the correct security data has to be provided if it is detected that no authorization is given for the time being. This information can be given visually via the display unit 160 and/or acoustically via a respective acoustic module. In the case that nevertheless no authorization for modifying the setup of the medical device 100 is detected, the modifying procedure preferably proceeds to the end indicating to the user that a modification of the setup has not been possible due to lack of authorization. Alternatively, the modified procedure may proceed with a modify functionality, which is limited to specific functions and parameters. These specific functions and parameters are either defined by an authorized user or are factory settings.

In the case that an authorization to modify the setup is detected in step 2510, the modify procedure proceeds to step 2520. In accordance with the detected authorization level, which is preferably determined via the validating unit 1720 in accordance with the received security data, the setup can be modified in step 2520. Depending on the authorization level, different functionality for modifying the setup, i.e. selecting an algorithm, modifying a new algorithm, personalizing an algorithm, changing parameters stored in the storage unit 130, etc., is provided under control of safety unit 1730. In the case that the correct security data for a master user are received, full functionality is provided for modifying the setup. In the case that the security data for a normal user of the medical device 100 is received, only limited functionality for modifying the setup of the medical device 100 is provided.

According to one alternative of the preferred embodiment of the invention one security data, such as a specific activation key is provided for all medical devices 100 of the same kind. According to another alternative version unique security data is provided for each medical device 100. Thus, only the unique security data corresponding to the respective medical device 100 can be used as an authorization code for unlocking and/executing specific functions of the medical device 100. Moreover, via the unique security data different medical devices 100 are distinguishable from each other and, therefore, can be addressed directly via the unique security data. According to another alternative of the preferred embodiment of the invention unique security data are provided for each HCP. This offers the possibility of assigning specific groups of medical devices 100 to one specific person in regard to the setup of the operation of the medical device 100.

Figure 26:
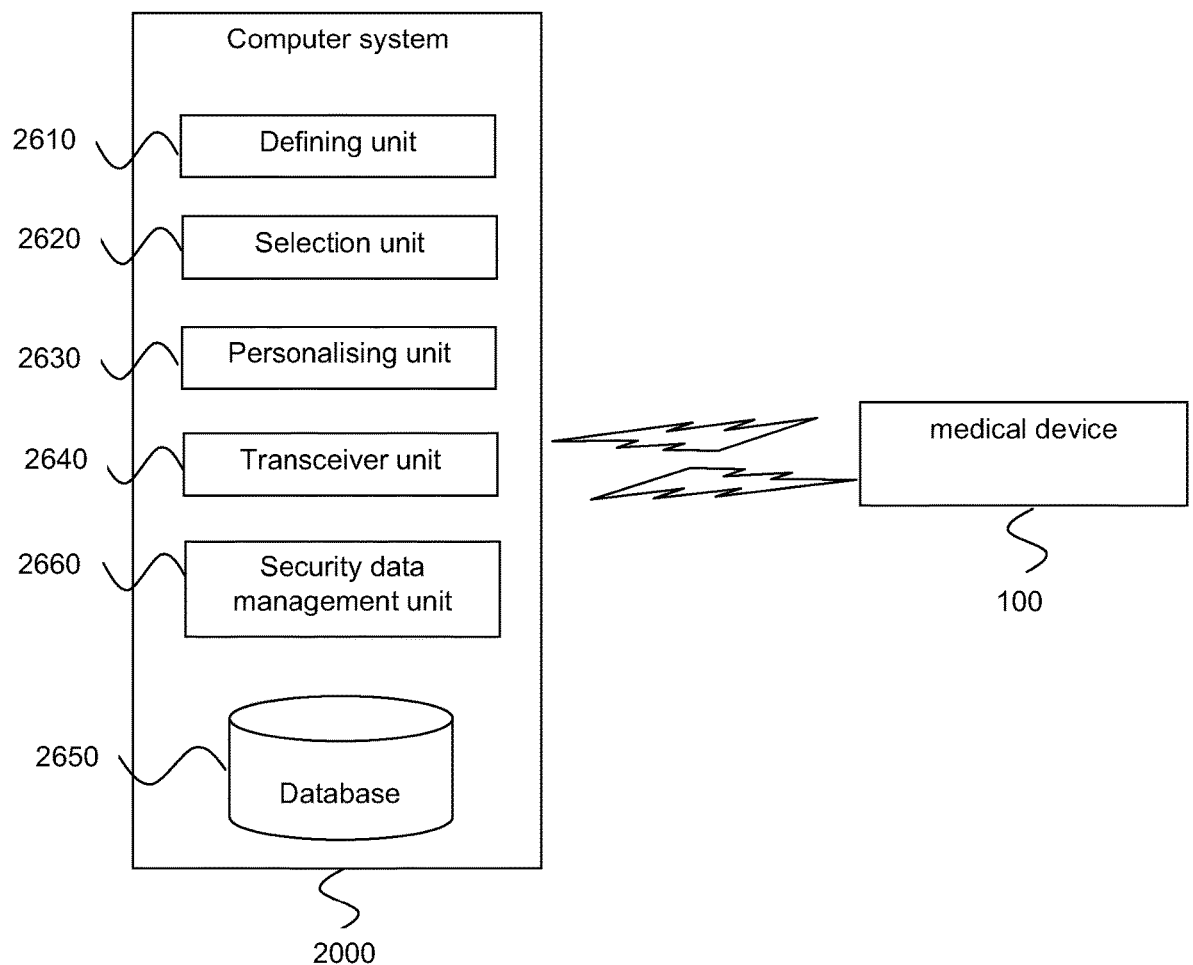
FIG. 26 is a further schematic diagram of the medical system shown in FIG. 20.

FIG. 26 is a schematic diagram of the medical system shown in FIG. 20 illustrating further details of the administration unit 2000.

FIG. 26 shows the functional units of the administration unit 2000 in more detail. Preferably, the administration unit 2000 comprises a defining unit 2610, a selection unit 2620, a personalization unit 2630, a transceiver unit 2640, a database 2650 and a security data management unit 2660. The defining unit 2610 is adapted to define new algorithms, also called profiles, for determining a dose to be administered. For this, the defining unit 2610 is connected to the database 2650, wherein predefined templates or elements are stored, which can be combined to new algorithms or profiles. The defining of new algorithms or profiles will be explained further below in more detail.

Furthermore, the selection unit 2620 is preferably configured for selecting an algorithm from a selection of predefined algorithms. These predefined algorithms are either factory settings and/or algorithms defined by the user of the administration unit 2000. To select an algorithm the selection unit 2020 is connected to the database 2650. Furthermore, the administration unit 2000 comprises a personalizing unit 2630, which is configured to personalize the selected algorithm as explained, e.g. in context with FIG. 9. The parameters selected during the personalization of the selected algorithm are preferably stored in the database 2650 in relation to the selected algorithm.

Preferably, the algorithms are defined via marked-up language, such as XML. Thus, the file representing a respective algorithm is rather small and, thus, can be easily transmitted via a wired or wireless connection. For this, the administration unit 2000 comprises a transceiver unit 2640, which, for example, is a network interface, Bluetooth interface, GSM interface or a WI-FI interface, etc. Thus, the data of the administration unit 2000 can be transmitted to the medical device 100 either if the medical device 100 is placed next to the administration unit 2000 or on a remote place. Preferably, the connection between the administration unit 2000 and the medical device 100 is a bidirectional connection so that data can also be transmitted from the medical device 100 to the administration device 2000. This allows transmitting the history of the measured blood glucose values and the doses administered to the administration unit 2000 for further analysis.

Furthermore, via the selection unit 2620 and the personalizing unit 2630 the medical device 100 can be configured via transceiver unit 2640 by directly accessing configuration files stored in the storage unit 130.

Additionally, the administration unit 2000 comprises a security data management unit 2660, which is configured to manage security data of one or more medical devices 100. In the case that for each medical device 100 unique security data are used, the security data management unit generates the security data together with the respective reference data for each of the medical devices 100 administrated with the administration unit 2000. Preferably, the reference data is then transmitted via the transceiver unit 2640 to the medical device 100. Alternatively, the reference data for each of the medical devices 100 is stored on a chip card which is then implemented in the medical device 100. Moreover, the security data management unit 2660 preferably is used to define the different authorization levels.

Alternatively, personal data such as health data as e.g. the blood glucose values are protectable via a user PIN which is also embedded in the authorization level concept. This ensures that these specific data can not be transmitted without the acknowledgment of the user of the device.

Alternatively, the administration unit 2000 is additionally used for remote monitoring of one or more medical devices 100. In particular, the administration unit 2000 is used to remote monitor the self-titration performed with the medical device 100. For this, the blood glucose value, the dates when blood glucose values have been determined, the doses administered, the events occurred, etc., are periodically requested by the administration unit 2000 and received from the medical device 100. If the analysis of the received data reveals that further actions have to be undertaken by the user of the administration unit 2000 in order to take a corrective action for the self-titration process, a message or an alert is transmitted to the medical device 100 from the administration unit 2000.

According to a further alternative the administration unit 2000 is additionally used for checking the functions of the medical device 100, for maintenance of the medical device 100 or for system updates for the medical device 100.

Moreover, the administration unit 2000 is a computer system.

As e.g. outlined for step 910 shown in FIG. 9, the personalization process also includes identifying the user of the medical device 100. Preferably, this is done by entering the name of the user. However, other data are used to alternatively identify the medical device 100 as belonging to a specific user. For example, graphics or images, which are displayed on the display unit 160, are used to uniquely identify the medical device 100. Moreover, acoustic signals can be used to distinguish one medical device 100 from other medical devices 100. In such a case specific sounds for pressing a button or for switching on the medical device 100 are selected during the personalization process. Moreover, according to a further alternative the medical device 100 comprises an electronic signature, such as the reference data, so that it can be electronically differentiated from other medical devices 100. In such a way it is avoided that parameters or algorithm data are transmitted to a wrong medical device 100 from the administration unit 2000.

As outlined in regard to the administration unit 2000, the reference data is generated by the administration unit 2000. Alternatively, the reference data is a factory setting, which is preferably unique for each medical device 100. Alternatively, the medical device 100 is identified via a PIN, which has to be entered by the user of the medical device 100 for switching on. Alternatively, the medical device 100 comprises a unit for scanning a fingerprint of the user of the medical device 100. Via the scanned fingerprint the medical device 100 is uniquely assigned to the user.

Such a PIN can be also used to protect predefined data stored in the storage unit 130.

Furthermore, the medical device 100 is distinguishable from other medical devices 100 via a unique signature or reference data, so that messages transmitted from the medical device 100 to the administration unit 2000 can be distinguished from messages received from other medical devices 100.

As outlined above, algorithms are used to determine the dose to be administered. These algorithms are either predefined or can be defined by a user of the medical device 100 or a user of the administration unit 2000.

Figure 27:
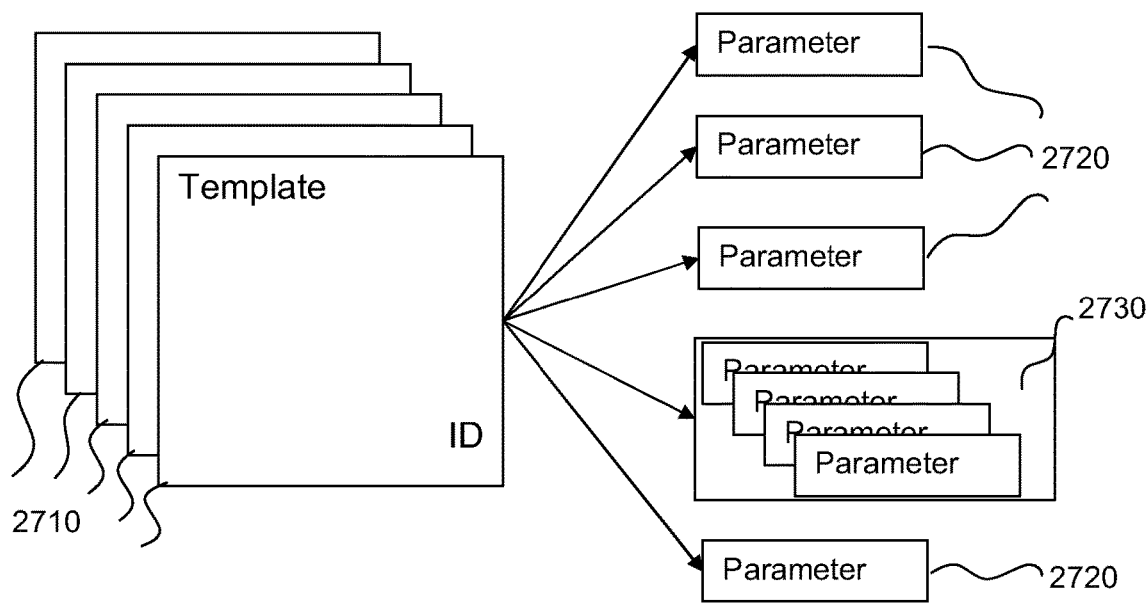
FIG. 27 is a schematic diagram illustrating the relation of the templates with the parameters and parameter sets according to a further embodiment of the invention.

Preferably, the algorithms or dose adjustment profiles are based on several components, such as templates and parameters. Preferably, algorithms are composed by one or more templates and one or more parameter sets. FIG. 27 is a schematic diagram illustrating the relation of the templates with the parameters and the parameter sets according to a preferred embodiment of the invention.

Preferably, the medical device 100 and/or the administration unit 2000 comprise a set of templates 2710, which are already predefined. Each template 2710 comprises preferably an ID, which uniquely identifies the template. Furthermore, each template comprises one or more parameters 2720 and/or one or more parameter sets 2730. These parameters are also identified via a unique identifier. Preferably, the relation between the template ID and the parameter IDs and parameter set IDs is stored.

Moreover, different templates are provided for different sections of the algorithm. Preferably, specific templates are provided for starting the algorithm, for the different phases of the algorithm, for terminating the algorithm, for low FBG rules, for hypoglycemic rules and for intervention rules. By composing the different templates via selecting one or more of the specific template a new algorithm can be composed, which comprises the startup of the algorithm, the different phases of the algorithm, the termination of the algorithm together with the low FBG rules, the hypoglycemia rules and the further intervention rules. Furthermore, the templates comprise predefined actions, such as displaying a set of parameters from which a specific parameter has to be selected for personalization, for requesting a value to be input by the user, for displaying a number of checkboxes, which have to be marked by the user, etc. Accordingly, the templates for initializing the algorithm preferably comprise a drop-down menu from which the starting value or current value of the dose is selected or offer a request to the user to enter the value manually. The template for the different phases of the algorithm comprise a drop-down menu or a request for manual input of the titration interval and the dose increase, which is made for each titration interval.

Preferably, the parameter and parameter sets define a specific initial dose value, a specific first dose increase step, a specific first time interval for increasing the dose, a specific first target blood glucose value, a specific second dose increase step, a specific second time interval for increasing the dose, a specific second target blood glucose value, etc., a specific low blood glucose threshold value, a specific low blood glucose dose decrease step, a specific hypoglycemic blood glucose threshold value, a specific hypoglycemic blood glucose dose decrease step, etc.

The templates for the rule comprise preferably a list of rules and actions, which are executed in the case that a specific event occurs. This also includes the input of information, such as e-mail addresses to which e.g. an alert is sent.

Figure 28:
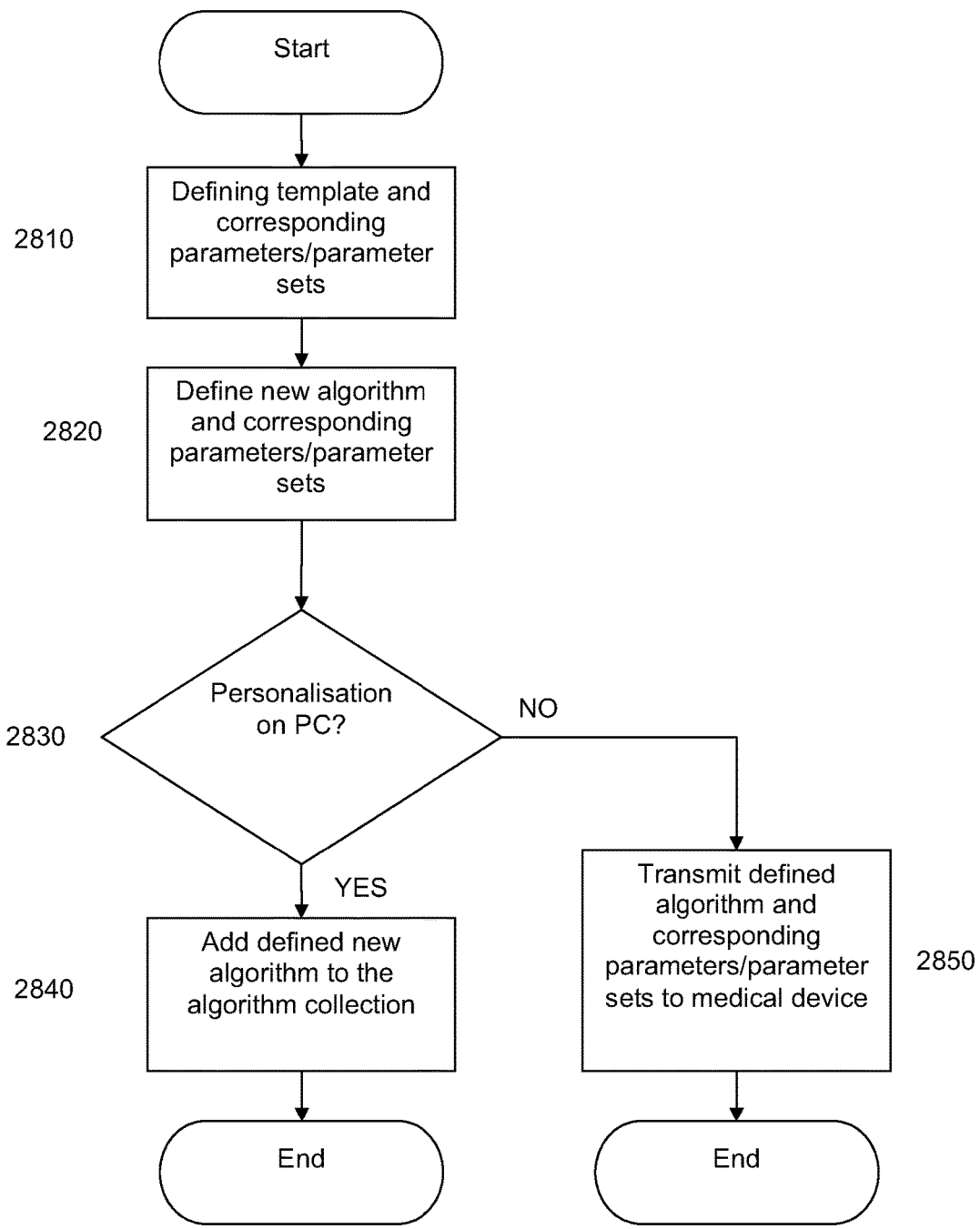
FIG. 28 is a flow diagram illustrating steps for defining templates according to a further embodiment of the invention.

FIG. 28 is a flow diagram illustrating steps for defining a new algorithm in more detail according to a preferred embodiment of the invention. Preferably, the flow diagram illustrates the steps for configuring a process for determining a dose of insulin to be set for glycemic control, wherein the dose is stepwise adapted. Preferably, the defining of such a new algorithm is performed in the administration unit 2000. Alternatively, the defining a new algorithm is performed in the medical device 100.

In step 2810 one or more templates are defined together with the corresponding parameters and parameter sets in the case that one or more further templates are needed for defining a new algorithm. This is in particular the case if the already available templates do not provide the necessary functionality needed for the new algorithm. Accordingly, a new template together with a new template ID is generated. Furthermore, one or more parameters 2720 or parameter sets 2730 are assigned to the template. When the defining of the template is finished, it is stored and forms part of the selection of the templates already defined.

In the next step 2820 the new algorithm is composed together with the corresponding parameters and parameter sets. Preferably, the new algorithm is defined by composing one or more templates to a new algorithm. In the case that templates have been chosen, wherein no specific parameters have been assigned to the respective parameters IDs, the respective parameters, such as titration interval, amount of dose increase, blood glucose target value, etc., have to be also input in step 2820 in order to define the new algorithm. Moreover, in step 2820 it is defined which parameters have to be personalized during the personalization process.

Thus, different algorithms are defined for stepwise adapting the dose, wherein preferably each of the different algorithms is based at least on a specific initial dose value, a specific time interval for increasing the dose, a specific dose increase step and a specific low blood glucose threshold value. Preferably, the algorithms are stored in the database 2650. Alternatively, the algorithms are stored in the storage unit 130.

When a specific algorithm is then selected out of the stored different algorithms based on specific requirements for stepwise adapting the dose the process proceeds with step 2830, wherein it is decided, whether the personalization of the new algorithm is performed on the administration unit 2000 or on the medical device 100. In the case that the personalization of the newly defined algorithm is performed in the administration device 2000, the process proceeds with step 2840 and stores the new algorithm and adds it to the collection of the already available algorithms. In the case that the algorithm is not personalized on the PC, e.g. as the newly defined algorithm shall be personalized later on the medical device 100, the process proceeds with step 2850. In step 2850 the newly defined algorithm is transmitted together with the corresponding parameters and parameter sets to the medical device 100.

Preferably each of the predefined algorithms corresponds to specific types of user, who are new to insulin and who are already experienced with insulin. Alternatively, the predefined algorithms or dose adjustment profiles corresponds to specific types of user, who shows specific habits and personal conditions. Moreover, different algorithms and dose adjustment profiles are provided for different insulin types and different diabetes types.

Accordingly, specific algorithms are designed to provide a safe starting dose range or to cover the fact that the FBG value is measured in the evening or that the dose has to be increased within a short time in order to achieve the final FBG target value or target range within a short time period.

Furthermore, specific algorithms are designed to cover the fact that the FBG value is measured in the morning but the dose is given in the evening.

Furthermore, specific algorithms provide longer titration intervals as the users have experience with diabetes and large or unexpected variations will not be expected within the long titration interval. Accordingly, the HCP or the person, who has the authorization to select an algorithm, can select one of the predetermined algorithms according to the above mentioned boundary conditions. In the case that the algorithm is selected in the administration unit 2000 and the corresponding algorithm is already stored in the medical device 100, it is only necessary to transmit the algorithm ID to the medical device 100 in order to define the selected algorithm. Alternatively, if the selected algorithm is not available in the medical device 100, the data of the selected algorithm is transmitted to the medical device 100. As mentioned above, preferably the algorithm is defined via marked-up language, such as XML, comprising the identifiers of the templates and parameters composing the selected algorithm. Thus, the amount of data to be transmitted is small and offers the possibility to use almost every transmission channel to transmit the data of the selected algorithm to the medical device 100.

According to another aspect of the invention the medical device 100 is capable to detect when the dose increase has to be terminated as the FBG value is close to the set final FBG target value. Preferably, the medical device 100 is capable to execute the steps of a method, which determines the termination of the dose increase based on glycemic events close to the final FBG target range.

Figure 29:
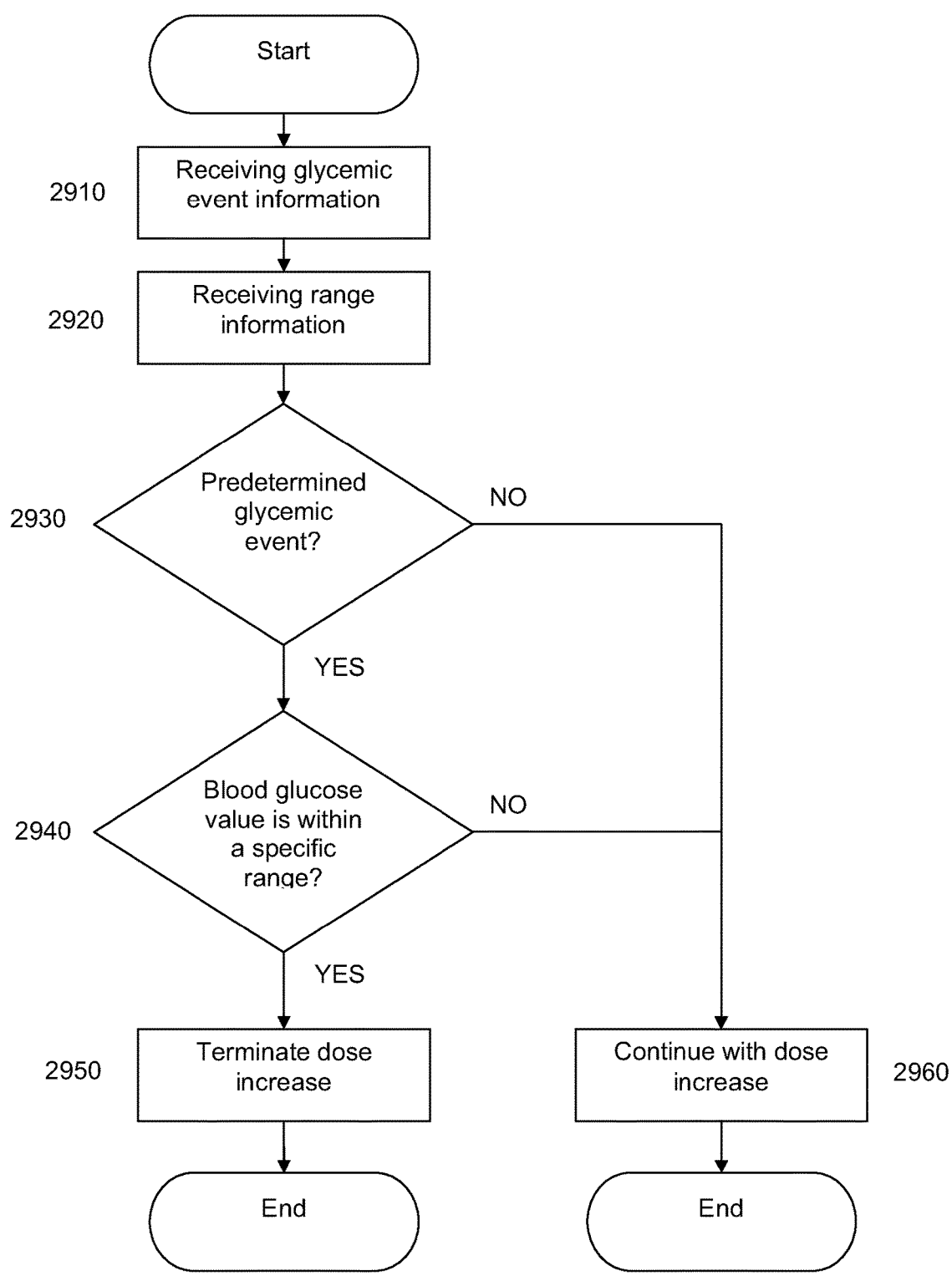
FIG. 29 is a flow diagram illustrating steps of a further operating procedure according to another preferred embodiment of the invention.

FIG. 29 is a flow diagram illustrating the method steps for determining a dose of insulin to be set for glycemic control according to another aspect of the preferred embodiment of the invention. In step 2910 glycemic event information is received. Preferably, glycemic event information is information on blood glucose levels. These blood glucose levels are preferably provided via the blood glucose values measured via the blood glucose measurement unit 110. Alternatively, the glycemic event information are blood glucose values input by the user via the user input unit 150. Furthermore, glycemic event information is also information indicating, whether or not a hypoglycemia has been experienced. Preferably, all glycemic event information is provided with a time stamp, i.e. the date when the glycemic event has been detected or measured. Moreover, the glycemic event information is preferably stored in the storage unit 130.

Preferably, additionally a set of parameters for determining a stepwise increase of the dose of insulin to be administered is received in step 2910. These parameters preferably define a titration interval and a specific amount by which the dose shall be increased within the titration interval.

Additionally, range information is received in step 2920, wherein the range information indicates that at least one specific blood glucose value is within a specific range in respect to a target blood glucose value. Preferably, the specific blood glucose value is measured by the blood glucose measurement unit 110. Moreover, the target blood glucose value is preferably provided by the selected algorithm, which is executed by the medical device 100. This target blood glucose value is either a final blood glucose target value for the complete algorithm or a target blood glucose value for a specific phase of the algorithm. Moreover, the specific range is a value defined for each phase of the selected algorithm or is a general value valid for this selected algorithm or, alternatively, for all available algorithms.

Preferably, the at least one specific blood glucose value is the actual FBG value determined by the blood glucose measurement unit 110. Alternatively, the at least one blood glucose value is the actual measured FBG value and the FBG value measured at the previous titration. If the actual blood glucose value or in the later case both FBG values are within the predefined range in respect to the target blood glucose value, this is indicated by the range information. Preferably, the range information is a bit wherein the value "1" indicates that the at least one specific blood glucose value is within the specific range in respect to the blood glucose value and the value "0" indicates that the at least one specific blood glucose value is not within the specific range. Alternatively, the range information is Boolean. Preferably, the range information is determined by determining unit 140.

In step 2930 it is determined, whether a predetermined glycemic event has occurred within a predetermined time interval. If such a predetermined glycemic event is defined as a hypoglycemia occurred within the last titration interval and such as hypoglycemia occurred within the last titration interval, the method proceeds from step 2930 to 2940, wherein the range information is checked.

If the range information indicates that at least one specific blood glucose value is within a specific range in respect to the target blood glucose value, the method proceeds from step 2940 to step 2950, wherein the increasing of the dose according to the set of parameters is determined. Preferably, the selected algorithm is terminated and it is indicated to the user, preferably via display information on the user display 160, that the algorithm has been terminated due to the glycemic events. Alternatively, if the target blood glucose value is the target blood glucose value of one of the phases of the algorithm, whereby one or more further phases follow this phase, the phase belonging to the target blood glucose value is terminated and the subsequent phase is started. In the case that it is determined that no predetermined glycemic event occurred within a predetermined time interval, the method proceeds from step 2930 to step 2960, wherein it is continued to increase the dose. Furthermore, if the blood glucose value is not within the specific range, step 2940 proceeds also to step 2960.

In the case that the glycemic event information is an information about a specific pattern of glycemic events, such as one or more hypoglycemia within one or more titration intervals or an hypoglycemia after a dose increase and one FBG value above the specific range after a dose decrease, the time interval defined by this pattern preferably corresponds with the time interval, which is taken for choosing the specific blood glucose values needed for determining the range information.

Figure 30A:
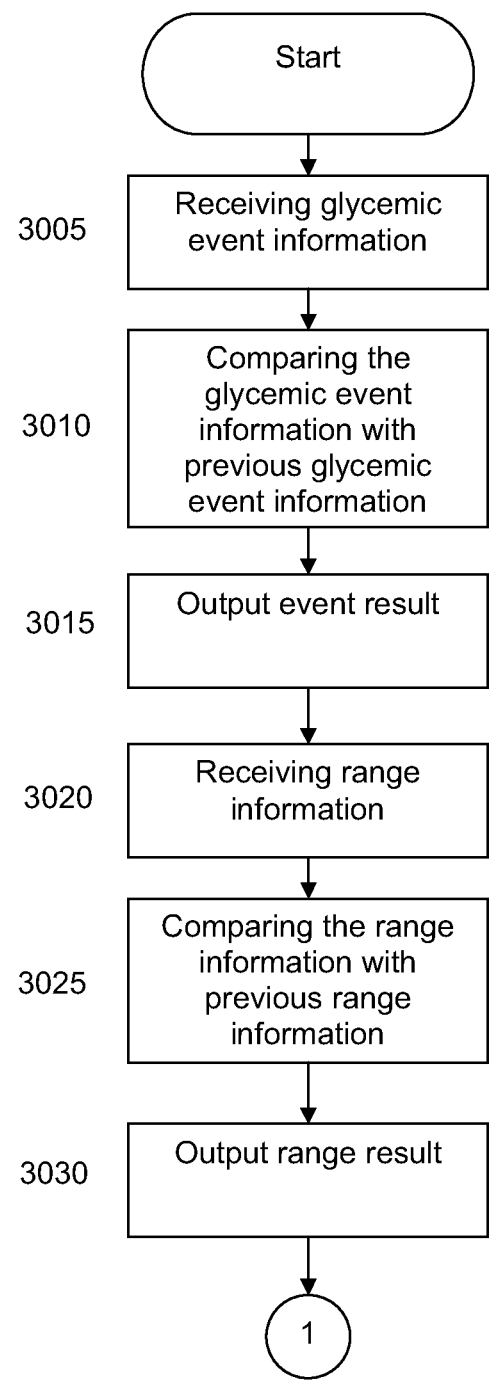
FIGS. 30a and 30b show a flow diagram illustrating alternative steps of the operating procedure as shown in FIG. 29.
Figure 30B:
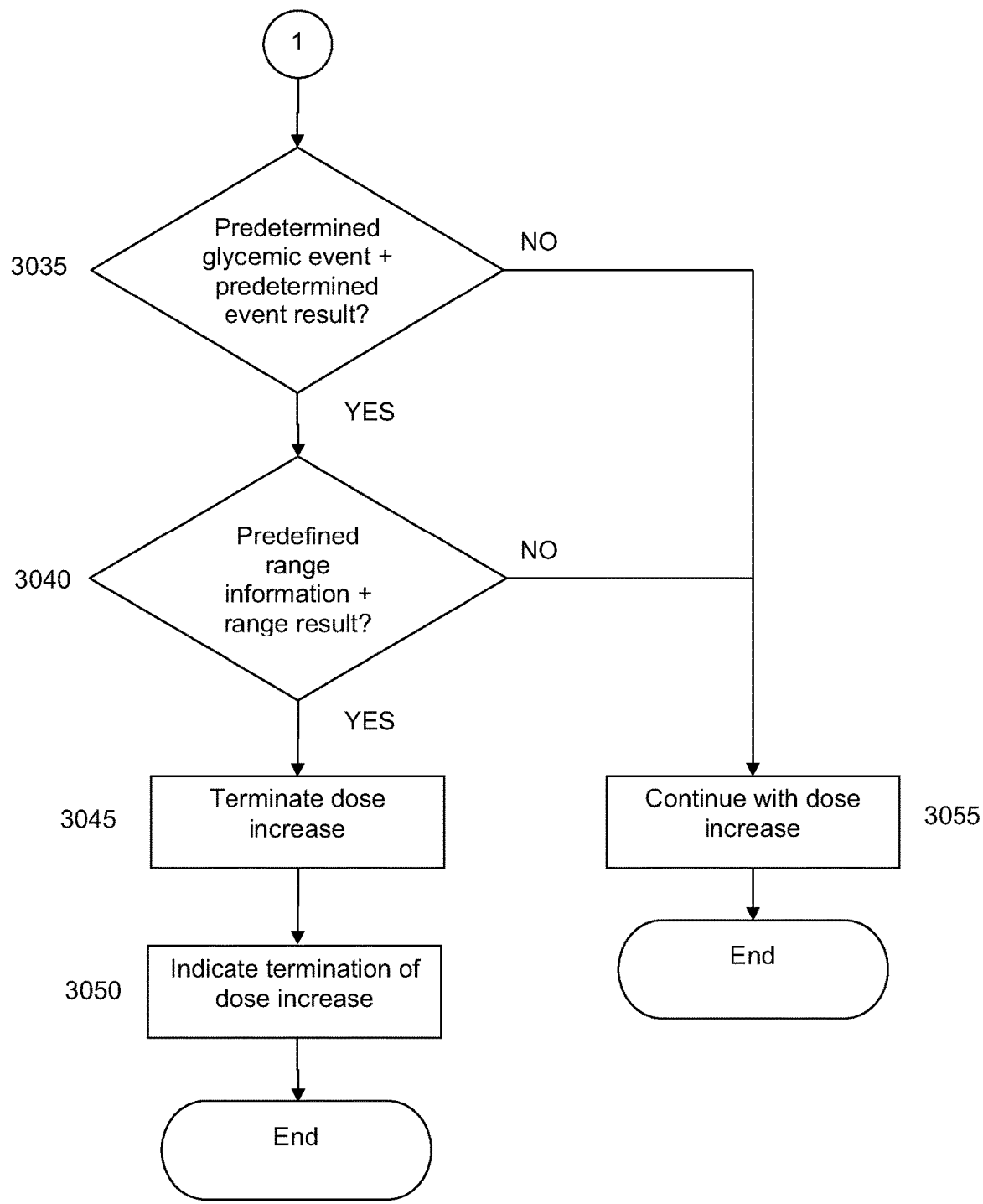

FIGS. 30a and 30b show a flow diagram illustrating the method shown in FIG. 29 comprising further steps. In step 3005 glycemic event information is received as already outlined in regard to step 2910. In the further step 3010 the received glycemic event information is compared with previously received glycemic event information. In the case that the glycemic event information is information on the frequency of hypoglycemia within a specific time interval, such as e.g. the titration interval, the frequency of the actual determined frequency of hypoglycemia is compared with the frequency of hypoglycemia within a previous time interval. In the case that the glycemic event information is information on the blood glucose level, the respective blood glucose values are compared. Furthermore, in the case that the glycemic event information is a specific pattern for, e.g. the distribution of blood glucose values, the different patterns receives are compared. By comparing the received glycemic event information with previously received glycemic event information it is possible to determine, whether the development of the blood glucose level is still within the objective of the treatment. By comparing the different glycemic event information it can be analyzed by example, whether there is a tendency that the blood glucose level falls below the final blood glucose target level or whether the actual state is that the measured blood glucose values are almost in no correlation with the dose administered or whether a hypoglycemia is a single event and seems not to influence the further treatment.

Based on the comparing step 3010 an event result is output. Preferably, the event result is information indicating, whether the glycemic event information has to be considered according to one or more predetermined rules for the continuation of the selected algorithm. In that case the event result is a bit represented by values "1" or "0", a flag or a Boolean value.

In step 3020 range information is received as already outlined in regard to step 2920. This range information is compared with previously received range information in step 3025. By comparing the received range information with the previously received range information, preferably the progress of the blood glucose level towards the final blood glucose target value is analyzed. In the case that the range information is an information indicating, whether the measured blood glucose value is a blood glucose value above the blood glucose target range, within the blood glucose target range or below the blood glucose target range, a tendency of the timely development of the blood glucose value can be determined based on the comparison in step 3025. As a result of such a comparison, a range result is output in step 3030. Preferably, the range result is information indicating, whether the range information received in step 3020 is significant range information and, thus, has to be considered in accordance with one or more predetermined rules by determining, whether the selected algorithm is continued or terminated.

In step 3035 it is detected, whether a predetermined glycemic event has occurred within an predetermined interval and whether the event result corresponds to a predetermined event result. In the case that no predetermined glycemic event has occurred and, thus, no predetermined event has been identified, the method directly proceeds to step 3055, wherein the medical device 100 continues to determine the dose to be administered according to the selected algorithm. This includes also that the dose is increased according to the algorithm within the titration interval.

In the case that a predetermined glycemic event has occurred but no predetermined event result has been identified, e.g. the hypoglycemia is only a single event with no significance, step 3035 also proceeds to step 3055. In the case that a predetermined event result has been identified, i.e. the frequency of hypoglycemia within a titration interval has been increased in regard to a preceding interval, step 3035 proceeds to step 3040.

In an alternative version step 3035 directly proceeds to step 3045, wherein the increasing of the dose according to the set of parameters is terminated. Skipping step 3040 is preferably executed if the event result indicates a development of glycemic events, which may have impact on the health of the user of the medical device 100. This might be if the event result corresponds to a frequency of hypoglycemia within a titration interval and this frequency is beyond a predetermined threshold value. This would indicate that the current dose of insulin might be too high or that any other effects interfere with the insulin treatment which have to be carefully analyzed by HCP. In such a case an alert is preferably transmitted to an HCP via the interface 170.

In the case that step 3035 proceeds to step 3040 it is detected whether predetermined range information is output. If e.g. the range information indicates that the blood glucose value is above the blood glucose target range, step 3040 proceeds to step 3055. Moreover, if the specific range result indicates that e.g. the blood glucose value is now for the first time within the blood glucose target range, it is preferably also decided in step 3040 to proceed to step 3055. In the case that the specific range result indicates that the blood glucose value shows an erratic, unpredictable or unstable distribution within or around the blood glucose target range within one or more titration intervals, it is determined in step 3040 to proceed to step 3045. Alternatively, if the range result corresponds to the fact that the blood glucose value does not show a further progress towards the blood glucose target value within the blood glucose target range, it is also determined in step 3040 to proceed to step 3045 in order to terminate the process of the dose increase.

When the selected algorithm for determining the dose to be administered has been terminated on the above described decisions in step 3035 and 3040, this termination is indicated in step 3050. Preferably, this is shown to the user of the medical device 100 on the display of the user display 150. Alternatively, an additional alert or message is sent to an HCP or an emergency center via interface 170. Alternatively, an acoustic signal is produced for informing the user of the medical device 100 about the termination of the dose increase.

Figure 31A:
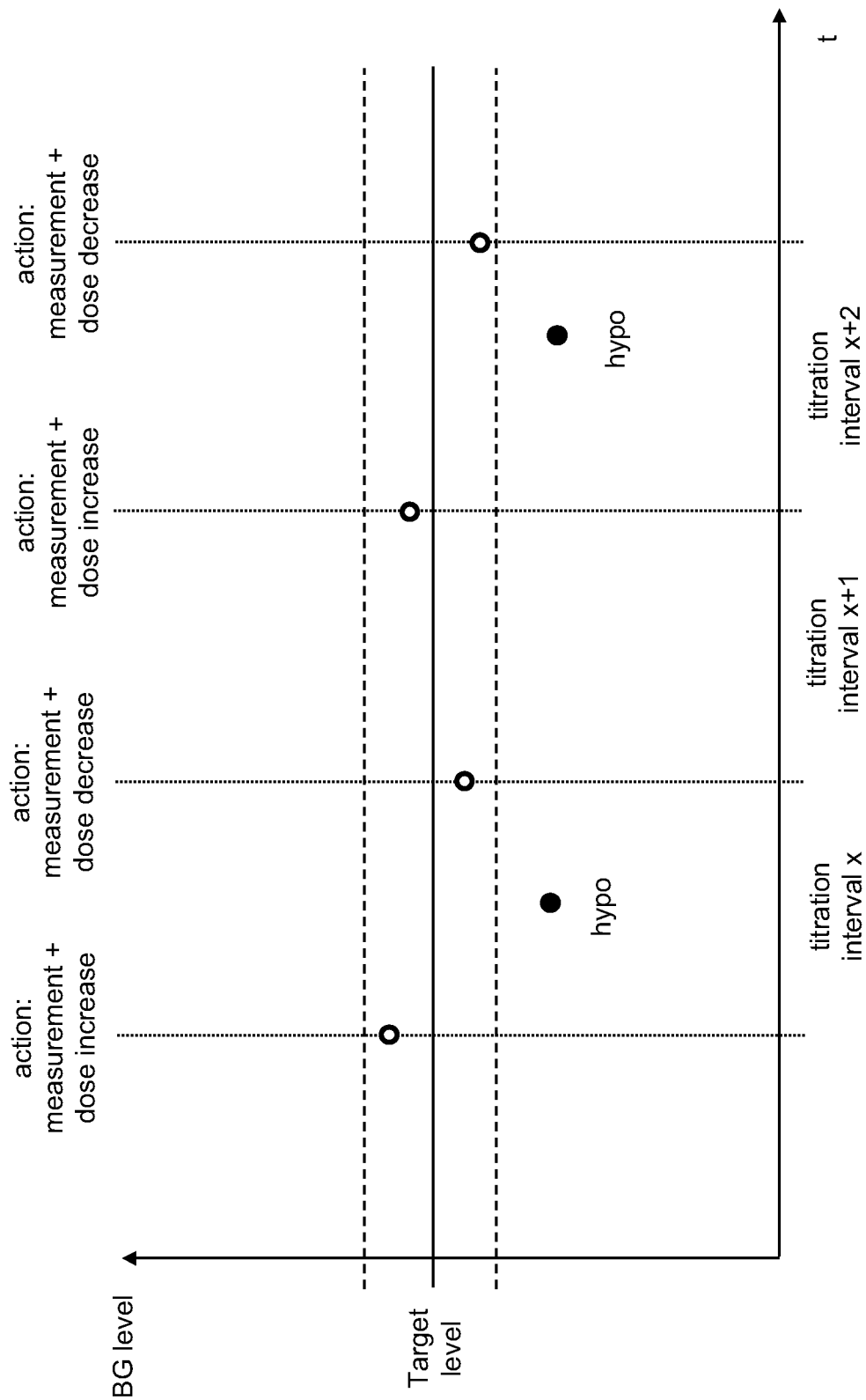
FIGS. 31a and 31b are schematic diagrams showing exemplarily a chronological sequence of glycemic events and dose target values according to a further preferred embodiment of the invention.

FIG. 31*a* is a schematic diagram showing exemplarily a chronological sequence of glycemic events and measured blood glucose value in dependence of the doses administered. The abscissa shows the time elapsed, whereby the ordinate shows the blood glucose level in respect to a blood glucose target level, which has been marked with a solid line. The blood glucose target range extends preferably below and above the blood glucose target level and is indicated via horizontal dashed lines. Dotted vertical lines indicate the event of a titration so that two subsequent dotted vertical lines form a titration interval.

In FIG. 31*a* the titration intervals x, x+1 and x+2 are shown. The circles on the vertical dotted line indicate the FBG value measured during the titration. As can be seen all measured FBG values are within the blood glucose target range. However, in titration interval x and titration interval x+2 hypoglycemia has been detected, which are marked by dots. Based on the situation shown in FIG. 31*a* the event information preferably is information on the hypoglycemia in the titration interval x+2. Furthermore, by comparing previous glycemic event information it is detected that also a hypoglycemia has been reported in titration interval x. Accordingly, repeated hypoglycemia has occurred and if repeatedly reported hypoglycemia is a predefined event, which has been e.g. classified as significant, an respective event result is output indicating that the comparing step has identified a significant event which has to be considered in the further processing steps such as e.g. step 3035.

Alternatively, the hypoglycemic event may be additionally correlated with the doses administered. In the case shown in FIG. 31*a* such as correlation of the received glycemic event information and previous glycemic event information would reveal that there is a correlation in regard to the dose increase. In the case that such a correlation is detected in the comparing step 3010, a corresponding event result is output indicating that a significant event has been detected, which has to be considered during the further processing e.g. in step 3035.

The range information received in the last titration shown in FIG. 31*a* corresponds to the information that the blood glucose value is within the blood glucose target range. As can be seen in FIG. 31*a* the FBG values are within the blood glucose target range. In the case that the range information refers only to the FBG value, the received range information and the range information of the previous last three titrations would indicate that the FBG values are within the target range. Comparing the range information with the previous range information would thus produce the result that the FBG value is continuously within the target range. In the case that one of the predetermined range results being considered as being significant is the result of an FBG value being continuously within the range, the range result output would thus be an information, such as an identifier, flag or bit indicating that a significant range result has been detected.

In the case that the range information not only refers to the FBG values but also to all blood glucose values measured and reported, the comparing step 3025 would produce the result that the blood glucose value is unstable over several titration intervals. In the case that one of the predetermined range results corresponds to such an unstable state, which is identified as being significant, the range result output in step 3030 would also indicate that a significant result has been detected.

Preferably, it is also indicated in step 3050 based on which predetermined range result the dose increase has been terminated.

According to another alternative in step 3045 not the complete algorithm is terminated but only the current phase of the algorithm. In a subsequent step the next phase of the algorithm is initiated, wherein either the titration interval is longer than in the previous phase or the dose increase is lower than in the previous phase. Thus, the subsequent phase would provide a finer control of the blood glucose value.

Figure 31B:
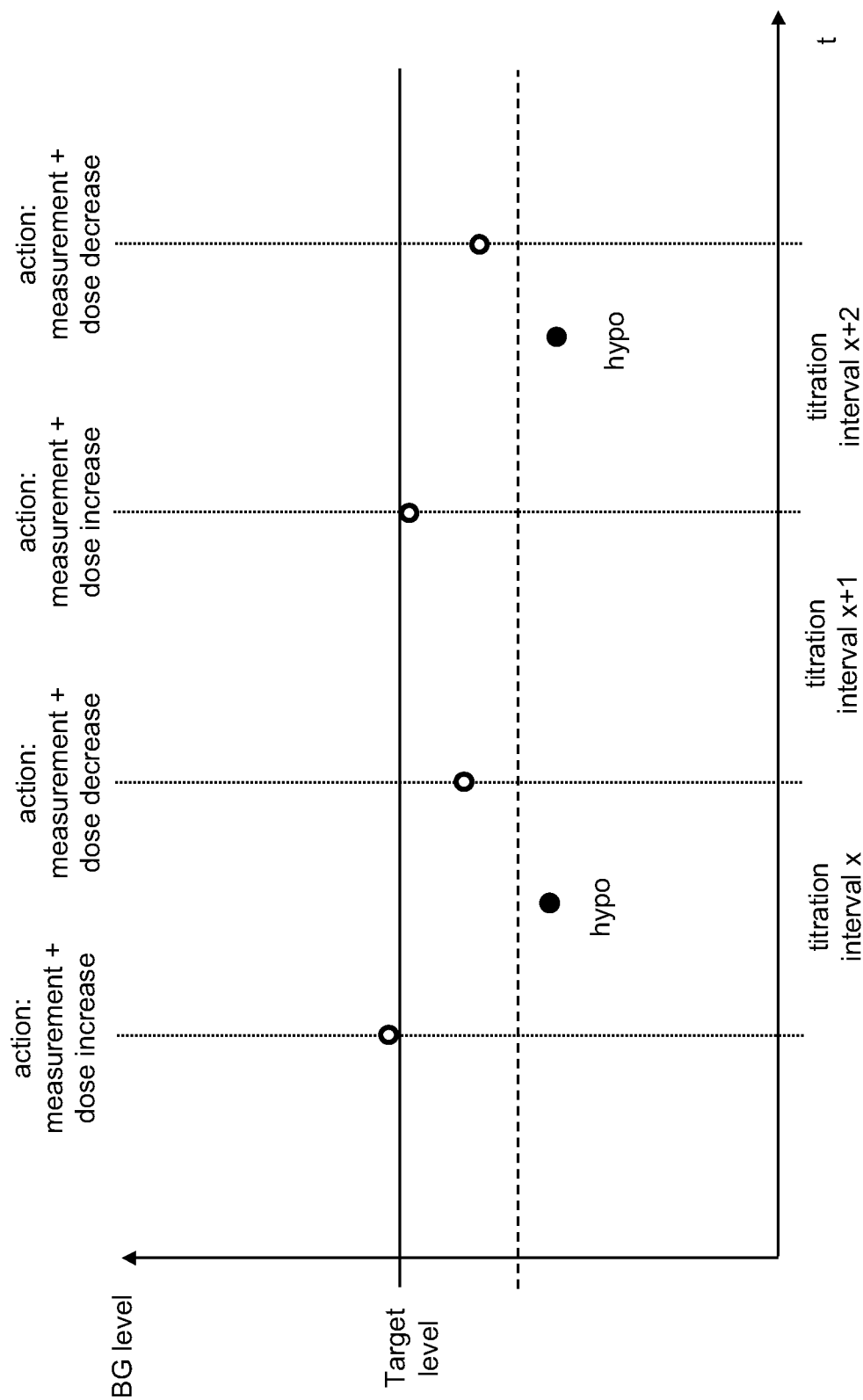

FIG. 31b is like FIG. 31a a schematic diagram showing exemplarily a chronological sequence of glycemic events and measured blood glucose values in dependence of the doses administered. Like shown in FIG. 31a, the abscissa shows the time elapsed, whereby the ordinate shows the blood glucose level in respect to a blood glucose target level.

In FIG. 31b an alternative definition for the blood glucose target level and the blood glucose target range is given. In this alternative definition the target level defines the upper limit of the target range. The lower limit of the target range is defined by a lower limit target value. In a further alternative version the blood glucose target level defines the lower limit of the blood glucose target range and the upper limit of the blood glucose target range is defined by an upper limit blood glucose target value.

As already described for FIG. 31a, three titration intervals x, x+1 and x+2 are shown also in FIG. 31b. The circles on the vertical dotted line indicate the FBG value measured for the titration. As can be seen, the first measurement value is outside the target range. As no hypoglycemic event has been detected before the titration interval x, it is determined that the dose is increased. During the titration interval x the increased dose is administered. In the case that the titration interval is e.g. three days the next measurement will be performed three days after the previous measurement. Within these three days a hypoglycemia is detected and stored in the medical device 100. In the case that such a hypoglycemia is a predetermined or predefined glycemic event, this glycemic event information is compared with previous glycemic event information in step 3010. Then a new measurement is performed after the titration interval x. Based on the new FBG value measured and the glycemic event information medical device 100 proceeds as already described in regard to FIG. 31a.

Figure 32:
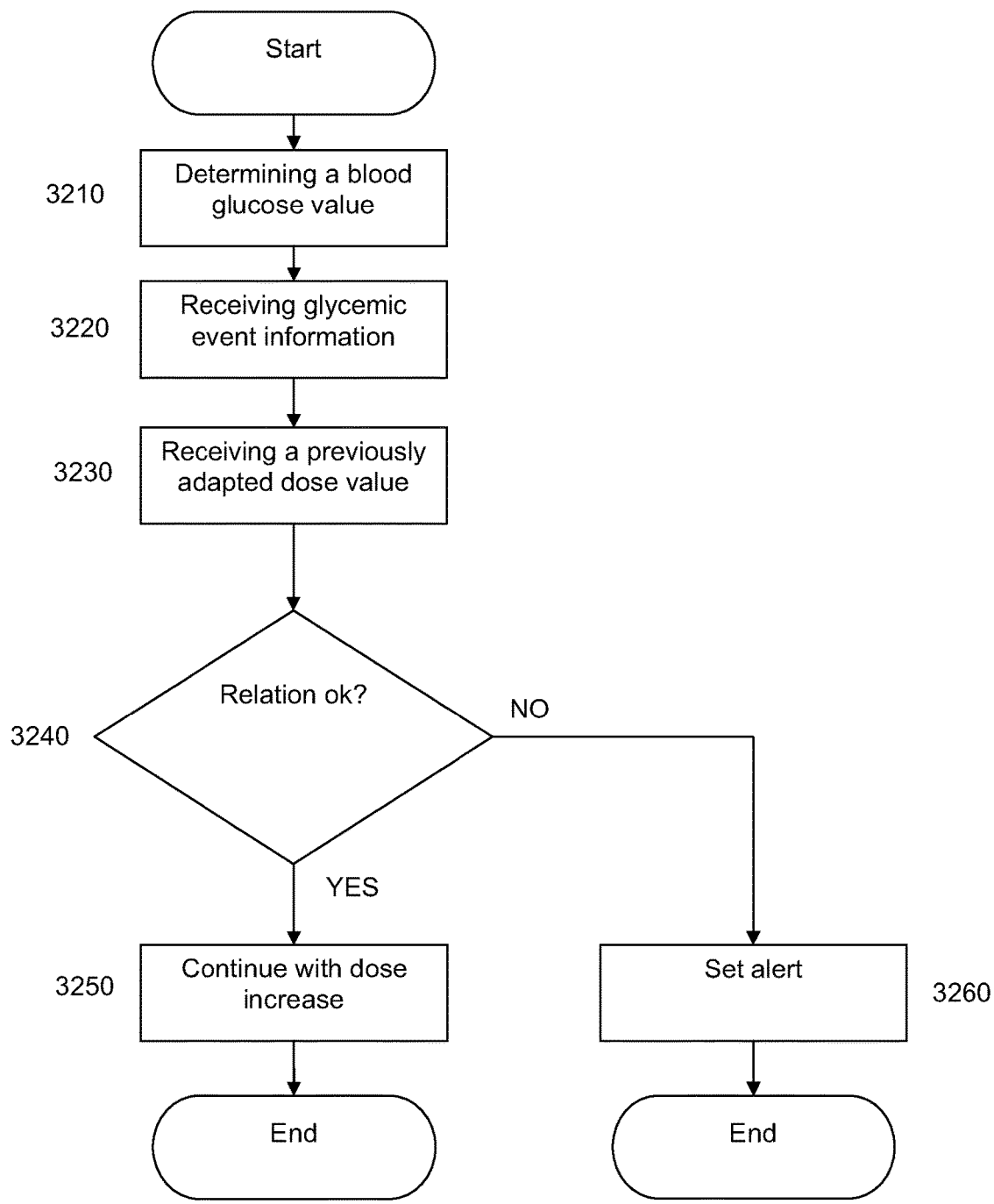
FIG. 32 is a flow diagram illustrating steps of another operating procedure according to still another preferred embodiment of the invention.

FIG. 32 is a flow diagram illustrating a method for determining a dose of insulin to be administered for glycemic control according to still another preferred embodiment of the invention. The method for determining a dose of insulin to be administered for glycemic control, wherein the dose is stepwise adapted, provides a first step 3210, wherein blood glucose value is determined. Preferably, the blood glucose value is determined by blood glucose measurement unit 110.

In step 3220 glycemic event information is received in respect to a predetermined glycemic event, wherein the predetermined glycemic event occurred within a predetermined time interval. Preferably, the glycemic event information is information about hypoglycemia or a low blood glucose value. This information is either received via the blood glucose measurement unit 110 or via user input unit 150 or electronically via interface 170. Moreover, a previously adapted dose value stored in the storage unit 130 is received. Based on at least a blood glucose value, the glycemic event information and the previously adapted dose, an alert is set, wherein the alert indicates that the blood glucose value and the predetermined glycemic event are not in a specified relation to the previously adapted dose value.

Preferably, in step 3240 the relation of the blood glucose value and the predetermined glycemic event to the previously adapted dose value is determined. Preferably, the specified relation is an absolute relation between a determined blood glucose value and the previously adapted dose value. According to a preferred version a lookup table, file or database is provided, wherein specific blood glucose value ranges are set in correlation with dose values administered. Accordingly, it is determined in step 3240, whether the relation between the determined blood glucose value and the received previously adapted dose value corresponds to the relation provided by the lookup table, file or database. In the case that the relation of the determined blood glucose value to the previously adapted dose value corresponds to that in the lookup table, file or database, step 3240 proceeds to step 3250, wherein the selected algorithm proceeds with the dose increase according to the parameters set for the selected algorithm. In the case that the relation of the determined blood glucose value does not correspond to the previously adapted dose value as specified in the lookup table, file or database, because e.g. the blood glucose value is much lower than defined in the lookup table, file or database and additionally an hypoglycemia has been detected or reported, then step 3240 proceeds to step 3260, wherein an alert is set. Preferably, in step 3260 not only an alert is set but also e.g. transmitted via interface 170 to HCP or to an emergency center. Additionally or alternatively, a respective alert is displayed on the display unit 150.

Alternatively, if the blood glucose value is much higher in relation to the previously adapted dose value than defined in the lookup table, file or database and additionally a low blood glucose value or a hypoglycemia has been detected or reported, step 3240 also proceeds to step 3260.

In a further alternative additionally previous blood glucose values and additional previously adapted dose values are received from the storage unit 130 in order to determined the relation between blood glucose values, the predetermined glycemic event and the previously adapted dose values. In such as case, preferably not only an absolute relation is taken into consideration, but also a relative relation, wherein a timely correlation between the blood glucose values and the respective adapted dose values is determined. In such a case a specific relation is preferably a relation, wherein the blood glucose value decreases if the dose adapted increases and opposite. If the relation of the blood glucose values does not show such a relation with the adapted doses and additionally a hypoglycemic event has been detected or reported, step 3240 proceeds to step 3260. In the case that a timely correlation between the blood glucose values and the adapted dose values is determined, step 3240 alternatively also proceeds to step 3260 if no glycemic event information has been received.

According to a further alternative the blood glucose value determined in step 3210 is a FBG value. Furthermore, the glycemic event information received in step 3220 is the FBG value determined during a previous titration. Moreover, the previously adapted dose value received in step 3230 is the dose value adapted during the titration of the previously FBG value of step 3220. For this alternative the specific relation is preferably a correlation of the previous FBG value and the determined FBG value with the previously adapted dose value and the dose value to be adapted in the actual titration. Preferably, a specific range for this correlation is defined. If the determined value for the correlation is outside of this range, then step 3240 proceeds to step 3260. In the case that the correlation value for the blood glucose values and the adapted dose value is within the specified correlation range, then step 3240 proceeds to step 3250. According to a further alternative not only two blood glucose values and two dose values are chosen for determining the correlation but more than two values.

Preferably, step 3260 additionally comprises stopping to further increase the dose, wherein the stopping of the further increase of the dose is triggered by the alert. Preferably, a predetermined user input is needed to activate the stopping of the further increase of the dose. Moreover, the stopping of the further increase of the dose is deactivated via a predetermined user input according to a further alternative. Furthermore, step 3260 preferably comprises the step of creating retest information, wherein the creating of the retest information is triggered by the alert. Preferably, the retest information is displayed on the display unit and indicates the user of the medical device 100 to initiate a retest of the blood glucose value within a predetermined time. Additionally, preferably predefined safety instructions are displayed on the display together with the alert.

For determining a dose of insulin to be administered for glycemic control, the medical device 100 comprises, as shown in FIG. 1, a blood glucose measurement unit 110 or also called blood glucose determining unit 110. The blood glucose measurement unit 110 is adapted to determine a blood glucose value as already explained above in regard to FIG. 1. Moreover, the medical device 100 comprises a storage unit 130, which is adapted to store previously adapted dose values and preferably also glycemic event information. Additionally, medical device 100 comprises receiving unit 120, which is arranged to receive glycemic event information in respect to a predetermined glycemic event within a predetermined time interval and for receiving the previously adapted dose value stored in a storage unit.

Furthermore, the medical device 100 comprises a determining unit 140, also referred to as adapting means, which is arranged to stepwise adapting the dose according to the output of the receiving unit 120 and the blood glucose measurement unit 110. Additionally, the medical device 100 comprises an alert unit adapted to set an alert. Preferably, the alert unit is a functional part of the determining unit 140. The alert unit preferably sets an alert based on at least the blood glucose value, the glycemic event information and the previously adapted dose, wherein the alert unit is adapted to create the alert indicating that the blood glucose value and the predetermined glycemic event are not in a specified relation to the previously adapted dose value.

Preferably, the interface 170 receives instructions for defining the specified relation between the blood glucose value and the predetermined glycemic event and the previously adapted dose value by providing at least one specified blood glucose value range and at least one specific predetermined glycemic event, both corresponding to at least one specific dose value. Preferably, the storage unit 130 stores the at least one specified blood glucose value range and the at least one specified predetermined glycemic event. In the case that the alter unit sets an alert, the determining unit 140 stops the selected algorithm. Preferably, the selected algorithm is not terminated so that the execution of the selected algorithm can be continued, preferably via a user input or via a signal received via interface 170. Preferably, specified relations for setting an alert are e.g. that the dose values increase and the FBG values do not decrease, that the dose values increase but the FBG values decrease faster than specified by a specific parameter, the dose values decrease and the FBG values also decrease. Further specified relations are that hypoglycemia is detected although the FBG values are high or that the dose values are high, the FBG values are high and hypoglycemia is detected.

Medical device 100 preferably also comprises a message generation unit, wherein preferably the message generation unit is a functional unit of the determining unit 140. Preferably, the message generation unit is arranged to create retest information. Preferably, the message generation unit receives the alert signal and generates the retest information based on the alert signal for initiating a retest of the blood glucose value within a predetermined time. Alternatively, not only a visual alert is set via the display unit 160 but also an acoustic alert is set via an acoustic module. Additionally, as already outlined above, an alert message is transmitted to a predetermined destination via interface 170. Preferably, the alert message comprises at least information indicating that the blood glucose value and the predetermined glycemic event are not in a specified relation to the previously adapted dose value. Thus, if the predetermined destination is an HCP, the HCP is able to initiate further actions.

In addition to the titration methods described above, which can be applied to basal, premixed and mealtime insulin, a further preferred embodiment of the invention is described in the following wherein the medical device 100 provides preferably additionally a method for dose adjustment for a mealtime. For this, the medical device 100 comprises the storage unit 130 arranged to store information on an initial dose of insulin and to store information on a blood glucose level measured after the initial dose of insulin was administered and after specific food was consumed, and the determining unit 140 arranged to determine a subsequent dose of insulin to be administered before the specific food is consumed based at least on said information on the initial dose of insulin and said information on the blood glucose level.

Preferably, the storage unit 130 is further arranged to store information on the specific food consumed, wherein the information on specific food consumed comprises data relevant for the glycemic control. The medical device 100 receives food information either via user input unit 150 or via interface 170. Based on this food information and based on a previously determined sensitivity on specific food and on specific insulin, the dose of insulin to be administered is determined.

The information on the specific food is preferably an amount of carbohydrate of the food consumed preferably in bread unit or a carbohydrate. The information on the specific food preferably also comprises the kind of food.

According to a further preferred embodiment of the medical device 100 the medical device 100 comprises a scanner, a bar code reader, a matrix code reader such as e.g. a QR code reader or an RFID reader for receiving the information on the specific food. Thus, the user of the medical device only needs to select the amount of the specific food consumed via the user input unit 150 in order to obtain the information on the bread units consumed.

Figure 33:
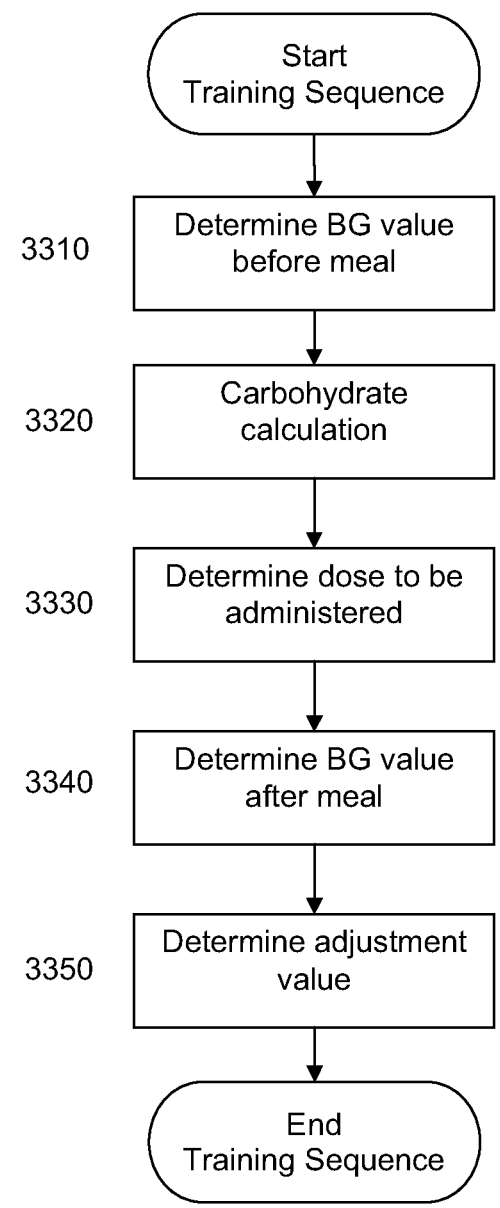
FIG. 33 is a flow diagram illustrating the method steps of a training sequence according to yet another preferred embodiment of the invention.

For determined the sensitivity on specific food and on specific insulin, the medical device 100 preferably provides a so called training sequence. FIG. 33 shows the method steps of the training sequence according to another preferred embodiment of the invention. In step 3310 the blood glucose value before the meal is determined. Preferably, the blood glucose value is determined via blood glucose measurement unit 110. In that way, additionally the time is recorded and stored together with the determined blood glucose value when the blood glucose measurement has been performed. Furthermore, in step 3320 a carbohydrate calculation is performed based on food information provided. Preferably, the determining unit 140 is arranged to perform the carbohydrate calculation based on the information on the specific food consumed. Preferably, the food information is entered by the user of the medical device 100 via the user input unit 150. Alternatively, the food information is entered via interface 170 or via the reader.

In step 3330 the dose to be administered is determined based on the carbohydrate calculation and based on an adjustment value. Preferably, the determining unit 140 is arranged to calculate the initial dose of insulin only based on the information on the specific food consumed, and initially, the adjustment value is "0". However, as explained in further detail below, the adjustment value is modified if necessary. When the dose of insulin and preferably the dose of rapid acting insulin is determined, the dose is administered and the time of administering of the dose is recorded either by user input or via interface 170 in the storage unit 130. Preferably, in step 3340 the blood glucose value after the meal is measured, when a predetermined time interval after step 3310 has lapsed. The blood glucose value determined after the meal is then compared with a predefined blood glucose value. Preferably, the determining unit 140 is arranged to determine for each specific food a specific adjustment value for the subsequent dose of insulin based at least on the information on the specific food consumed, the initial dose of insulin calculated for the specific food and a deviation of the measured blood glucose value from a predefined blood glucose value.

If the after meal blood glucose value does not correspond within a specific range to the predetermined value, the adjustment value is modified in step 3350.

By preferably repeating the training sequence several times the adjustment value converges, thus, indicating the sensitivity to the administered insulin. According to another alternative the training sequence is repeated several times in order to receive different adjustment values for different kinds of food.

Moreover, for the determining of the dose to be administered in step 3330, additionally the FBG value, the time of measuring the FBG value and the dose of long-acting basal insulin administered is considered. Accordingly, based on these training sequences, an array of adjustment values will be obtained depending on the kind of food and/or the dose of basal insulin.

Figure 34:
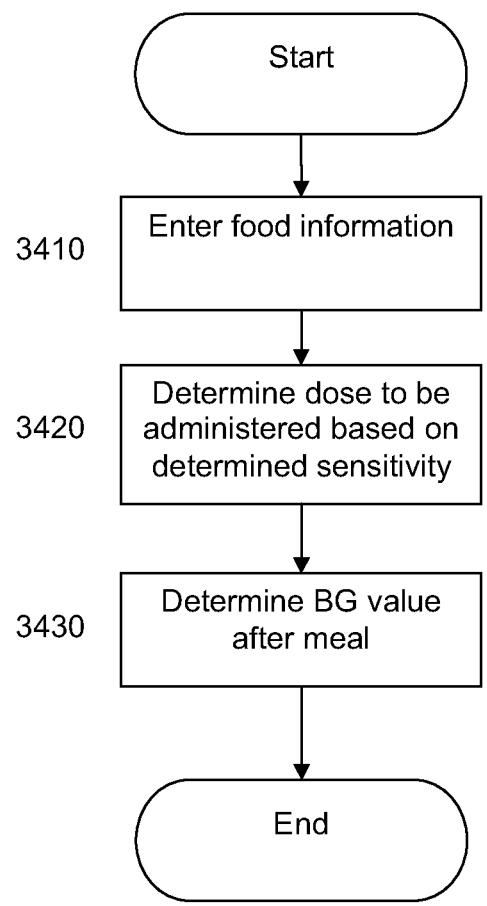
FIG. 34 is a flow diagram illustrating the method steps of according to yet another preferred embodiment of the invention.

FIG. 34 is a workflow illustrating the method steps for determining the dose adjustment for mealtime. In step 3410 food information is entered, preferably via user interface 150 into the medical device 100. Alternatively, the food information is provided via interface 170. In step 3420 the dose to be administered is determined based on the sensitivity determined by the training sequence process. Preferably, the dose is determined based on the adjustment value or the array of the adjustment value based on the food information provided. Alternatively, additionally the FBG value, the time of the measurement of the FBG value, the dose of basal insulin administered and also the recent amount of rapid acting insulin is also considered for determining the dose of e.g. rapid acting insulin. Preferably, as during the training sequence the determined dose is stored in order to be considered during subsequent dose determining steps. Optionally, in step 3430 the blood glucose value after the meal is determined and preferably stored together with the time of determination in the storage means 130. Thus, this value together with the stored dose value can be used to further refine the adjustment value or the adjustment values.

In addition to the titration methods described above, which can be applied to basal, premixed and mealtime insulin, the medical device 100, as e.g. shown in FIG. 1, FIG. 19 and FIG. 20, is preferably additionally arranged to determine a dose of insulin to be administered for a specific meal. This function is either the only function provided by the medical device 100 or a function which is provided additionally and in combination with the above described functions.

For this, the medical device 100 comprises a blood glucose measurement unit 110 arranged to measure at least one blood glucose value before and at least one blood glucose value after every meal of a day. Alternatively, the blood glucose values are measured only for predefined meals of a day. Moreover, the medical device 100 additionally comprises a determining unit 140 arranged to determine for each meal a difference between a respective blood glucose value measured before the respective meal and the respective blood glucose value measured after the respective meal. Furthermore, the determining unit 140 is arranged to determine the meal with the biggest difference.

Figure 35:
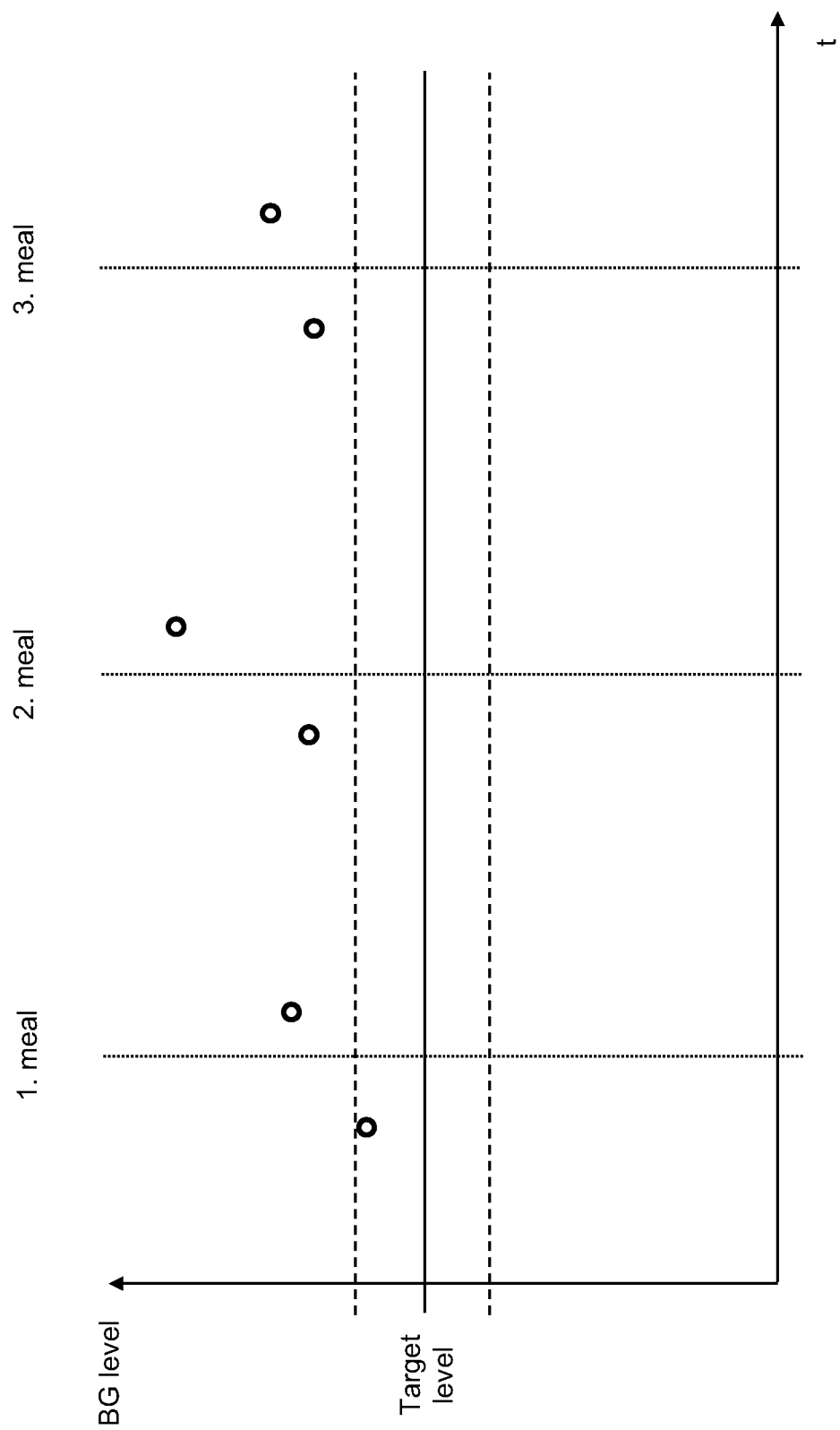
FIG. 35 is a schematic diagram showing exemplarily a chronological sequence of blood glucose values in relation to the meals consumed over a day.

In FIG. 35 a schematic diagram is illustrating exemplarily a chronological sequence of blood glucose values in relation to the meals consumed over a day. As mentioned above, preferably for all meals of a day blood glucose values are measured. The abscissa shows the time lapsed, whereby the ordinate shows the blood glucose level in respect to a predefined blood glucose level. Preferably, the predefined blood glucose level is a level around 100 mg/dl which can be considered as a target level for the blood glucose level. This predefined blood glucose value has been marked with a solid horizontal line. Furthermore, a predefined blood glucose range extends preferably below and alternatively also above the predefined blood glucose level and is indicated by horizontal dashed lines. Dotted vertical lines indicate the event that a meal has been taken. As exemplarily shown in FIG. 35, three meals are taken. However, alternatively four, five or even more meals can be taken. Accordingly, more measurements of the blood glucose values will be performed.

As shown in FIG. 35, the first blood glucose measurement is taken before the first meal. The result is represented by a circle. As indicated, this first measurement gives a blood glucose value within the target range. The second measurement is performed after the first meal and shows an increased blood glucose level. The third measurement is performed before the second meal and shows a blood glucose level which has a lower level than the second measurement. The fourth measurement is performed after the second meal and shows a blood glucose level significantly increased in regard to the third measurement. The fifth measurement is performed before the third meal and again this measurement is lower than the last measurement after the second meal. The sixth and last measurement is the measurement after the third meal and the measured blood glucose level is also increased in regard to the blood glucose level determined before the third meal. Alternatively, not only one measurement is taken before and after one or more predefined meals, but several measurements are performed in order to get a better resolution of the development of the blood glucose level. Preferably, all measured blood glucose values are stored in the storage unit 130 in relation to the time when the measurement was performed and in relation to the meal to which they refer.

Based on such measurement data the determining unit 140 preferably determines the difference between the measurement values before a respective meal and the measurement values after a respective meal. This difference can be e.g. calculated on a mean value of all measurements before and all measurements after the respective meal. Alternatively, the difference between the respective measured blood glucose values is determined based on curve fitting and curve sketching. According to another alternative curves are fitted to the measured values and based on the derivation of the fitted curves the meal with the biggest impact on the blood glucose level is determined.

Once the meal with the biggest impact on the blood glucose level has been identified, the determining means determine a dose for the identified meal.

Preferably, the measurement of the blood glucose values over a day is repeated for a predefined time interval, e.g. one week, and the analysis of the blood glucose values is performed accordingly for the accumulated values. Preferably, a repeated measurement and an analysis is performed in the case that the difference between the impacts of the different meals on the blood glucose value is small. Moreover, the impact of a meal on the blood glucose value may vary during a week. Therefore, according to another alternative the blood glucose values are determined for each day of a week.

Figure 36:
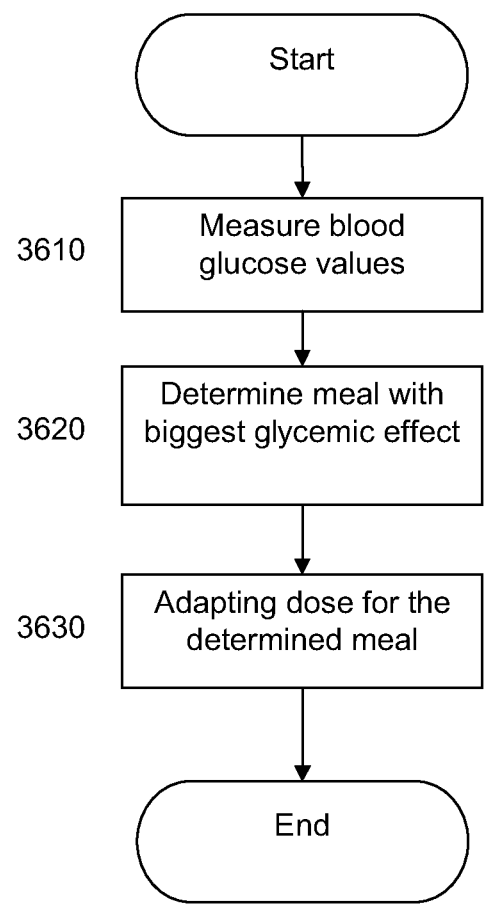
FIG. 36 is a flow diagram illustrating steps of a operating procedure according to still another preferred embodiment of the invention.

FIG. 36 is a flow diagram illustrating the steps of the method for determining a dose of insulin to be administered for glycemic control. In step 3610 at least one blood glucose value before and at least one blood glucose value after every meal of a day is measured. As mentioned above, this measurement is performed alternatively for predefined meals only. In step 3620 the meal with the biggest difference between a respective blood glucose value before the respective meal and the respective blood glucose value measured after the respective meal is determined. Finally, in step 3630 the dose for the determined meal is adapted.

By determining the dose with the biggest impact on the blood glucose level a better glycemic control can be provided. By administering the insulin for the meal with the largest influence on the blood glucose level the fluctuations of the blood sugar are reduced. Thus, a blood glucose profile is obtained with lower peaks or even less peaks. This also improves the treatment with basal insulin.

The invention claimed is:

1. A medical system for the treatment of diabetes, the medical system comprising:
    an administration computing system configured to manage security data for one or more medical devices; and
    at least one medical device for providing information for glycemic control, namely a dose of insulin to be set, the at least one medical device comprising:
        a memory arranged to store data comprising profile parameters for different dose adjustment profiles each comprising a specific initial dose value, a specific time interval for increasing the dose, a specific dose increase step and a specific low blood glucose threshold value;
        a receiver to receive blood glucose value data and the security data; and
        at least one processor connected to the receiver and configured to:
            validate the received security data and provide validation data corresponding to the validation of the received security data;
            unlock at least one first processing function and at least one second processing function for execution based on the validation data, wherein execution of the at least one first processing function and the at least one second processing function is allowed based on a control signal generated where the received security data was successfully validated, wherein the at least one first processing function includes adjusting the profile parameters for a selected dose adjustment profile and the at least one second processing function includes stepwise adapting the dose of insulin based, at least, on the selected dose adjustment profile to determine the value for the dose of insulin to be administered based on the received blood glucose value data and data retrieved from the memory, wherein the at least one second processing function is unlocked by providing the security data once, and wherein the at least one first processing function must be unlocked each time it is executed;
            execute the unlocked at least one first processing function and the unlocked at least one second processing function; and
            transmit information regarding the determined dose to a dose setter configured for administration of the determined dose of insulin to a user, wherein the delivery of the determined dose to be administered is automatically activated.

2. The medical system according to claim 1, wherein the at least one medical device further comprises a wired or wireless interface for receiving and transmitting data, the wired or wireless interface connected to the receiver and adapted to receive the security data for validation.

3. The medical system according to claim 1, wherein the administration computing system comprises at least one processor to provide the security data and a transceiver adapted to transmit the security data to a transceiver of the at least one medical device.

4. The medical system according to claim 3, wherein the at least one medical device is a plurality of medical devices, wherein the administration computing system is configured to generate the security data together with respective reference data for each of the plurality of medical devices administrated with the administration computing system, wherein unique security data are used for each medical device in the plurality of medical devices, and wherein only the unique security data corresponding to a respective medical device in the plurality of medical devices can be used as an authorization code for unlocking and/or executing specific functions of the respective medical device for each medical device in the plurality of medical devices.

5. The medical system according to claim 4, wherein for each medical device in the plurality of medical devices, the medical device comprises a chip-card reader or a chip-card reader interface, and the reference data for the medical device is stored on a chip card in or received by the medical device.

6. The medical system according to claim 5, wherein the chip card is a SIM card from which the at least one processor of the at least one medical device receives the reference data to be compared with the received security data.

7. The medical system according to claim 5, wherein for each medical device in the plurality of medical devices:
    the chip-card reader of the medical device is adapted to read a SIM card and the chip card is a SIM card;
    an interface of the medical device is a mobile communication interface and basic functions of the medical device can be unlocked via a telecommunication channel; and
    the medical device is adapted to identify itself via an international subscriber identity stored in the SIM card within a network, wherein the medical device can be checked, remote controlled, updated and/or monitored via the administration computing system by addressing the mobile communication interface.

8. The medical system according to claim 7, wherein the reference data is transmitted via the transceiver of the administration computing system.

9. The medical system according to claim 1, wherein the administration computing system is adapted to define different authorization levels, and wherein depending on an authorization level of the different authorization levels, different functionality for modifying a setup of the at least one medical device is provided based on whether the security data was successfully validated.

10. The medical system according to claim 9, wherein one or more specific functions other than the at least one first processing function and at least one second processing function can only be executed if additional security data are provided during execution of the one or more specific functions.

11. The medical system according to claim 1, wherein the at least one medical device is adapted to provide different functionality for modifying the setup of the at least one medical device including one or more of: selecting an algorithm for automatically determining the dose of insulin to be administered, modifying a new algorithm for automatically determining the dose of insulin to be administered, personalizing an algorithm for automatically determining the dose of insulin to be administered, or changing parameters stored in the memory of the at least one medical device.

12. The medical system according to claim 1, wherein the security data is a password or an activation key, and wherein the at least one processor of the at least one medical device is further configured to validate the password or the activation key based on predefined data stored in the memory or based on a corresponding key or code generated from the security data.

13. The medical system according to claim 1, wherein the at least one medical device further comprises a blood glucose measurement unit including a sensor and configured to measure a blood glucose value and to provide the blood glucose value data corresponding to the measured blood glucose value, and wherein the receiver is configured to receive the blood glucose value data from the blood glucose measurement unit.

14. The medical system according to claim 13, wherein the blood glucose measurement unit is a continuous measurement sensor that is adapted to forward data to the receiver of the at least one medical device via a wired or a wireless connection.

15. The medical system according to claim 13, wherein the blood glucose measurement unit is configured to be activated for a blood glucose measurement by the at least one medical device.

16. The medical system according to claim 1, wherein the at least one processor of the at least one medical device is further configured to set the dose of insulin based on the determined dose of insulin.

17. The medical system according to claim 1, wherein the at least one medical device, the administration computing system, or both collectively comprise a set of predefined templates for defining a new algorithm for stepwise adapting the dose of insulin to be administered, wherein the administration computing system is further configured to transmit the newly defined algorithm or an ID of the newly defined algorithm that uniquely identifies the newly defined algorithm to the at least one medical device.

18. The medical system of claim 17, wherein the at least one processor of the at least one medical device is further configured to personalize the newly defined algorithm.

19. The medical system of claim 1, wherein the administration computing system is an administration computing device.

20. The medical system of claim 1, wherein the dose setter is configured to treat diabetes by setting the determined dose on an insulin pump based on the received determined dose information.

* * * * *